US011058756B2

(12) United States Patent
Vieira et al.

(10) Patent No.: US 11,058,756 B2
(45) Date of Patent: Jul. 13, 2021

(54) COMPOSITIONS AND METHODS OF TREATING AUTOIMMUNE DISEASE BY REDUCING ENTEROCOCCUS

(71) Applicant: YALE UNIVERSITY, New Haven, CT (US)

(72) Inventors: Silvio Manfredo Vieira, New Haven, CT (US); Martin A. Kriegel, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 7 days.

(21) Appl. No.: 16/478,911

(22) PCT Filed: Jan. 19, 2018

(86) PCT No.: PCT/US2018/014368
§ 371 (c)(1),
(2) Date: Jul. 18, 2019

(87) PCT Pub. No.: WO2018/136708
PCT Pub. Date: Jul. 26, 2018

(65) Prior Publication Data
US 2019/0374632 A1    Dec. 12, 2019

Related U.S. Application Data

(60) Provisional application No. 62/448,119, filed on Jan. 19, 2017, provisional application No. 62/448,510, filed on Jan. 20, 2017.

(51) Int. Cl.
A61K 39/00     (2006.01)
A61K 39/09     (2006.01)
A61P 31/04     (2006.01)
A61K 38/14     (2006.01)

(52) U.S. Cl.
CPC .............. A61K 39/09 (2013.01); A61K 38/14 (2013.01); A61P 31/04 (2018.01)

(58) Field of Classification Search
CPC .................................................... A61K 39/09
See application file for complete search history.

(56) References Cited

U.S. PATENT DOCUMENTS

| 2002/0132285 A1 | 9/2002 | Chen |
| 2006/0116342 A1 | 6/2006 | Granstein |
| 2011/0218195 A1 | 9/2011 | Sayada |
| 2012/0121638 A1 | 5/2012 | Huebner |
| 2013/0183680 A1 | 7/2013 | Naides |

OTHER PUBLICATIONS

Gutfeld et al (Drug Intelligence and Clinical Pharmacy vol. 22, pp. 881-882) (Year: 1988).*
Terada et al (Microbial Ecology in Health and Disease vol. 16, pp. 188-194) (Year: 2004).*
Choi et al (Nutrients vol. 8, pp. 1-11) (Year: 2016).*
Abt et al., "Commensal Bacteria Calibrate the Activation Threshold of Innate Antiviral Immunity" 2012, Immunity, 37: 158-170.
Arpaia et al., "Metabolites Produced by Commensal Bacteria Promote Peripheral Regulatory T-cell Generation" Nature, 2013, 504, 451-455.
Atarashi et al., "Induction of Colonic Regulatory T Cells by Indigenous *Clostridium* Species" Science, 2011, 331, 337-341.
Balmer et al., "The Liver May Act as a Firewall Mediating Mutualism Between the Host and Its Gut Commensal Microbiota" Science Translational Medicine, 2014, 6: 237ra266.
Barman et al., "Enteric *Salmonellosis* Disrupts the Microbial Ecology of the Murine Gastrointestinal Tract" Infect Immun, 2008, 76, 907-915.
Broder et al., "Association between antiphospholipid antibodies and all-cause mortality among endstage renal disease patients with and without SLE: a retrospective cohort study" Rheumatology, 2016, 55: 817-825.
Costa et al., "Gut microbiota translocation to the pancreatic lymph nodes triggers NOD2 activation and contributes to T1D onset", Journal of Experimental Medicine, 2016, 213(7): 1223-1239.
Craft, "Follicular Helper T Cells in Immunity and Systemic Autoimmunity" Nat Rev Rheumatol, 2012, 8, 337-347.
Crotty, "T follicular helper cell differentiation, function, and roles in disease" Immunity, 2014, 41, 529-542.
Crow, "Type I Interferon in the Pathogenesis of Lupus" J Immunol, 2014, 192, 5459-5468.
Dosselaere and Vanderleyden, "A Metabolic Node in Action: Chorismate-Utilizing Enzymes in Microorganisms" Crit Rev Microbiol, 2001, 27, 75-131.
Eloranta et al., "Disease Mechanisms in Rheumatology—Tools and Pathways: Plasmacytoid Dendritic Cells and Their Role in Autoimmune Rheumatic Diseases" 2013, Arthritis Rheum, 65, 853-863.
Fung et al., "Lymphoid-Tissue-Resident Commensal Bacteria Promote Members of the IL-10 Cytokine Family to Establish Mutualism" Immunity, 2016, 44: 634-646.
Furuta et al., "E-NPP3 controls plasmacytoid dendritic cell numbers in the small intestine" PLoS One, 2017, 12, e0172509 (19 pages).
Ichinohe et al., "Microbiota regulates immune defense against respiratory tract influenza A virus infection" Proc Natl Acad Sci USA, 2011, 108: 5354-5359.
Kane et al., "Successful Transmission of a Retrovirus Depends on the Commensal Microbiota" Science, 2011, 334: 245-249.
Kriegel et al., "Naturally Transmitted Segmented Filamentous Bacteria Segregate With Diabetes Protection in Nonobese Diabetic Mice" Proc Natl Acad Sci U S A, 2011, 108, 11548-11553.

(Continued)

Primary Examiner — Albert M Navarro
(74) Attorney, Agent, or Firm — Riverside Law LLP

(57) ABSTRACT

The present invention relates to compositions and methods for treating or preventing an autoimmune disorder by reducing the amount or activity of *Enterococcus* sp. in a subject. In certain aspects, the present invention provides methods of diagnosing a subject as having an autoimmune disease or disorder by detecting an increased amount of *Enterococcus* sp. or anti-*Enterococcus* sp. antibodies in the subject.

4 Claims, 42 Drawing Sheets
Specification includes a Sequence Listing.

(56) References Cited

OTHER PUBLICATIONS

Kuss et al., "Intestinal Microbiota Promote Enteric Virus Replication and Systemic Pathogenesis" Science, 2011, 334: 249-252.
Liu and Davidson, "Taming Lupus—A New Understanding of Pathogenesis Is Leading to Clinical Advances" Nature Medicine, 2012, 18: 871-882.
Luissint et al., "Inflammation and the Intestinal Barrier: Leukocyte-Epithelial Cell Interactions, Cell Junction Remodeling, and Mucosal Repair" Gastroenterology, 2016, 151, 616-632.
Macpherson and Smith, "Mesenteric lymph nodes at the center of immune anatomy", Journal of Experimental Medicine, 2006, 203: 497-500.
Manfredo-Vieira et al., "Translocation of a gut pathobiont drives autoimmunity in mice and humans", Science, 2018, 359: 1156-1161.
Moura-Alves et al., "AhR sensing of bacterial pigments regulates antibacterial defence" Nature, 2014, 512, 387-392.
Niewold, "Advances in Lupus Genetics" Current Opinion in Rheumatology, 2015, 27: 440-447.
Patel et al., "Multiplex PCR detection of vanA, vanB, vanC-1, and vanC-2/3 genes in enterococci." J Clin Microbiol, 1997, 35, 703-707.
Qin et al., "Alterations of the Human Gut Microbiome in Liver Cirrhosis" Nature, 2014, 513, 59-64.
Ruff and Kriegel, "Autoimmune Host-Microbiota Interactions at Barrier Sites and Beyond", Trends in Molecular Medicine, 2015, 21: 233-244.
Sandler and Douek, "Microbial Translocation in HIV Infection: Causes, Consequences and Treatment Opportunities", Nature Reviews: Microbiology, 2012, 10: 655-666.
Schiering et al., "Feedback Control of AHR Signalling Regulates Intestinal Immunity" Nature, 2017, 542, 242-245.
Slack et al, "A flexible continuum between adaptive and innate immunity in maintaining host-microbiota mutualism" Science, 2006, 325: 617-620.
Smith et al., "The Microbial Metabolites, Short-Chain Fatty Acids, Regulate Colonic Treg Cell Homeostasis" Science, 2013, 341, 569-573.
Sonnenberg et al., "Innate Lymphoid Cells Promote Anatomical Containment of Lymphoid-Resident Commensal Bacteria" Science, 2012, 336: 1321-1325.
Spadoni et al., "A Gut-Vascular Barrier Controls the Systemic Dissemination of Bacteria" Science, 2015, 350: 830-834.
Spano et al., "Proteolytic targeting of Rab29 by an effector protein distinguishes the intracellular compartments of human-adapted and broad-host *Salmonella*" Proc Natl Acad Sci U S A, 2011, 108, 18418-18423.
Stockinger et al.,"The Aryl Hydrocarbon Receptor: Multitasking in the Immune System" Annu Rev Immunol, 2014, 32, 403-432.
Veldhoen et al., "The Aryl Hydrocarbon Receptor Links TH17-cell-mediated Autoimmunity to Environmental Toxins" Nature, 2008, 453, 106-109.
Viaud et al., "The Intestinal Microbiota Modulates the Anticancer Immune Effects of Cyclophosphamide" Science, 2013, 342: 971-976.
Viera et al., "Diet, microbiota and autoimmune diseases" Lupus, 2014, 23: 518-526.
Wellinghausen et al., "Rapid Identification of Clinically Relevant *Enterococcus* Species by Fluorescence In Situ Hybridization" J Clin Microbiol, 2007, 45, 3424-3426.
Wu et al., "Gut-residing Segmented Filamentous Bacteria Drive Autoimmune Arthritis via T Helper 17 Cells" Immunity, 2010, 32, 815-827.

* cited by examiner

Figure 9B

| NODE | Gene Name | Full name |
|---|---|---|
| 1 | cof | HMP-PP hydrolase (pyridoxal phosphatase) Cof, detected in genetic screen for thiamin metabolic genes (PMID:15292217) |
| 1 | ptsI | Phosphoenolpyruvate-protein phosphotransferase of PTS system (EC 2.7.3.9) |
| 1 | nifJ | Pyruvate-flavodoxin oxidoreductase (EC 1.2.7.-) |
| 1 | pycA | Pyruvate carboxylase (EC 6.4.1.1) |
| 1 | PPP5C | Serine/threonine protein phosphatase (EC 3.1.3.16) |
| 1 | nox | NADH dehydrogenase (EC 1.6.99.3) |
| 1 | nadD | Nicotinate-nucleotide adenylyltransferase (EC 2.7.7.18) |
| 2 | vanS | Sensor histidine kinase VanS (EC 2.7.3.-) |
| 2 | vanR | Vancomycin response regulator VanR |
| 2 | alr | Alanine racemase (EC 5.1.1.1) |
| 2 | maeP | Malate permease |
| 2 | Pah28 | Phage transcriptional regulator, Cro/CI family |
| 2 | AU086_gp07 | Phage antirepressor protein |
| 2 | rep | Phage replication initiation protein |
| 2 | sdhA | L-serine dehydratase, alpha subunit (EC 4.3.1.17) |
| 2 | sdhB | L-serine dehydratase, beta subunit (EC 4.3.1.17) |
| 2 | ilvE | Branched-chain amino acid aminotransferase (EC 2.6.1.42) |
| 2 | purE | Phosphoribosylaminoimidazole carboxylase catalytic subunit (EC 4.1.1.21) |
| 2 | purK | Phosphoribosylaminoimidazole carboxylase ATPase subunit (EC 4.1.1.21) |
| 2 | purC | Phosphoribosylaminoimidazole-succinocarboxamide synthase (EC 6.3.2.6) |
| 2 | purH | IMP cyclohydrolase (EC 3.5.4.10) / Phosphoribosylaminoimidazolecarboxamide formyltransferase (EC 2.1.2.3) |
| 2 | pfl | Pyruvate formate-lyase (EC 2.3.1.54) |
| 2 | pflA | Pyruvate formate-lyase activating enzyme (EC 1.97.1.4) |
| 2 | pvaA | Pneumococcal vaccine antigen A homolog |
| 4 | xpaC | 5-bromo-4-chloroindolyl phosphate hydrolysis protein |
| 4 | dhaL | Phosphoenolpyruvate-dihydroxyacetone phosphotransferase (EC 2.7.1.121), ADP-binding subunit DhaL |
| 4 | dhaK | Phosphoenolpyruvate-dihydroxyacetone phosphotransferase (EC 2.7.1.121), dihydroxyacetone binding subunit DhaK |
| 4 | dhaM | Phosphoenolpyruvate-dihydroxyacetone phosphotransferase (EC 2.7.1.121), subunit DhaM; DHA-specific IIA component |
| 4 | glyA | Serine hydroxymethyltransferase (EC 2.1.2.1) |
| 4 | serC | Phosphoserine aminotransferase (EC 2.6.1.52) |
| 4 | serA | D-3-phosphoglycerate dehydrogenase (EC 1.1.1.95) |
| 5 | sphS | Phosphate regulon sensor protein PhoR (SphS) (EC 2.7.13.3) |
| 6 | cof | HMP-PP hydrolase (pyridoxal phosphatase) Cof, detected in genetic screen for thiamin metabolic genes (PMID:15292217) |
| 6 | kdsD | Arabinose 5-phosphate isomerase (EC 5.3.1.13) |
| 6 | pta | Phosphate acetyltransferase (EC 2.3.1.8) |
| 6 | menF | Menaquinone-specific isochorismate synthase (EC 5.4.4.2) |
| 6 | pabA | Para-aminobenzoate synthase, amidotransferase component (EC 2.6.1.85) |
| 6 | NAD gapA | NAD-dependent glyceraldehyde-3-phosphate dehydrogenase (EC 1.2.1.12) |
| 6 | nadE | NAD synthetase (EC 6.3.1.5) |

Figure 24A

| NODE | Gene Name | Full name |
|---|---|---|
| 7 | tspO | Tryptophan-rich sensory protein |
| 7 | fliN | Flagellar motor switch protein FliN |
| 7 | fliM | Flagellar motor switch protein FliM |
| 7 | cheW | Positive regulator of CheA protein activity (CheW) |
| 7 | cheY | Chemotaxis regulator - transmits chemoreceptor signals to flagelllar motor components CheY |
| 7 | cheC | Chemotaxis protein CheC -- inhibitor of MCP methylation |
| 7 | cheA | Signal transduction histidine kinase CheA (EC 2.7.3.-) |
| 7 | cheR | Chemotaxis protein methyltransferase CheR (EC 2.1.1.80) |
| 7 | cheB | Chemotaxis response regulator protein-glutamate methylesterase CheB (EC 3.1.1.61) |
| 7 | cheD | Chemotaxis protein CheD |
| 7 | fliG | Flagellar motor switch protein FliG |
| 7 | flgC | Flagellar basal-body rod protein FlgC |
| 7 | flgB | Flagellar basal-body rod protein FlgB |
| 7 | motA | Flagellar motor rotation protein MotA |
| 7 | motB | Flagellar motor rotation protein MotB |
| 7 | ppdK | Pyruvate,phosphate dikinase (EC 2.7.9.1) |
| 8 | cof | HMP-PP hydrolase (pyridoxal phosphatase) Cof, detected in genetic screen for thiamin metabolic genes (PMID:15292217) |
| 8 | entB | Isochorismatase (EC 3.3.2.1) |
| 9 | cof | HMP-PP hydrolase (pyridoxal phosphatase) Cof, detected in genetic screen for thiamin metabolic genes (PMID:15292217) |
| 9 | citG | Triphosphoribosyl-dephospho-CoA synthetase (EC 2.7.8.25) |
| 9 | ribD | Diaminohydroxyphosphoribosylaminopyrimidine deaminase (EC 3.5.4.26) / 5-amino-6-(5-phosphoribosylamino)uracil reductase (EC 1.1.1.193) |
| 9 | aroK | Shikimate kinase I (EC 2.7.1.71) |
| 9 | EPSP | 5-Enolpyruvylshikimate-3-phosphate synthase (EC 2.5.1.19) |
| 9 | aroC | Chorismate synthase (EC 4.2.3.5) |
| 9 | aroB | 3-dehydroquinate synthase (EC 4.2.3.4) |
| 9 | famI1 | 2-keto-3-deoxy-D-arabino-heptulosonate-7-phosphate synthase I beta (EC 2.5.1.54) |
| 9 | aroE | Shikimate/quinate 5-dehydrogenase I beta (EC 1.1.1.282) |
| 9 | cls | Cardiolipin synthetase (EC 2.7.8.-) |
| 9 | vanZ | VanZ like protein:RDD |
| 10 | gltA | Glutamate synthase [NADPH] large chain (EC 1.4.1.13) |
| 10 | CRLS1 | Cardiolipin synthetase (EC 2.7.8.-) |
| 10 | gltB | Glutamate synthase [NADPH] small chain (EC 1.4.1.13) |
| 11 | cypX | Cytochrome P450 |
| 12 | pip | phage infection protein |
| 12 | MaeKR | Two-component response regulator, malate (EC 2.7.3.-) |
| 12 | BcrFT9 | Two-component sensor histidine kinase, malate (EC 2.7.3.-) |
| 12 | maeN | Malate Na(+) symporter |
| 12 | ME2 | NAD-dependent malic enzyme (EC 1.1.1.38) |
| 12 | cat | Chloramphenicol acetyltransferase (EC 2.3.1.28) |
| 13 | dat | D-alanine aminotransferase (EC 2.6.1.21) |
| 13 | WARS | Tryptophanyl-tRNA synthetase (EC 6.1.1.2) |
| 13 | murI | Glutamate racemase (EC 5.1.1.3) |
| 13 | NAD gapA | NAD-dependent glyceraldehyde-3-phosphate dehydrogenase (EC 1.2.1.12) |
| 17 | eat | Ethanolamine permease |
| 17 | aroD | 3-dehydroquinate dehydratase I (EC 4.2.1.10) |
| 17 | pyk | Pyruvate kinase (EC 2.7.1.40) |
| 19 | gp62 | Phage holin |

Figure 24B

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 1
tactgacaaa ccattcatga tg                                              22

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
aacttcgtca ccaacgcgaa c                                               21

<210> SEQ ID NO 3
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 3
tctcgagctc tgtacatgtc c                                               21

<210> SEQ ID NO 4
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 4
gttctagagg taccggttgt t                                               21

<210> SEQ ID NO 5
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 5
ttacttgctg attttgattc g                                               21

<210> SEQ ID NO 6
<211> LENGTH: 21
<212> TYPE: DNA
<213> ORGANISM: Artificial Sequence
```

```
<220> FEATURE:
<223> OTHER INFORMATION: Chemically Synthesized

<400> SEQUENCE: 6
tgaattcttc tttgaaatca g                                              21

<210> SEQ ID NO 7
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 7
cggcaacgag cgcaaccc                                                  18

<210> SEQ ID NO 8
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 8
ccattgtagc acgtgtgtag cc                                             22

<210> SEQ ID NO 9
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 9
gctgcctccc gtaggagt                                                  18

<210> SEQ ID NO 10
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 10
attcacaact gtgtaacatc ctat                                           24
```

COMPOSITIONS AND METHODS OF TREATING AUTOIMMUNE DISEASE BY REDUCING ENTEROCOCCUS

CROSS-REFERENCE TO RELATED APPLICATIONS

This application is a U.S. national phase application filed under 35 U.S.C. § 371 claiming benefit to International Patent Application No. PCT/US18/14368, filed Jan. 19, 2018, which is entitled to priority under 35 U.S.C. § 119(e) to U.S. Provisional Patent Application No. 62/448,119, filed Jan. 19, 2017, and U.S. Provisional Application No. 62/448,510, filed Jan. 20, 2017, each of which is hereby incorporated by reference herein in its entirety.

STATEMENT REGARDING FEDERALLY SPONSORED RESEARCH OR DEVELOPMENT

This invention was made with government support under DK079310, AI095318 and AI118855 awarded by NIH National Institute of Health. The government has certain rights in the invention.

BACKGROUND OF THE INVENTION

The gut microbiota is implicated in the pathogenesis not only of gut, but also multiple non-gut, and systemic autoimmune diseases (Ruff and Kriegel, 2015, Trends in Molecular Medicine, 21: 233-244). The exact mechanisms are not fully understood since the vast majority of the microbiota, while densely colonizing the gastrointestinal tract, are not in direct contact with the peripheral immune system that is separated by multiple layers of anatomical and functional barriers. Integrity of the gut barrier is thus essential to separate the microbiota from accessing host tissues. The gut epithelium is grossly abnormal in inflammatory bowel disease and also functionally impaired in non-gut disease states allowing for metabolites and microbial molecules to leak into the systemic circulation (e.g. in HIV disease (Sandler and Douek, 2012, Nature Reviews: Microbiology, 10: 655-666)). When intact bacteria or pathogens escape the barrier, additional mechanisms allow for capture before they reach the systemic circulation. The mesenteric lymph nodes (MLN) and liver represent 'firewalls' to commensal bacteria that escape the gut via lymphatics or blood vessels, respectively (Macpherson and Smith, 2006, Journal of Experimental Medicine, 203: 497-500; Spadoni et al., 2015, Science, 350: 830-834). This typically occurs only during intestinal pathology or in the absence of a functional innate immune system (Balmer et al., 2014, Science Translational Medicine, 6: 237ra266; Slack et al, 2006, Science, 325: 617-620; Sonnenberg et al., 2012, Science, 336: 1321-1325). Gut barrier damage during chemotherapy for cancer also leads to bacterial translocation to lymph nodes (Viaud et al., 2013, Science, 342: 971-976), as does the chemotherapeutic agent streptocozocin that induces type I diabetes (Costa et al., 2016, Journal of Experimental Medicine, 213(7): 1223-1239). The role of translocation of live pathobionts in spontaneous autoimmunity is unknown but recent studies suggest that beneficial commensals reside within gastrointestinal-associated lymphoid tissues of unmanipulated, healthy hosts (Fung et al., 2016, Immunity, 44: 634-646). A translocation into the liver, however, is not considered physiologic and is thought to occur only under major barrier breaches as described above.

Systemic lupus erythematosus (SLE) is a classic non-gut autoimmune disease that is associated with significant morbidity and mortality, especially in antiphospholipid antibody-positive patients (Broder et al., 2016, Rheumatology, 55: 817-825). The pathogenesis of systemic autoimmunity is multifactorial and involves various innate and adaptive immune pathways (Liu and Davidson, 2012, Nature Medicine, 18: 871-882). Besides the MHC locus, several genetic risk loci strongly support excessive signaling of type I interferons (IFNs) (Niewold, 2015, Current Opinion in Rheumatology, 27: 440-447). The microbiota calibrates type I and II interferon responses in non-autoimmune hosts (Abt et al., 2012, Immunity, 37: 158-170). In addition, exogenous viral infections and retroviruses contribute to immune responses and interact with the microbiota (Viera et al., 2014, Lupus, 23: 518-526; Ichinohe et al., 2011, Proc Natl Acad Sci USA, 108: 5354-5359; Kane et al., 2011, Science, 334: 245-249; Kuss et al., 2011, Science, 334: 249-252). Anti-endogenous retrovirus glycoprotein 70 (ERV gp70) responses have been shown to drive lupus kidney disease in the (NZWxBXSB)$F_1$ hybrid, that succumbs eventually to progressive autoimmune thrombi mediated by antiphospholipid (132-glycoprotein I, b2GPI) antibodies. Understanding whether spontaneous translocation of gut commensals occurs in autoimmunity and contributes to IFN and autoimmune (anti-dsDNA, anti-ERV gp70 and anti-b2GPI) responses, would aid in the development of new treatment strategies against these chronic syndromes.

Thus, there is a need in the art for compositions and methods for treating autoimmune disorders. This invention satisfies this unmet need.

SUMMARY OF THE INVENTION

In one aspect, the present invention provides a composition for treating or preventing an autoimmune disease or disorder comprising a therapeutic agent which reduces the amount or activity of *Enterococcus* sp. in a subject.

In one embodiment, the therapeutic agent comprises an immunotherapeutic agent induces an anti-*Enterococcus* sp. immune response. In one embodiment, the immunotherapeutic agent is selected from the group consisting of a vaccine, an antibody, an *Enterococcus* sp. antigen, and a nucleic acid molecule encoding an *Enterococcus* sp. antigen. In one embodiment, the vaccine comprises a heat-inactivated *Enterococcus* sp. bacterium.

In one aspect, the present invention provides a method of treating or preventing an autoimmune disease or disorder in a subject in need thereof, comprising reducing the amount or activity of *Enterococcus* sp. in a subject.

In one embodiment, the method comprises administering to the subject an effective amount of a therapeutic agent which reduces the amount or activity of *Enterococcus* sp. in a subject.

In one embodiment, the method comprises administering to the subject an antibiotic that reduces the amount or activity of *Enterococcus* sp. in a subject. In one embodiment, the antibiotic is vancomycin.

In one embodiment, the autoimmune disease or disorder is selected from the group consisting of systemic lupus erythematosus (SLE), autoimmune hepatitis (AIH), primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis.

In one aspect, the present invention provides a method of diagnosing a subject as having an autoimmune disease or disorder in a subject, comprising: obtaining a biological sample of the subject; and detecting an increased amount of anti-*Enterococcus* sp. antibodies in the biological sample relative to a control.

In one aspect, the present invention provides a method of diagnosing a subject as having an autoimmune disease or disorder in a subject, comprising: obtaining a biological sample of the subject; and detecting an increased amount of *Enterococcus* sp. in the biological sample relative to a control.

In one aspect, the present invention provides a composition for treating or preventing an autoimmune disease or disorder comprising an inhibitor of one or more components of the aryl hydrocarbon receptor (AHR) signaling pathway. In one embodiment, the inhibitor is at least one selected from the group consisting of a protein, a peptide, a peptidomimetic, an antibody, a ribozyme, a small molecule chemical compound, a nucleic acid molecule, a vector, an antisense nucleic acid molecule, and a CRISPR-associated enzyme or guide RNA.

In one aspect, the present invention provides a method of treating or preventing an autoimmune disease or disorder in a subject in need thereof, comprising administering to the subject an effective amount of an inhibitor of one or more components of the aryl hydrocarbon receptor (AHR) signaling pathway.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1, comprising (FIG. 1A) Vancomycin (VANC), ampicillin (AMP), metronidazole (METR), neomycin (NEO) or control water (CTRL) were provided in the drinking water starting at 6 weeks of age. Mice were followed for 30 weeks or until death from autoimmunity (**$P<0.002$, Log rank test and Gehan-Breslow-Wilcoxon test). Serum anti-dsDNA (FIG. 1B) and anti-RNA (FIG. 1C) IgG at 16-weeks of age. Proteinuria levels (FIG. 1D) (*$P<0.03$, $P<0.002$ and **$P<0.0001$, Student's t test), H&E staining of involved organs (FIG. 1E), and histologic scoring (FIG. 1F-FIG. 1I) for each organ from treated animals as indicated.

FIG. 2, comprising

FIG. 3, comprising (FIG. 3A) RNA-seq was performed with ileum small intestinal cells isolated from 14-week old monocolonized mice. Heatmap shows transcripts differentially expressed in the ileum 8 hours after commensal delivery. (FIG. 3O) Confocal imaging of gut tissues was performed as described elsewhere herein. Shown are the localizations of TJ proteins in green: occludin, JAM-A, claudin-3 and claudin-5. Images are representative of 6 different mice each. Scale bars: 40 µm.

(FIG. 4A) *E. gallinarum* lysates (EG) or EG RNA were co-cultured with hepatocytes from 14-week-old (NZWxBXSB)$F_1$ mice and ERV gp70 expression was measured at time points as indicated by RT-qPCR. EG RNAse- and EG RNAse/DNAse-treated lysates were used as controls.

FIG. 5, comprising

FIG. 6, comprising

FIG. 7, comprising

FIG. 8, comprising (FIG. 8A) Principal coordinate analysis of weighted UniFrac distances was performed using QIIME to determine beta-diversity among groups (n=18 for vancomyin, n=10 for ampicillin, n=8 for metronidazole, n=13 for neomycin, n=20 for controls at 16 weeks of age). (FIG. 8B) Cladogram generated using LEfSe shows statistically significant differences between vancomycin- and control-treated groups (n=38 mice and 4 cages per each group). (Figure C) Histogram of the LDA scores generated with LEfSe is shown with the most differential taxa in the vancomycin group in green, in the control group in red.

Figure 9B:
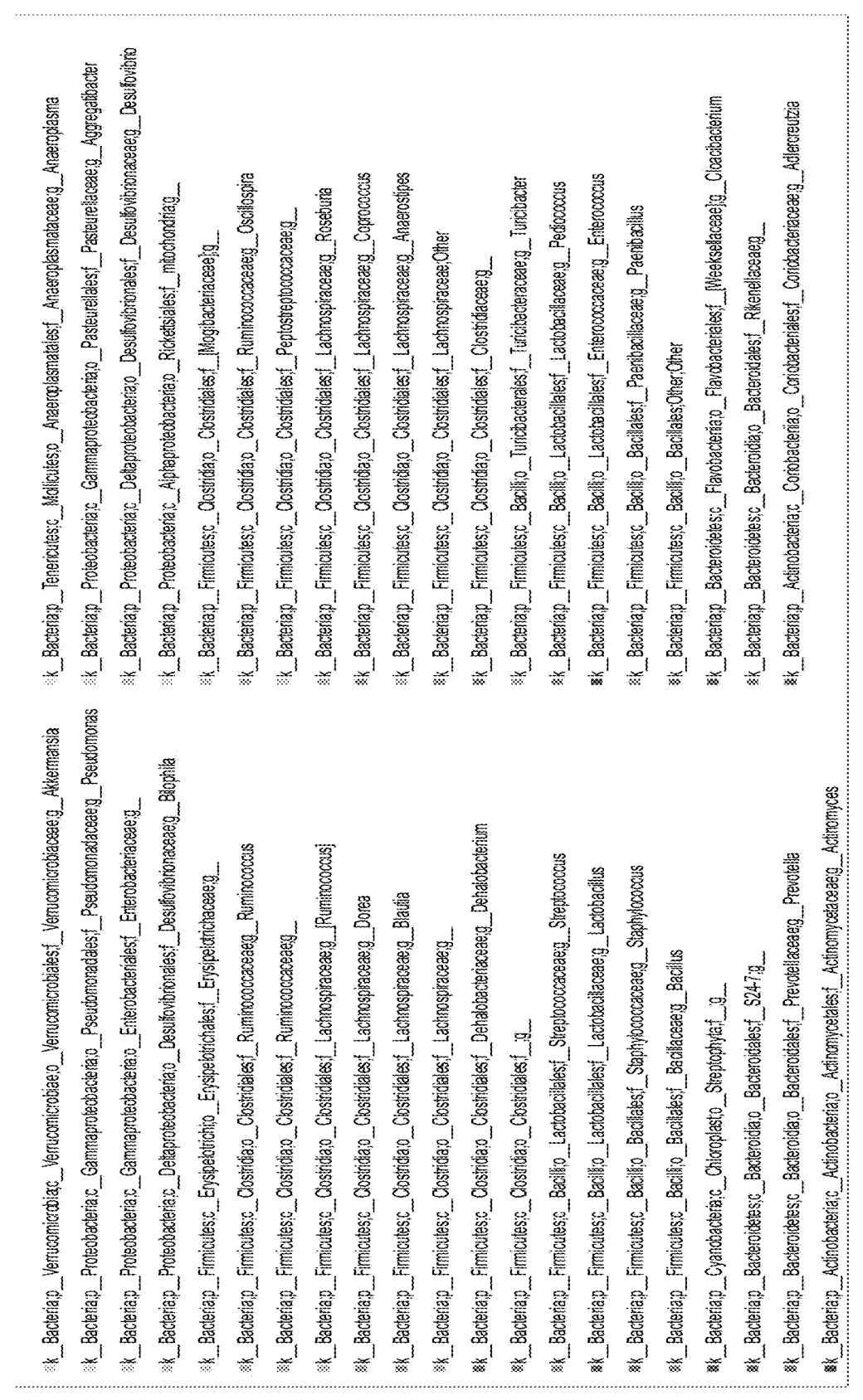

FIG. 9, comprising FIG. 9A and FIG. 9B, depicts the results of example experiments demonstrating the relative abundances of taxa determined by 16S rDNA sequencing of faecal pellets from antibiotics- and control-treated (NZWxBXSB)F$_1$ mice. Dual-index 16S rDNA sequencing of the V4 variable region from longitudinally collected faecal pellets from (NZWxBXSB)F$_1$ mice was performed as described in Material and Methods. Vancomycin (0.5 g/L; VANC), ampicillin (1.0 g/L; AMP), metronidazole (1.0 g/L; METR), neomycin (1.0 g/L; NEO) or control water treatment (CTRL) were orally administered in the drinking water starting at 6 weeks of age and faecal pellets were analysed by 16S rDNA sequencing at 16 weeks of age. Shown are the relative abundances of taxa at the genus level ((n=18 for vancomyin, n=10 for ampicillin, n=8 for metronidazole, n=13 for neomycin, n=20 for controls) See Manfredo-Vieira et al., (2018, *The Enemy Lies Within: Spontaneous Translocation of a Gut Pathobiont Drives Autoimmunity*, Science).

FIG. 10, comprising (FIG. 10A and FIG. 10B) *Enterococcus* genus and (FIG. 10C and FIG. 10D) *E. gallinarum* species-specific PCRs of DNA from human and murine stool. (FIG. 10A) *Enterococcus* genus and (FIG. 10C) *E. gallinarum* species-specific PCRs of DNA from human stool (autoimmune patients, samples 1-16), *E. gallinarum* (sample 17), *E. faecalis* (sample 18), pooled germ-free faecal controls (sample 19), *E. gallinarum*-monocolonized mouse faeces (samples 20-22, monocolonized for 3 weeks) and water control (sample 23). (FIG. 10B) *Enterococcus* genus and (FIG. 10D) *E. gallinarum* species-specific PCRs of DNA from murine (NZWxBXSB)F$_1$ stool (samples 1-13, 16 weeks of age), *E. gallinarum* (sample 14), *E. faecalis* (sample 15), and water control (sample 16). Product sizes are 112 bp for *Enterococcus* and 173 bp for *E. gallinarum*.

FIG. 11, comprising (FIG. 11A) Nose (1-2, antibiotics treatment; 3-4, no treatment), mouth (5-6, antibiotics treatment; 7-8, no treatment) and luminal content from the duodenum (9-10, antibiotics treatment; 11-12, no treatment). (FIG. 11B) Adherent duodenum (1-2, antibiotics treatment; 3-4, no treatment), luminal content from duodenum (5-6, antibiotics treatment; 7-8, no treatment) and adherent ileum (9-10, antibiotics treatment; 11-12, no treatment). (FIG. 11C) Liver (1-2, antibiotics treatment; 3-4, no treatment), spleen (5-6, antibiotics treatment; 7-8, no treatment) and feces (9-10, antibiotics treatment; 11-12, no treatment). (FIG. 11D and FIG. 11E) 24 (NZWxBXSB)$F_1$ mice were evaluated for bacterial translocation in 3 different facilities (n=8 mice per facility; Amistad Building facility, AMI; George Street facility, GEO; The Anlyan Building Center facility, TAC). Livers were harvested at 16-weeks of age and cultured in thioglicollate medium under anaerobic conditions for 72 hours and E. gallinarum species-specific PCRs was performed (FIG. 11D). Colony-forming units (CFU) were counted from liver cultures of each animal from the different animal facility (AMI, GEO, TAC) (FIG. 11E).

FIG. 15, comprising (FIG. 15A) JAM-A and (FIG. 15B) cingulin. Images are representative of 6 different mice each. Scale bars: 20 µm.

FIG. 16, comprising (FIG. 16A) Blood vessels (CD31, red) and vascular endothelial cadherin (VE-cadh, green). (FIG. 16) β-catenin (red) and vascular endothelial cadherin (VE-Cadh, green). Images are representative of 6 different mice each. Scale bars: 20 µm.

FIG. 17, comprising

FIG. 19, comprising (FIG. 19A) (NZWxBXSB)$F_1$ mice (n=5 each group) were treated from 6 weeks of age until 14 weeks of age with control water (CTRL) or vancomycin (VANC) in the drinking water. Splenocyte cultures were stimulated in vitro with soluble anti-CD3 (1 µg/mL) and anti-CD28 (2 µg/mL) for 3 days.

Cytokine levels were measured using a LEGENDplex kit and displayed as a heatmap. (FIG. 19B) Th17 cell frequencies were determined by FACS analysis of intracellular IL-17A within $CD3^+$ $CD4^+$ $CD19^-$ $CD44^+$ cells in the spleen and mesenteric lymph nodes (MLN) of 14-week-old $(NZWxBXSB)F_1$ mice (n=5) treated for 8 weeks with control water (CTRL) or broad-spectrum antibiotics (ABX; 0.5 g/L of vancomycin, 1.0 g/L ampicillin, 1.0 g/L metronidazole and 1.0 g/L neomycin) in the drinking water (*P=0.0147 and ***P=0.0007, Student t test). (FIG. 19C) Tfh and Tfr cell frequencies and ratio were determined by FACS from MLN of mice as in (FIG. 19B). Tfh and Tfr were defined by gating on $CD4^+$ $CD44^+$ $PSGL-1^-$ $Ly6C^-$ $CXCR5^+$ $PD-1^+$ and $GITR^+$. Shown are representative FACS plots as well as Tfh/Tfr frequencies of individual mice (*P<0.02 and *P=0.002, Student t test). (FIG. 19D) Vancomycin effects on MLN Th17 cells when administered in vivo compared to when added in vitro to T cell cultures. In vivo panels show MLN Th17 cell frequencies from vancomycin (VANC)- or control water (CTRL)-treated $(NZWxBXSB)F_1$ mice (n=5, 16 weeks of age) by FACS analysis of $CD3^+$ $CD4^+$ $CD19^-$ $CD44^+$. In vitro panels show MLN cultures from 16-week-old $(NZWxBXSB)F_1$ mice were treated with vancomycin (16 µg/mL) and stimulated in vitro with soluble anti-CD3 (1 µg/mL) and anti-CD28 (2 µg/mL) for 3 days. Th17 cell frequencies were analyzed by intracellular staining of IL-17A within $CD3^+$ $CD4^+$ $CD19^-$ $CD44^+$ cells. Shown is one representative experiment out of three experiments (*P=0.0010, Student's t test).

FIG. 21, comprising (FIG. 21A) Cartoon summarizing the experimental setup. During the experimental 4 weeks of bacterial gavage, mice were treated with streptomycin (5 g/L) in drinking water to allow for persistence of S. typhimurium. At 12 weeks of age, mice were evaluated for leakiness of the gut barrier by orally delivered FITC-dextran. Briefly, mice were weighed and fasted for 4 hours prior to oral FITC-dextran administration. After 4 hours of the administration, FITC-dextran in the serum was measured (P=0.0031, *P<0.0007 and ****P<0.0001, Student t test) (FIG. 21B), and for translocation to the liver (*P=0.0147, P<0.0044 and *P=0.0004, Student t test) (FIG. 21C) as well as autoantibody induction (***P<0.0003, Student t test) (FIG. 21D).

FIG. 22, depicting (FIG. 22A) Cartoon summarizing the experimental setup. $(NZWxBXSB)F_1$ mice were either weaned at 4 weeks of age and immediately gavaged and immunized or first treated orally at 6 weeks of age for 2 weeks with broad-spectrum antibiotics before gavage and immunization. All groups were gavaged with vancomycin-resistant E. gallinarum at the indicated age. No vaccination (CTRL) or an intramuscular vaccine against E. gallinarum (V-EG), E. faecalis (V-EF), B. thetaiotaomicron (V-BT) or no antigen (V-EMPTY) were administered simultaneously. Anti-dsDNA (FIG. 22B) and anti-RNA (FIG. 22C) IgG autoantibodies were measured in serum by ELISA (*P<0.03, P<0.008 and *P<0.0004, ANOVA followed by the Bonferroni test). (FIG. 22D-FIG. 22F) Kaplan-Meier survival curves show a significant survival benefit for the E. gallinarum-vaccinated groups when treatment was started at 4 weeks of age after weaning, at 8 weeks of age when autoantibodies start to rise, and also at 12 weeks of age when organ manifestations are occurring with deterioration of the clinical status of mice (*P<0.027 and **P<0.0036, Log rank test and Gehan-Breslow-Wilcoxon test). (FIG. 22G) Anaerobic cultures of livers from 16-week-old $(NZWxBXSB)F_1$ mice show absence of E. gallinarum growth in E. gallinarum-vaccinated mice (*P<0.001 and ****P<0.0001, Student's t test).

FIG. 24, comprising FIG. 24A and FIG. 24B, provides a selected gene list from the E. gallinarum genome. Full genome sequencing was performed as detailed elsewhere herein. Selected genes from the gene cluster 1-27 that are shown in FIG. 4N are listed. These include genes encoding enzymes involved in metabolism, in particular the shikimate pathway and cardiolipin synthesis, as well as several phage-related genes. These were selected based on their potential contribution to the autoimmune-promoting host pathways induced by E. gallinarum in vivo such as AhR/Cyp1a1 activation, anti-phospholipid antibody production, and type I interferon induction.

DETAILED DESCRIPTION

Figures 1A, 1B, 1C, 1D, 1E:
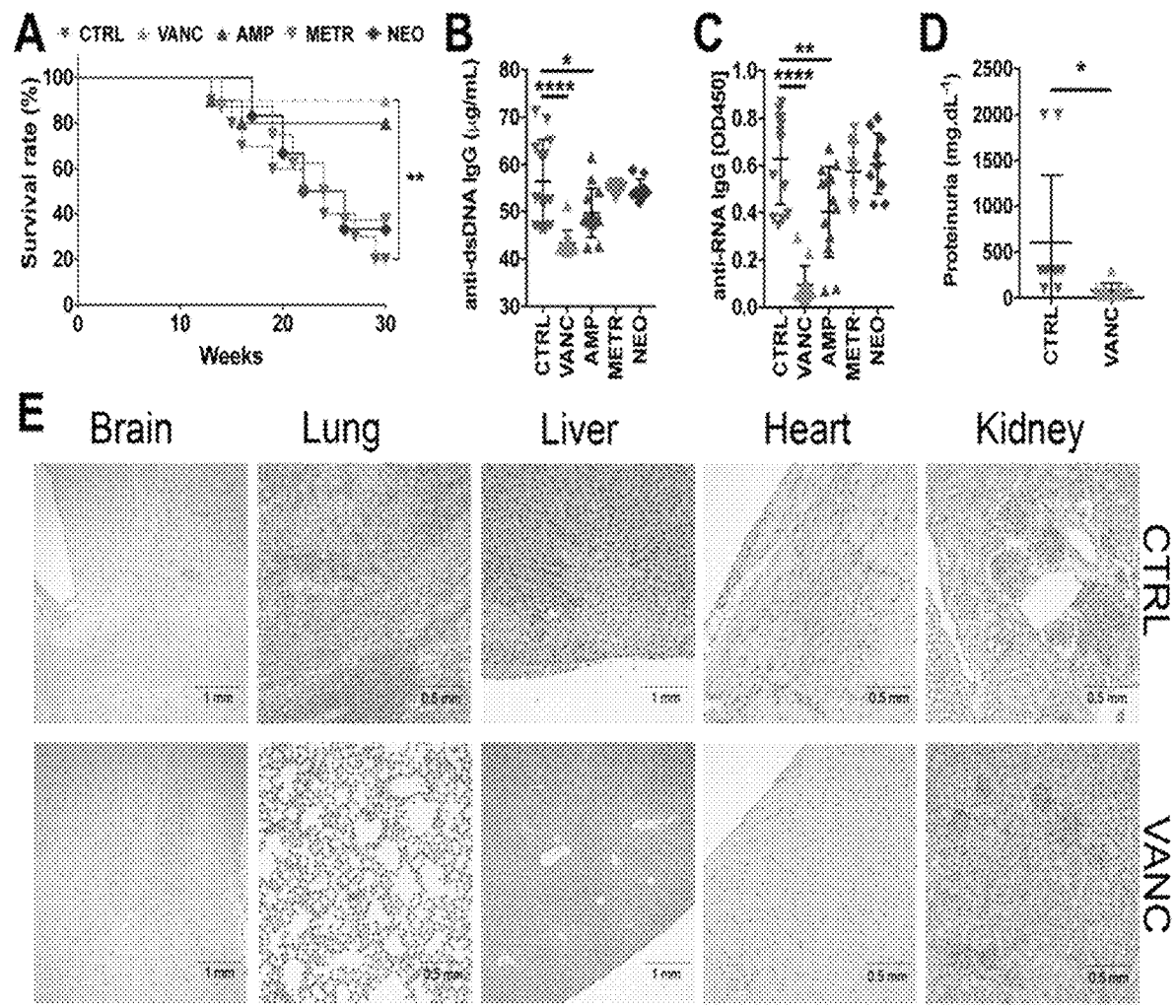
FIG. 1A through FIG. 1N, depicts the results of example experiments demonstrating the effect of antibiotics on autoimmunity and commensal translocation in (NZWxBXSB)$F_1$ mice.

The present invention provides compositions and methods for treating or preventing an autoimmune disease or disorder in a subject. In certain embodiments, the invention provides compositions and methods for treating or preventing an autoimmune disease or disorder by reducing the amount or activity of *Enterococcus* sp. bacteria in a subject in need thereof. For example, in certain embodiments, the composition comprises an immunotherapeutic agent that induces an immune response against *Enterococcus* sp. in a subject.

In certain embodiments, the invention provides compositions and methods for treating or preventing an autoimmune disease or disorder by inhibiting the expression or activity of one or more components of the aryl hydrocarbon receptor (AHR) signaling pathway.

The present invention also provides a method for diagnosing, or assessing the risk of developing, an autoimmune disease or disorder in a subject. In one embodiment, the method comprises detecting an increased amount of *Enterococcus* sp. in a biological sample of the subject, relative to a comparator. In one embodiment, the method comprises detecting an increased amount of anti-*Enterococcus* sp. antibodies in a biological sample of the subject, relative to a comparator.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequence or a partial nucleotide sequence encoding a protein that elicits an adaptive immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "adjuvant" as used herein is defined as any molecule to enhance an antigen-specific adaptive immune response.

"Immune response," as the term is used herein, means a process involving the activation and/or induction of an effector function in, by way of non-limiting examples, a T cell, B cell, natural killer (NK) cell, and/or antigen-presenting cells (APC). Thus, an immune response, as would be understood by the skilled artisan, includes, but is not limited to, any detectable antigen-specific activation and/or induction of a helper T cell or cytotoxic T cell activity or response, production of antibodies, antigen presenting cell activity or infiltration, macrophage activity or infiltration, neutrophil activity or infiltration, and the like.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "pathobiont," as used herein, refers to potentially disease-causing members of the microbiota that are present in the microbiota of a non-diseased or a diseased subject, and which has the potential to contribute to the development or progression of a disease or disorder.

An "effective amount" or "therapeutically effective amount" of a compound is that amount of a compound which is sufficient to provide a beneficial effect to the subject to which the compound is administered.

As used herein, an "instructional material" includes a publication, a recording, a diagram, or any other medium of expression which can be used to communicate the usefulness of a compound, composition, or method of the invention in a kit. The instructional material of the kit of the invention can, for example, be affixed to a container which contains the identified compound, composition, or method of the invention or be shipped together with a container which contains the identified compound, composition, or method of the invention. Alternatively, the instructional material can be shipped separately from the container with the intention that the instructional material and the compound, composition, or method of the invention be used cooperatively by the recipient.

The term "microarray" refers broadly to "protein microarrays", "DNA microarrays" and "DNA chip(s)," and encompasses all art-recognized solid supports, and all art-recognized methods for affixing proteins or nucleic acid molecules thereto or for synthesis of proteins or nucleic acids thereon.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is, by way of non-limiting examples, a human, a dog, a cat, a horse, or other domestic mammal.

A "therapeutic" treatment is a treatment administered to a subject who exhibits signs or symptoms of pathology, for the purpose of diminishing or eliminating those signs or symptoms.

As used herein, "treating a disease or disorder" means reducing the severity and/or frequency with which a sign or symptom of the disease or disorder is experienced by a patient.

The phrase "biological sample" as used herein, is intended to include any sample comprising a cell, a tissue, feces, or a bodily fluid in which the presence of a microbe, nucleic acid or polypeptide is present or can be detected. Samples that are liquid in nature are referred to herein as "bodily fluids." Biological samples may be obtained from a patient by a variety of techniques including, for example, by scraping or swabbing an area of the subject or by using a needle to obtain bodily fluids or tissues. Methods for collecting various body samples are well known in the art.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain instances, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In certain instances, all nucleotide residues of the first portion are capable of base pairing with nucleotide residues in the second portion.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating or preventing an autoimmune disease or disorder in a subject, by reducing the amount or activity of *Enterococcus* sp. bacteria in a subject in need thereof. The present invention is based in part upon the discovery that *Enterococcus* sp., a commensal gram-positive bacteria triggers autoimmunity. For example, it is demonstrated herein that *Enterococcus* sp. translocates from the gut through the gut barrier and into internal tissues where it stimulates an inflammatory response. Further, it is shown that depleting *Enterococcus* sp. reduces organ-specific and systemic autoimmunity.

In one aspect, the present invention provides a composition for treating or preventing an autoimmune disease or disorder in a subject. In one embodiment, the composition comprises a therapeutic agent that reduces the amount or activity of *Enterococcus* sp. in a subject. In one embodiment, the therapeutic agent is an immunotherapeutic agent that induces an immune response against *Enterococcus* sp, thereby reducing or depleting the amount of *Enterococcus* sp.

In one aspect, the composition comprises an inhibitor of the expression, activity, or both of AHR or a component of the AHR signaling pathway. For example, it is demonstrated herein that inhibiting AHR activity reduces the ability of *Enterococcus* sp. to trigger an autoimmune response. In one embodiment, the inhibitor is selected from a protein, a peptide, a peptidomimetic, an antibody, a ribozyme, a small molecule chemical compound, a nucleic acid, a vector, and an antisense nucleic acid molecule.

In one aspect, the present invention provides a method for treating or preventing an autoimmune disease or disorder in a subject. In one embodiment, the method comprises administering to the subject a composition comprising a therapeutic agent that reduces the amount or activity of *Enterococcus* sp. in a subject. In certain embodiments, the method comprises administering to the subject an antibiotic that reduces the amount or activity of *Enterococcus* sp. in a subject. In certain embodiments, composition comprises an immunotherapeutic agent that induces an immune response against *Enterococcus* sp. in a subject.

In one embodiment, the method comprises administering to the subject a composition comprising an inhibitor of the expression, activity, or both of AHR or a component of the AHR signaling pathway.

Autoimmune diseases or disorders treated or prevented by way of the present invention include, but is not limited to, systemic lupus erythematosus (SLE), autoimmune hepatitis (AIH), primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis. In certain embodiments, the compositions and methods of the invention are useful to treat or prevent liver inflammation and cirrhosis.

In one aspect, the present invention relates to compositions and methods for detecting the presence or amount of *Enterococcus* sp. in a subject. In various embodiments, the relative amount of *Enterococcus* sp. in a biological sample of a subject is indicative of the presence of an autoimmune disease or disorder. In some embodiments, the detection of *Enterococcus* sp. in a biological sample of a subject is used to diagnose the subject as having, or as at risk of developing, an autoimmune disease or disorder.

In one aspect, the present invention relates to compositions and methods for detecting the presence or amount of anti-*Enterococcus* sp. antibodies in a subject. In various embodiments, the relative amount of anti-*Enterococcus* sp. antibodies in a biological sample of a subject is indicative of the presence of an autoimmune disease or disorder. In some embodiments, the detection of anti-*Enterococcus* sp. antibodies in a biological sample of a subject is used to diagnose the subject as having, or as at risk of developing, an autoimmune disease or disorder.

In certain embodiments, the present invention is used to diagnose the subject as having, or as at a risk of developing an autoimmune diseases or disorder including, but not limited to, SLE, AIH, primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis. In certain embodiments, invention is useful to diagnosis liver inflammation and cirrhosis.

As used herein, *Enterococcus* sp. refers to one or more species of the genus *Enterococcus*. Exemplary species of *Enterococcus* include, but is not limited to, *Enterococcus alcedinis, Enterococcus aquimarinus, Enterococcus asini, Enterococcus avium, Enterococcus bulliens, Enterococcus caccae, Enterococcus camelliae, Enterococcus canintestini, Enterococcus canis, Enterococcus casseliflavus, Enterococcus cecorum, Enterococcus columbae, Enterococcus devriesei, Enterococcus diestrammenae, Enterococcus dispar, Enterococcus durans, Enterococcus eurekensis, Enterococcus faecalis, Enterococcus faecium, Enterococcus gallinarum, Enterococcus gilvus, Enterococcus haemoperoxidus, Enterococcus hermanniensis, Enterococcus hirae, Enterococcus italicus, Enterococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus pseudoavium, Enterococcus quebecensis, Enterococcus raffinosus, Enterococcus ratti, Enterococcus rivorum, Enterococcus rotai, Enterococcus saccharolyticus, Enterococcus silesiacus, Enterococcus solitaries, Enterococcus sulfureus, Enterococcus termitis, Enterococcus thailandicus, Enterococcus ureasiticus, Enterococcus ureilyticus, Enterococcus viikkiensis, Enterococcus villorum,* and *Enterococcus xiangfangensis.*

Compositions

The present invention provides a composition for treating or preventing an autoimmune disease or disorder in a subject. In one embodiment, the composition comprises a therapeutic agent that reduces the amount or activity of *Enterococcus* sp. in a subject.

In various embodiments, the composition comprises an inhibitor of *Enterococcus* sp. activity. For example, in certain embodiments, the composition comprises a protein, a peptide, a peptidomimetic, an antibody, a ribozyme, a small molecule chemical compound, a nucleic acid molecule, a vector, an antisense nucleic acid molecule, a CRISPR-associated enzyme or guide RNA, or the like which reduces the amount or activity of *Enterococcus* sp. in a subject. In certain embodiments, the inhibitor may reduce or prevent *Enterococcus* sp. replication in a subject. In certain embodiments, the inhibitor may reduce or prevent *Enterococcus* sp. translocation in a subject.

In certain aspects, the therapeutic agent comprises an inhibitor of an *Enterococcus* sp. protein or gene or a host protein or gene, where the inhibitor reduces *Enterococcus* sp. activity of inducing an inflammatory response in host tissue. For example, in one embodiment, the therapeutic agent comprises an inhibitor of an *Enterococcus* sp. protein or gene or a host protein or gene, where the inhibitor reduces or prevents *Enterococcus* sp. translocation across the gut barrier. In one embodiment, the therapeutic agent comprises an inhibitor of an *Enterococcus* sp. protein or gene or a host protein or gene, where the inhibitor reduces or prevents *Enterococcus* sp. replication.

In certain aspects, the host gene or protein inhibited by the composition comprise AHR or a component of the AHR signaling pathway. In one embodiment, the therapeutic agent comprises an inhibitor of the expression, activity, or both, of AHR or a component of the AHR signaling pathway.

An inhibitor composition of the invention can include, but should not be construed as being limited to, a chemical compound, a protein, a peptide, a peptidomimetic, an antibody, a ribozyme, a small molecule chemical compound, an antisense nucleic acid molecule (e.g., siRNA, miRNA, etc.), CRISPR-mediated gene editing components (e.g., Cas9, gRNA, etc.). One skilled in the art would readily appreciate, based on the disclosure provided herein, that an inhibitor composition encompasses a chemical compound that decreases the amount or activity of an *Enterococcus* sp. or host protein or gene associated with *Enterococcus* sp.-mediated inflammatory response. Additionally, an inhibitor composition encompasses a chemically modified compound, and derivatives, as is well known to one skilled in the chemical arts.

Further, one skilled in the art would, when equipped with this disclosure and the methods exemplified herein, appreciate that an inhibitor composition includes such inhibitors as discovered in the future, as can be identified by well-known criteria in the art of pharmacology, as described in detail herein and/or as known in the art. Therefore, the present invention is not limited in any way to any particular inhibitor as exemplified or disclosed herein; rather, the invention encompasses those inhibitors that would be understood by the routineer to be useful as are known in the art and as are discovered in the future.

In one embodiment, the composition comprises an immunotherapeutic agent which induces an immune response against *Enterococcus* sp. Exemplary immunotherapeutic agents may include, for example, a vaccine, an antibody, or fragment thereof; a cell (e.g. T-cell) modified to express an antibody, or fragment thereof, an *Enterococcus* sp. antigen, a nucleic acid molecule encoding a *Enterococcus* sp. antigen, and the like.

Small Molecule Inhibitors

In various embodiments, the inhibitor is a small molecule chemical compound. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analogue or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to inhibit group II introns.

In one embodiment, the small molecule inhibitors described herein can independently be derivatized/analogued by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In one embodiment, the composition comprises a small molecule inhibitor of AHR. For example, in one embodiment, the small molecule inhibitor of AHR comprises CH223191 (also referred to as 1-Methyl-N-[2-methyl-4-[2-(2-methylphenyl)diazenyl]phenyl-1H-pyrazole-5-carboxamide or 2-Methyl-2H-pyrazole-3-carboxylic acid (2-methyl-4-o-tolylazo-phenyl)-amide)

Nucleic Acid Inhibitors

In one embodiment, the inhibitor comprises a nucleic acid molecule, vector, or gene therapy agents.

In some instances, the inhibitor is an antisense molecule or aptamer, which inhibits one or more *Enterococcus* sp. proteins or genes or one or more host proteins or genes, such as one or more components of the AHR signaling pathway. In one embodiment, the nucleic acid comprises a promoter/regulatory sequence such that the promoter/regulatory sequence is capable of directing expression of the nucleic acid or increasing or decreasing stability of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In one embodiment, siRNA is used to inhibit one or more *Enterococcus* sp. proteins or genes or one or more host proteins or genes. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of inhibiting group II intron splicing using RNAi technology.

In another embodiment, the invention includes a vector comprising an siRNA or antisense polynucleotide. In one embodiment, the siRNA or antisense polynucleotide is capable of inhibiting group II intron splicing. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another embodiment, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin (e.g., IgG). The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queuosine, and wybutosine and the like, as well as acetyl-methyl-, thio- and other modified forms of adenine, cytidine, guanine, thymine, and uridine.

Antisense molecules and their use for inhibiting RNA molecules are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

In one embodiment, antisense molecules of the invention may be made synthetically. In one embodiment, antisense oligomers of between about 10 to about 30 nucleotides are used, since they are easily synthesized for administration to a subject or a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit one or more *Enterococcus* sp. proteins or genes or one or more host proteins or genes. Ribozymes useful for inhibiting a target molecule may be designed by incorporating target sequences into the basic ribozyme structure which are complementary, for example, to the mRNA sequence encoding one or more *Enterococcus* sp. or host proteins. Ribozymes may be synthesized using commercially available reagents (Glen Research Corp., Sterling, Va., or BioAutomation, Plano, Tex.) or they may be genetically expressed from DNA encoding them.

Genome Editing Compositions

In one embodiment, the invention provides for inhibition of one or more *Enterococcus* sp. proteins or genes or one or more host proteins or genes through use of a genome editing system. A series of programmable nuclease-based genome editing technologies have developed (see for example, Hsu et al., Cell 157, Jun. 5, 2014 1262-1278), including, but not limited to, meganucleases, zinc finger nucleases (ZFNs), transcription activator-like effector-based nucleases (TALENs) and CRISPR-Cas systems (see e.g. Platt et al., Cell 159(2), 440-455 (2014); Shalem et al., Science 3 84-87 (2014); and Le Cong et al., Science 339, 819 (2013)) or alternative CRISPR systems. Genome editing systems have a wide variety of utilities including modifying (e.g., deleting, inserting, translocating, inactivating, activating, repressing, altering methylation, transferring specific moieties) a target polynucleotide in a multiplicity of cell types.

In one embodiment, a CRISPR-Cas system, where a guide RNA (gRNA) targeted to a target nucleic acid sequence, and a CRISPR-associated (Cas) peptide form a complex to induce mutations within the targeted nucleic acid sequence. The CRISPR complex of the invention provides an effective means for modifying a target nucleic acid sequence.

In one embodiment, the composition of the present invention comprises a Cas peptide or Cas-derived peptide and a gRNA targeted to an *Enterococcus* sp. or host gene, coding sequence, or regulatory sequence. In one embodiment, the composition comprises a nucleic acid molecule encoding a Cas peptide or Cas-derived peptide. In one embodiment, the composition comprises a nucleic acid molecule encoding a gRNA targeted to an *Enterococcus* sp. or host gene, coding sequence, or regulatory sequence.

In one embodiment, the target polynucleotide is a DNA molecule. DNA molecules include, but are not limited to, genomic DNA molecules, extrachromosomal DNA molecules, conjugative plasmids and exogenous DNA molecules. In one embodiment, the target polynucleotide is a RNA molecule (see e.g., Batra et al., Cell. 170(5):899-912.e10 (2017) for methods of use of a CRISPR-Cas system to modify an RNA molecule.)

In general, "CRISPR-Cas system" or "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system are derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In some embodiments, the site of nuclease activity is determined by the CRISPR-Cas system guide RNA. In general, a "CRISPR-Cas guide RNA" or "guide RNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In the context of formation of a CRISPR complex, a "target sequence" or "a sequence of a target DNA" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides or DNA/RNA hybrid polynucleotides. In some embodiments, a target sequence is located in the nucleus or cytoplasm of a cell. In some embodiments, the target sequence may be within an organelle of a eukaryotic cell, for example, mitochondrion or chloroplast.

In some embodiments, the CRISPR-Cas domain comprises a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csc5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, orthologs thereof, or modified versions thereof. In some embodiments, the Cas protein has DNA or RNA cleavage activity. In some embodiments, the Cas protein directs cleavage of one or both strands of a nucleic acid molecule at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In one embodiment, the CRISPR-Cas domain is associated with one or more functional domains. For example, in one embodiment, one or more functional domains may be associated with (i.e., bound to or fused with) the C terminus or the N terminus of the Cas9 enzyme or homolog or ortholog thereof. In such an embodiment, the functional domains are typically fused via a linker. In another embodiment, one or more functional domains may be provided along with the Cas9 enzyme or homolog or ortholog thereof.

The one or more functional domains may have one or more activities including, but not limited to, cytidine deaminase activity, methylase activity, demethylase activity, transcription activation activity, transcription repression activity, transcription release factor activity, histone modification activity, RNA cleavage activity, DNA cleavage activity, DNA integration activity or nucleic acid binding activity. The one or more functional domains may be transcriptional activation domain or a repressor domains.

Activator and repressor domains which may further modulate function may be selected on the basis of species, strength, mechanism, duration, size, or any number of other parameters. Exemplary effector domains include, but are not limited to, a transposase domain, integrase domain, recombinase domain, resolvase domain, invertase domain, protease domain, DNA methyltransferase domain, DNA demethylase domain, histone acetylase domain, histone deacetylases domain, nuclease domain, repressor domain, activator domain, nuclear-localization signal domains, transcription-protein recruiting domain, cellular uptake activity associated domain, nucleic acid binding domain or antibody presentation domain.

In one embodiment, the one or more functional domain may be an APOBEC domain (see e.g., Yang et al., J Genet Genomics. 44(9):423-437 (2017)). APOBEC-catalyzed deamination in single-stranded nucleic acid molecules can be further processed to yield mutations including, but not limited to, insertions or deletions (indels).

Polypeptide Inhibitors

In other related embodiments, the invention includes an isolated peptide inhibitor that inhibits one or more *Enterococcus* sp. proteins or genes or one or more host proteins or genes. In certain embodiments, the inhibitor comprises a variant of the isolated peptide. The variants of the peptides according to the present invention may be (i) one in which one or more of the amino acid residues are substituted with a conserved or non-conserved amino acid residue and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

A peptide inhibitor of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide inhibitor.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

Antibodies

In certain embodiments, the composition comprises an antibody, or fragment thereof, capable of binding to *Enterococcus* sp., or one or more *Enterococcus* sp. or host protein. In one embodiment, the antibody or antibody fragment induces an immune response against *Enterococcus* sp. In one embodiment, the antibody or antibody fragment inhibits the activity of one or more *Enterococcus* sp. or host protein.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic-acted cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H₂L₂) formed of two dimers associated through at least one disulfide bridge.

Vaccine

In the context of the present invention, the term "vaccine" (also referred to as an immunogenic composition) refers to a substance that induces an immune response upon inoculation into a subject. In certain embodiments, the vaccine induces an adaptive immune response. In some instances, the vaccine of the invention can be used to induce an immune response against *Enterococcus* sp., thereby depleting *Enterococcus* sp. and treating or preventing an autoimmune disease or disorder.

In one embodiment, the composition comprises a vaccine, where the vaccine induces an immune response to one or more antigens in a cell, tissue or mammal (e.g., a human). In certain embodiments, the vaccine may comprise an antigen (e.g., a peptide or polypeptide), a nucleic acid encoding an antigen (e.g., an antigen expression vector), a cell expressing or presenting an antigen or cellular component. In particular embodiments the vaccine comprises or encodes all or part of any peptide antigen described herein, or an immunologically functional equivalent thereof. In certain embodiments, the composition comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the composition is conjugated to or comprises an HLA anchor motif amino acids.

Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the peptide vaccine of the invention includes, but is not limited to a peptide mixed with adjuvant substances and a peptide which is introduced together with an APC. The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen peptides. Presenting the peptide can be effected by loading the APC with a polynucleotide (e.g., DNA, RNA) encoding the peptide or loading the APC with the peptide itself.

A vaccine of the present invention may vary in its composition of nucleic acid and/or cellular components. In a non-limiting example, a nucleic encoding an antigen might also be formulated with an adjuvant.

In certain embodiments, the vaccine comprises one or more peptides, polypeptides, or fragments thereof, or nucleic acid molecules (e.g., DNA or RNA) encoding one or more peptides, polypeptides or fragments thereof, of *Enterococcus* sp. Exemplary peptides or polypeptides of *Enterococcus* sp. that may be used include, but is not limited to, Adhesin of collagen, aggregation substance proteins, haemolysin-cytolysin, a-diglycosyl diacylglycerol, endocarditis- and biofilm-associated pili, enterococcal leucine-rich-repeat-containing protein, enterococcal polysaccharide antigen, enterococcal surface protein, gelatinase, methionine sulpoxide reductase AB, sortase A, M16 family metallopeptidase, rRNA methyltransferase, DNA helicase, 30S ribosomal protein S6, DNA gyrase subunit B, GTP-binding protein, ATP synthase, ATP binding protein, ATP-dependent protease, ATP:cob(I)alamin adenosyltransferase, phosphoenolpyruvate-protein phosphotransferase, glutamine ABC transporter ATP-binding protein, ABC transporter permease, phosphoglycerate mutase, vanZ protein, beta-lactamase, ribosomal silencing factor RsfS, Fe-S cluster assembly protein SufD, SAM-dependent methyltransferase, MerR family transcriptional regulator, pyrrolidone-carboxylate peptidase, N-acetyl-D-glucosamine ABC transporter permease, and PTS sugar transporter subunit IIBC.

When a certain peptide or combination of peptides induce an anti-*Enterococcus* sp. immune response upon inoculation into an animal, the peptide or combination of peptides are decided to have anti-*Enterococcus* sp. immunity inducing effect. The induction of the anti-*Enterococcus* sp. immunity by a peptide or combination of peptides can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain peptide or combination of peptides of the invention can be evaluated by presenting the peptide to a T cell by APC, and detecting the induction of CTL. Furthermore, APCs have the effect of activating CD4+ T cells, CD8+ T cells, macrophages, eosinophils and NK cells.

A method for evaluating the inducing action of CTL using dendritic cells (DCs) as APC is well known in the art. DC is a representative APC having the strongest CTL inducing action among APCs. In this method, the peptide or combination of peptides are initially contacted with DC and then this DC is contacted with T cells. Detection of T cells having cytotoxic effects against the cells of interest after the contact with DC shows that the peptide or combination of peptides have an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The peptide or combination of peptides confirmed to possess CTL inducing activity by these methods are peptides having DC activation effect and subsequent CTL inducing activity. Therefore, a peptide or combination of peptides that induce CTL against *Enterococcus* sp. are useful as vaccines to deplete *Enterococcus* sp. thereby treating or preventing an autoimmune disease or disorder. Furthermore, CTL that have acquired cytotoxicity due to presentation of the peptide or combination of peptides by APC can be also used as vaccines to deplete *Enterococcus* sp.

Generally, when using a peptide for cellular immunotherapy, efficiency of the CTL-induction can be increased by combining a plurality of peptides having different structures and contacting them with DC. Therefore, when stimulating DC with protein fragments, it is advantageous to use a mixture of multiple types of fragments.

The induction of anti-*Enterococcus* sp. immunity by a peptide or combination of peptides can be further confirmed by observing the induction of antibody production against anti-*Enterococcus* sp. For example, when antibodies against a peptide or combination of peptides are induced in a laboratory animal immunized with the peptide or combination of peptides, and when *Enterococcus* sp. is depleted in the animal, the peptide or combination of peptides are determined to induce anti-*Enterococcus* sp. immunity.

In certain embodiments, the composition comprises an inactivated or killed *Enterococcus* sp. bacterium. Inactivated/killed generally refers to infectious agents (e.g., bacteria, viruses, other microorganisms or agents) that are not capable of reproducing or causing disease (i.e., avirulent). Inactivated bacterial preparations may be called bacterins. The inactivated/killed agents are able to stimulate an immune response when administered to an animal, in the context of a vaccine composition, for example. In contrast to inactivated vaccines, live vaccines and live attenuated vaccines, for example, are able to replicate and generally do so once they are administered to an animal.

Another type of vaccine, called subunit vaccines, also does not replicate. Subunit vaccines generally contain substantially less than all of a bacterium or virus and, in this way, often may be distinguished from inactivated/killed vaccines. For example, subunit vaccines may contain single or a few recombinant protein antigens from a bacterium or virus. Subunit vaccines may also contain individual structures, like a capsid or capsomere from a virus, for example. Inactivated or killed vaccines generally include more of a bacterium or virus, for example, than does a subunit vaccine. For example, an inactivated vaccine may contain all or substantially all of a virus or bacterium. In one example, entire cultures of bacteria or viruses may be inactivated or killed. In another example, less than all, but still substantial parts of bacteria or viruses may be used in an inactivated/killed vaccine. For example, bacteria may be extracted with a chemical to obtain the cell wall, cell membrane or cell wall plus cell membrane portions that may be used as or in an inactivated/killed vaccine or immune stimulatory composition.

Generally, agents for inclusion in an inactivated or killed vaccine may be grown, purified or semi-purified, inactivated, and then formulated into a vaccine composition. Bacteria may be grown on cell free, serum-free, protein-free, synthetic medium and the like, using commonly known methods for growth of pure bacterial cultures. Often, bacteria are grown in liquid cultures. The bacteria may be purified, semi-purified, and/or concentrated. For example, bacteria grown in liquid culture may be subject to relatively low-speed centrifugation, the culture medium decanted, and the bacterial pellet re-suspended in buffer.

The bacteria may be killed or inactivated using a variety of methods. In one example, the bacteria may be treated with various chemicals for various periods of time to render the agents incapable of replication, but still retaining at least some ability to stimulate an immune response (i.e., immunogenicity) when administered to an animal, Many such agents are known. Example inactivating agents include, but are not limited to, formalin/formaldehyde, ethyleneimine derivatives, ultraviolet radiation or heat, thimerosal and/or β-propiolactone, and others. The infectious agents are generally treated with a concentration of the agent for a length of time and at a temperature to inactivate the bacteria, yet still preserve at least some of the ability of the agent to be immunogenic and stimulate an immune response. Inactivating agents may be removed prior to formulation into compositions for administration to animals.

In certain embodiments, the composition comprises an attenuated *Enterococcus* sp. bacterium. For example, in one embodiment, the bacterium may be temperature-sensitive. In one embodiment, the bacterium may be cold-adapted. In certain aspects, these three features are particularly useful when using live bacteria as a vaccine antigen. In certain instances, compared with an inactivated vaccine, an attenuated vaccine can offer great advantages in activating immune responses in a host. First, as a live replicating bacteria in the host, the attenuated vaccine strain can be readily detected by the immune system, and thereby can activate a wide spectrum of immune responses. Second, since attenuated vaccine strain can replicate in host, they continuously present antigens to the immune system and therefore provides durable immunity and requires less often vaccination or boosters.

An anti-*Enterococcus* sp. immune response can be induced by administering a vaccine of this invention, and the induction of an anti-*Enterococcus* sp. immune response enables treatment and prevention of an autoimmune disease or disorder.

The peptide or combination of peptides of the invention having immunological activity, or a polynucleotide or vector encoding such a peptide or combination of peptides, may be combined with an adjuvant. An adjuvant refers to a compound that enhances the immune response against the peptide or combination of peptides when administered together (or successively) with the peptide having immunological activity. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intravenous, intracerebroventricular, intradermal, intramuscular, or another route of administration. Other contemplated formulations include projected nanoparticles, liposomal preparations, resealed erythrocytes containing the active ingredient, and immunogenic-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In various embodiments, the composition comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intradermal, intrasternal injection, intratumoral, intravenous, intracerebroventricular and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers. In certain embodiments, the formulation may comprise dry particles which comprise the active ingredient and which have a diameter in the range from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. In certain embodiments, dry powder compositions include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain instances having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Treatment Methods

The invention provides a method for treating, or preventing an autoimmune disease or disorder in a subject in need thereof. In certain embodiments, the method comprises reducing the amount or activity Enterococcus sp. in a subject. In certain embodiments, the method comprises reducing, diminishing, or depleting Enterococcus sp. in a subject. For example, in certain embodiments, the method comprises administering to a subject a therapeutic composition which reduces the amount or activity Enterococcus sp in a subject. For example, in certain embodiments, the method comprises administering to a subject an immunotherapeutic composition which induces an immune response against Enterococcus sp.

The therapeutic compounds or compositions of the invention may be administered prophylactically or therapeutically to subjects suffering from or at risk of (or susceptible to) developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Exemplary autoimmune diseases or disorders treated or prevented by way of the method include, but is not limited to SLE, AIH, primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis. In certain embodiments, the compositions and methods of the invention are useful to treat or prevent liver inflammation and cirrhosis.

Administration of the compositions of the invention in a method of treatment can be achieved in a number of different ways, using methods known in the art. In one embodiment, the method of the invention comprises systemic administration of the subject, including for example enteral or parenteral administration. In certain embodiments, the method comprises intradermal delivery of the composition. In another embodiment, the method comprises intravenous delivery of the composition. In some embodiments, the method comprises intramuscular delivery of the composition. In one embodiment, the method comprises subcutaneous delivery of the composition. In one embodiment, the method comprises inhalation of the composition. In one embodiment, the method comprises intranasal delivery of the composition.

It will be appreciated that the composition of the invention may be administered to a subject either alone, or in conjunction with another agent, including for example, one or more antibiotics, which reduces the amount or activity of Enterococcus sp. in the subject. In certain embodiments, the method comprises administering the compositing of the invention in combination with a treatment for an autoimmune disease or disorder, including but not limited to, steroids, nonsteroid drugs (such as ibuprofen or naproxen), immunosuppressive agents (such as azathioprine, methotrexate, cyclophosphamide, calcineurin inhibitors), biologic agents (such as rituximab, eculizumab, belilumab, abatacept), immunomodulatory drugs (such as hydroxychloroquine or intravenous immunoglobulin (IVIG)), plasmapheresis or plasmaexchange.

The compositions useful for practicing the invention may be administered to deliver a dose of from 1 ng/kg/day and 100 mg/kg/day. In one embodiment, the invention envisions administration of a dose which results in a concentration of the compound of the present invention from 10 nM and 10 µM in a mammal.

Typically, dosages which may be administered in a method of the invention to a mammal, such as a human, range in amount from 0.01 µg to about 50 mg per kilogram of body weight of the mammal, while the precise dosage administered will vary depending upon any number of factors, including but not limited to, the type of mammal and type of disease state being treated, the age of the mammal and the route of administration. In certain embodiments, the dosage of the compound will vary from about 0.1 µg to about 10 mg per kilogram of body weight of the mammal. In certain embodiments, the dosage will vary from about 1 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In certain embodiments, administration of an immunogenic composition or vaccine of the present invention may be performed by single administration or boosted by multiple administrations.

When using cells of the invention (e.g., peptide-load antigen presenting cell or peptide-specific IFNγ-secreting CD4+ T cells) as the vaccine, an autoimmune disease or disorder can be treated or prevented, for example, by the ex vivo method. For example, PBMCs of the subject receiving treatment or prevention are collected, contacted ex vivo with an immunotherapeutic agent described elsewhere herein. Following the induction of peptide-load antigen presenting cells or peptide-specific IFNγ-secreting CD4+ T cells, the cells may be administered to the subject. In one embodiment, the cells of the invention can be induced by introducing a vector encoding an immunogenic peptide into them ex vivo. The cells induced in vitro can be cloned prior to administration. By cloning and growing cells having high activity of damaging target cells, cellular immunotherapy can be performed more effectively. Furthermore, cells of the invention isolated in this manner may be used for cellular immunotherapy not only against individuals from whom the cells are derived, but also against similar types of diseases in other individuals.

In certain embodiments, the method comprises administering to the subject an antibiotic that reduces the amount or activity of *Enterococcus* sp. in a subject. The type and dosage of the administered antibiotic will vary widely, depending upon the nature of the autoimmune disease or disorder, the subject's medical history, the frequency of administration, the manner of administration, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In various embodiments, the administered antibiotic is at least one of lipopeptide, fluoroquinolone, ketolide, cephalosporin, amikacin, gentamicin, kanamycin, neomycin, netilmicin, paromomycin, streptomycin, tobramycin, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime cefluprenam, cefoselis, cefozopran, cefpirome, cefquinome, cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, ceftaroline, ceftioxide, cefuracetime, imipenem, primaxin, doripenem, meropenem, ertapenem, flumequine, nalidixic acid, oxolinic acid, piromidic acid pipemidic acid, rosoxacin, ciprofloxacin, enoxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, amoxicillin, ampicillin, bacampicillin, carbenicillin, cloxacillin, dicloxacillin, flucloxacillin, mezlocillin, nafcillin, oxacillin, penicillin g, penicillin v, piperacillin, pivampicillin, pivmecillinam, ticarcillin, sulfamethizole, sulfamethoxazole, sulfisoxazole, trimethoprim-sulfamethoxazole, demeclocycline, doxycycline, minocycline, oxytetracycline, tetracycline, linezolid, clindamycin, metronidazole, vancomycin, vancocin, mycobutin, rifampin, nitrofurantoin, chloramphenicol, or derivatives thereof.

Methods of Diagnosis

In various embodiments, the present invention relates to methods of diagnosing a subject as having, or assessing the risk of a subject for developing, an autoimmune disease or disorder.

In various embodiments, the amount of *Enterococcus* sp. or anti-*Enterococcus* sp. in a sample of a subject is indicative of an autoimmune disease or disorder. In some embodiments, the detection of an increased amount of *Enterococcus* sp., as compared to a control, is used to diagnose the subject as having, or as at risk of developing, an autoimmune disease or disorder. In other embodiments, the detection of an increased amount of anti-*Enterococcus* sp. antibodies in a sample of the subject, as compared to a control, is used to diagnose the subject as having, or as at risk of developing, an autoimmune disease or disorder.

In various embodiments, the detection of *Enterococcus* sp. or anti-*Enterococcus* sp. antibodies is used to assess the progression of an autoimmune disease or disorder, or to assess the efficacy of a treatment method.

In various embodiments, the autoimmune diseases and disorders diagnosed or assessed by way of the present method include, but are not limited to, at least one of: SLE, AIH, primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis. In certain embodiments, the present method can be used to diagnose or assess liver inflammation and cirrhosis.

In various embodiments of the method of the invention, a subject is diagnosed as having, or at risk for developing, an autoimmune disease or disorder when *Enterococcus* sp. or anti-*Enterococcus* sp. antibodies are detected at a level that is increased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, in the biological sample when compared with a comparator control.

In various embodiments of the method of the invention, a subject is diagnosed as having, or at risk for developing, an autoimmune disease or disorder when *Enterococcus* sp. or anti-*Enterococcus* sp. antibodies are detected at a level that is increased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, in the biological sample when compared with a comparator control.

The amount of *Enterococcus* sp. or anti-*Enterococcus* sp. antibodies, can be detected using various methods, including without limitation quantitative PCR or high-throughput sequencing methods. In some embodiments, the amount of *Enterococcus* sp. can be assessed by detecting a bacterial genetic marker. In particular embodiments, the bacterial genetic marker is at least some portion of the 16S rRNA.

In various embodiments, the amount of *Enterococcus* sp. or anti-*Enterococcus* sp. antibodies is compared to a comparator, which may be by way of non-limiting examples, the amount in a subject known to be free of an autoimmune disorder, or a historical norm, or a typical amount of the population of which the subject is a member.

In one embodiment, the method of the invention is a diagnostic assay for diagnosing an autoimmune disease or disorder, by determining the absolute or relative abundance of *Enterococcus* sp. or anti-*Enterococcus* sp. antibodies in a biological sample derived from the subject. In some embodiments, the subject is diagnosed as having an autoimmune disease or disorder when *Enterococcus* sp. or anti-*Enterococcus* sp. antibodies are determined to presented at an increased abundance, relative to a comparator control.

The results of the diagnostic assay can be used alone, or in combination with other information from the subject, or from the biological sample derived from the subject.

In the assay methods of the invention, a test biological sample from a subject is assessed for the amount of *Enterococcus* sp. or anti-*Enterococcus* sp. antibodies. The test biological sample can be an in vitro sample or an in vivo sample. In various embodiments, the subject is a human subject, and may be of any race, sex and age. Representative subjects include those who are suspected of having an autoimmune disease or disorder, those who have been diagnosed with autoimmune disease or disorder, those whose have an autoimmune disease or disorder, those who have had an autoimmune disease or disorder, those who at risk of a recurrence of autoimmune disease or disorder, those who at risk of a flare of an autoimmune disease or disorder, and those who are at risk of developing an autoimmune disease or disorder.

In some embodiments, the method further comprises effectuating a treatment regimen on a subject diagnosed with an autoimmune disease or disorder. For example, in one embodiment, the method comprises diagnosing a subject with an autoimmune disease or disorder based upon the detected level of *Enterococcus* sp. or anti-*Enterococcus* sp. antibodies, and administering a treatment regimen to the subject to treat the autoimmune disease or disorder. In one embodiment, the treatment regimen comprises administering to the subject one or more immunosuppressive agents. In one embodiment, the treatment regimen comprises administering to the subject one or more nonsteroidal anti-inflammatory drugs (NSAIDs). In one embodiment, the treatment regimen comprises administering to the subject one or more immunoglobulins.

In some embodiments, the test sample is prepared from a biological sample obtained from the subject. In some instances, a heterogeneous population of microbes will be present in the biological samples. Enrichment of a microbial population for microbes (e.g., bacteria) bound by secretory antibody (e.g., IgA, IgM) may be accomplished using separation technique. For example, microbes of interest may be enriched by separation the microbes of interest from the initial population using affinity separation techniques. Techniques for affinity separation may include magnetic separation using magnetic beads conjugated with an affinity reagent, affinity chromatography, "panning" with an affinity reagent attached to a solid matrix, e.g. plate, or other convenient technique. Other techniques providing separation include fluorescence activated cell sorting, which can have varying degrees of sophistication, such as multiple color channels, low angle and obtuse light scattering detecting channels, impedance channels, etc. One example of an affinity reagent useful in the methods of the invention is an antibody, such as anti-species antibody or anti-isotype (e.g., anti-IgA, anti-IgM) antibody. The details of the preparation of such antibodies and their suitability for use as affinity reagents are well-known to those skilled in the art. In some embodiments, labeled antibodies are used as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type.

In various embodiments, the initial population of microbes is contacted with one or more affinity reagent(s) and incubated for a period of time sufficient to permit the affinity reagent to specifically bind to its target. The microbes in the contacted population that become labeled by the affinity reagent are selected for by any convenient affinity separation technique, e.g. as described elsewhere herein or as known in the art. Compositions highly enriched for a microbe of interest (e.g., secretory antibody-bound bacteria) are achieved in this manner. The affinity enriched microbes will be about 70%, about 75%, about 80%, about 85% about 90%, about 95% or more of the composition. In other words, the enriched composition can be a substantially pure composition of the microbes of interest.

In one embodiment, the test sample is a sample containing at least a fragment of a bacterial nucleic acid. The term, "fragment," as used herein, indicates that the portion of a nucleic acid (e.g., DNA, RNA) that is sufficient to identify it as comprising a bacterial nucleic acid.

In some embodiments, the test sample is prepared from a biological sample obtained from the subject. The biological sample can be a sample from any source which contains a bacterial nucleic acid (e.g., DNA, RNA), such as a bodily fluid or fecal sample, or a combination thereof. A biological sample can be obtained by any suitable method. In some embodiments, a biological sample containing bacterial DNA is used. In other embodiments, a biological sample containing bacterial RNA is used. The biological sample can be used as the test sample; alternatively, the biological sample can be processed to enhance access to nucleic acids, or copies of nucleic acids, and the processed biological sample can then be used as the test sample. For example, in various embodiments, nucleic acid is prepared from a biological sample, for use in the methods. Alternatively or in addition, if desired, an amplification method can be used to amplify nucleic acids comprising all or a fragment of an RNA or DNA in a biological sample, for use as the test sample in the assessment of the presence, absence and proportion of particular types of bacteria present in the sample.

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of nucleic acid from a particular type of bacteria can be determined by hybridization of nucleic acid to a nucleic acid probe. A "nucleic acid probe," as used herein, can be a DNA probe or an RNA probe.

The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target RNA or DNA. The hybridization sample is maintained under conditions which are sufficient to allow specific hybridization of the nucleic acid probe to RNA or DNA. Specific hybridization can be performed under high stringency conditions or moderate stringency conditions, as appropriate. In one embodiment, the hybridization conditions for specific hybridization are high stringency. More than one nucleic acid probe can also be used concurrently in this method. Specific hybridization of any one of the nucleic acid probes is indicative of the presence of the particular type of bacteria of interest, as described herein.

In Northern analysis (see Current Protocols in Molecular Biology, Ausubel, F. et al., eds., John Wiley & Sons, supra), the hybridization methods described above are used to identify the presence of a sequence of interest in an RNA, such as unprocessed, partially processed or fully processed rRNA. For Northern analysis, a test sample comprising RNA is prepared from a biological sample from the subject by appropriate means. Specific hybridization of a nucleic acid probe, as described above, to RNA from the biological sample is indicative of the presence of the particular type of bacteria of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a particular bacterial nucleic acid sequence. Hybridization of the PNA probe to a nucleic acid sequence is indicative of the presence of the particular type of bacteria of interest.

Direct sequence analysis can also be used to detect a bacterial nucleic acid of interest. A sample comprising DNA or RNA can be used, and PCR or other appropriate methods can be used to amplify all or a fragment of the nucleic acid, and/or its flanking sequences, if desired. The bacterial nucleic acid, or a fragment thereof, is determined, using standard methods.

In another embodiment, arrays of oligonucleotide probes that are complementary to target microbial nucleic acid sequences can be used to detect and identify microbial nucleic acids. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for particular bacterial nucleic acids. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target bacterial nucleic acid sequence is amplified by well-known amplification techniques, e.g., PCR. Typically, this involves the use of primer sequences that are complementary to the target sequence. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect microbial nucleic acids of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE)

(1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as E. coli mutS protein (see, for example, U.S. Pat. No. 5,459,039); Luminex xMAP™ technology; high-throughput sequencing (HTS) (2011, Gundry and Vijg, Mutat Res, doi:10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi:10.1038/nmeth.f 330; 2011, Rothberg et al., Nature 475:348-352) and/or allele-specific PCR, for example. These and other methods can be used to identify the presence of one or more microbial nucleic acids of interest, in a biological sample derived from a subject. In various embodiments of the invention, the methods of assessing a biological sample for the presence or absence of a particular nucleic acid sequence, as described herein, are used to aid in the diagnosis of an autoimmune disease or disorder in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a fresh or fixed biological sample.

Routine methods also can be used to extract DNA from a biological sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. In one embodiment, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, in certain instances, the nucleic acid probe is labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, at least 15 nucleotides, or at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Southern blotting, levels of the target nucleic acid can be determined.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. In one embodiment, the detection of the duplex is done using at least one primer directed to the target nucleic acid. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

The expression "specifically hybridizing in stringent conditions" refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. In one embodiment, the Tm for the amplification step is in the range of about 59° C. to about 72° C. In one embodiment, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1997, eds Current Protocols in Molecular Biology).

In one embodiment, the process for determining the quantitative and qualitative profile according to the present invention is characterized in that the amplifications are real-time amplifications performed using a labeled probe, such as a labeled hydrolysis-probe, capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. In one embodiment, the Tm for any one of the hydrolysis-probes of the present invention is in the range of about 67° C. to about 70° C. In one embodiment, the Tm applied for any one of the hydrolysis-probes of the present invention is about 67° C.

In one embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a target bacterial nucleic acid, and more particularly the primer includes 12 or more contiguous nucleotides substantially complementary to the sequence flanking the nucleic acid sequence of interest. In one embodiment, a primer featured in the invention includes a nucleotide sequence sufficiently complementary to hybridize to a nucleic acid sequence of about 12 to 25 nucleotides. In one embodiment, the primer differs by no more than 1, 2, or 3 nucleotides from the target flanking nucleotide sequence. In another aspect, the length of the primer can vary in length. In one embodiment, the length of the primer can be about 15 to 28 nucleotides in length (e.g., 16, 17, 18, 19, 20, 21, 22, 23, 24, 25, 26, or 27 nucleotides in length).

In one embodiment, the method comprises detecting the level of anti-*Enterococcus* sp. antibodies in a test sample of a subject. In various embodiments, the test sample is a biological sample (e.g., fluid, tissue, cell, cellular component, etc.) of the subject. In some embodiments, the biological sample is blood, serum, plasma, saliva, sweat, stool, vaginal fluid, or urine. A biological sample can be obtained by appropriate methods, such as, by way of examples, blood draw, fluid draw, or biopsy. A biological sample can be used as the test sample; alternatively, a biological sample can be processed to enhance access to the antibodies and the processed biological sample can then be used as the test sample.

The methods of detecting an anti-*Enterococcus* sp. antibody may be carried out using any assay or methodology known in the art. In various embodiments of the invention, methods of measuring an anti-*Enterococcus* sp. antibody in a biological sample include, but are not limited to, an immunochromatography assay, an immunodot assay, a Luminex assay, an ELISA assay, an ELISPOT assay, a protein microarray assay, a ligand-receptor binding assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

The present invention also pertains to kits useful in the methods of the invention. Such kits comprise components useful in any of the methods described herein, including for example, hybridization probes or primers (e.g., labeled probes or primers), reagents for detection of labeled molecules, means for amplification of nucleic acids, means for analyzing a nucleic acid sequence, and instructional materials. For example, in one embodiment, the kit comprises components useful for analysis of a bacterial nucleic acid of interest present in a biological sample obtained from a subject. In one embodiment, the kit comprises components for detecting one or more of the bacterial nucleic acids of interest present in a biological sample derived from a subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Spontaneous Translocation of a Gut Pathobiont in Autoimmunity

Despite multiple associations between the microbiota and immune diseases, its role in autoimmunity is poorly understood. It is demonstrated herein that a gut pathobiont, *E. gallinarum*, translocates to tissues including the liver in a spontaneous model of autoimmunity. A single antibiotic that prevents mortality in this model, suppressed growth of *E. gallinarum* in tissues, pathogenic autoantibodies and T cells. Hepatocyte-commensal cocultures demonstrated induction of autoimmune-promoting factors. Translocation in monocolonized and autoimmune-prone mice induced autoantibodies and mortality, which could be prevented with an intramuscular vaccine targeting this pathobiont. *E. gallinarum*-specific DNA could be recovered from liver biopsies of autoimmune patients, suggesting similar processes in humans. Collectively, these data indicate that a human pathobiont translocates spontaneously to promote autoimmunity in genetically predisposed hosts, broadening the understanding of autoimmune host-microbiota interactions. Further information regarding the experiments and data presented herein can be found in Manfredo-Vieira et al., (2018, The Enemy Lies Within: Spontaneous Translocation of a Gut Pathobiont Drives Autoimmunity, Science) which is incorporated by reference herein in its entirety.

The materials and methods used in these experiments are now described.

Animals 6-week-old male (NZWxBXSB)$F_1$ mice and C57BL/6J mice were used in this study except if noted otherwise. (NZWxBXSB)$F_1$ were bred by mating NZW/LaJ females with BXSB/MpJ males obtained from Jackson Laboratory (Bar Harbor, Me., USA). Parental littermates of (NZWxBXSB)$F_1$ were randomly mixed with littermates from other parental cages 21 days after birth to equilibrate the microbiomes from different cages and parental origin. All mice were maintained in a specific-pathogen-free environment. (NZWxBXSB)$F_1$ mice were provided with water and a standard laboratory diet ad libitum (2018 Harlan Teklad, South Easton, Mass., USA). They were supplied with hardwood chips as bedding and were housed in a temperature-controlled, air-conditioned room on a 12-hr light-dark cycle. Germ-free (GF) C57BL/6 mice were kept under sterile conditions in CBC's (Class Biologically Clean, Madison, Wis., USA) Quad flexible film isolators (Softwall), exposed to a 12-hr light/dark cycle and provided standard, autoclaved tap water and mouse chow (2018S Harlan Teklad, South Easton, Mass., USA) ad libitum. To exclude a Th17 bias, a PCR for segmented filamentous bacteria (SFB) was performed on fecal DNA from all mice involving Th17 studies. Fecal SFB detection at 6-8 weeks of age that correlates with ileal SFB colonization was performed as described (Barman et al., 2008, Infect Immun, 76, 907-915; Kriegel et al., 2011, Proc Natl Acad Sci USA, 108, 11548-11553). All Th17 data was derived from SFB-negative animals.

Antibiotic Treatment and Gavage with Vancomycin-Resistant *E. gallinarum*.

Mice were cohoused for 3 to 4 weeks before antibiotic treatment to allow for equilibration of the microbiota. Single antibiotic or broad-spectrum antibiotic administration consisted of metronidazole (1 g/liter; Fisher Scientific), neomycin (1 g/liter; Fisher Scientific), ampicillin (1 g/liter; Sigma) and vancomycin (0.5 g/liter; Acros Organics) in the drinking water for up to 22 weeks or a targeted regiment for 2 weeks and then replaced with regular water for the duration of the experiment. For broad-spectrum antibiotic experiments (vancomycin, ampicillin, metronidazole, and neomycin combined), sweetener (Equal, 4 g/L) was added to both the antibiotics and control water due to the metallic taste of metronidazole. Twenty-four hours after cessation of antibiotic water, mice were administered $1\times10^6$ CFUs of vancomycin-resistant *E. gallinarum* via oral gavage, isolated from liver tissue of a vancomycin-treated mouse that continued to show signs of autoimmune disease (high-level resistance was confirmed by vanC gene PCR). *E. gallinarum* was grown at 37° C. in Gifu Anaerobic Broth (HIMEDIA Laboratories) to early stationary phase under anaerobic conditions (82% $N_2$, 15% $CO_2$, 3% $H_2$ by volume) in an anaerobic chamber and diluted in PBS to $10^7$ CFUs.

Bacterial Lysates and RNA Purification.

*Enterococcus gallinarum* and *Enterococcus faecalis* were grown at 37° C. in Gifu Anaerobic Broth (HIMEDIA Laboratories, Mumbai, India) whereas *Bacteroides thetaiotaomicron* was grown in Gut Microbiota Medium (Goodman et al., 2011, Proc Natl Acad Sci USA, 108, 6252-6257) to early stationary phase under anaerobic conditions. Final cultures were centrifuged and pellets were resuspended in 0.1M PBS (Corning). Bacteria were placed in RNAse/DNAse-free, reinforced 2 mL bead mill tubes (VWR) containing 0.1 mm mini-bead beater glass mill beads (BioSpec Products) followed by 3 cycles of 1 minute bead beating and 3 minutes on ice. Next, the mixture was centrifugated at 1000×g for 8 minutes and supernatants were used in the assays. For *E. gallinarum, E. faecalis* and *B. thetaiotaomicron* RNA purification, bacterial RNA was purified using Qiagen RNAprotect Bacteria Reagent and RNeasy Protect Bacteria Kits according to the manufacturer's instructions.

Histopathology

Samples were obtained at autopsy and fixed in 10% neutral formalin, and histological sections were stained with hematoxylin and eosin (H&E) and scored in a blinded fashion. Glomerulonephritis was scored on a scale of 0-4 based on the intensity and extent of histopathological changes (Klopfleisch, 2013, BMC Vet Res, 9, 123). A grade of 0 was given to kidneys without glomerular lesions; grade 1 consisted of minimal thickening of the mesangium; grade 2 contained noticeable increases in both mesangial and glomerular cellularity; grade 3 was characterized by the preceding conditions with superimposed inflammatory exudates and capsular adhesions; and grade 4 consisted of obliterated glomerular architecture in greater than 70% of glomeruli. Twenty glomeruli within one area were graded according to this classification and used to calculate the mean glomerular histopathological score for each mouse, and those scores were used to calculate mean scores for each experimental cohort.

Livers of mice were dissected and fixed in formalin at the time of euthanasia. After paraffin embedding, sectioning, and H&E staining, the revised Knodell scoring system was used to evaluate degree of liver damage (Knodell et al., 1981, Hepatology, 1, 431-435). In brief, 0, no inflammation or spotty necrosis; 1, piecemeal necrosis or confluent necrosis (less than 10%); 2, confluent necrosis (10%-50%); 3, large area of confluent necrosis (more than 50%) with/without bridging necrosis; and 4, large area of confluent necrosis (more than 75%) with/without bridging necrosis. Injury scoring was performed in a blinded fashion.

Myocardial involvement was evaluated based on a grading scale previously applied to this autoimmune model (Akkerman et al., 2004, Autoimmunity, 37, 445-451) using a scale from 1 to 4 in ascending severity. In brief, a grade of 1 indicated one single area of necrosis or scarring; 2 indicated several areas of necrosis or fibrosis; 3 indicated focal areas of necrosis and fibrosis; and 4 represented full thickness myocardial infarct. Scoring was performed in a blinded fashion.

Enzyme-Linked Immunosorbent Assays (ELISAs)

Serum antibodies specific for dsDNA and b2GPI were determined using standardized ELISAs (anti-dsDNA antibody, Abcam; and, Mouse/Rat Apolipoprotein H Antibody, R&D Systems; respectively). Anti-RNA was determined by ELISA using defined positive controls (Human/Mouse RNA Polymerase II Antibody, R&D systems). Anti-ERV gp70 ICs and ERV gp70 protein were determined by OD450 signal comparisons (Evans et al., 1990, J Virol, 64, 6176-6183). For anti-dsDNA ELISAs, DNA-BIND™ (Corning) plates were coated with 100 µg/ml salmon sperm DNA (Fisher Scientific) and blocked in 0.1M PBS, 3.0% BSA, 5.0% FBS. The serum was diluted 1:1000 for the assay and incubated for 1 hour at 37° C. Wells were washed and incubated for 1 hour at 37° C. with rabbit anti-mouse IgG (Fisher Scientific) conjugated to HRP and developed with TMB substrate solution. 2M sulfuric acid (Sigma) solution was used to stop development. The concentration of anti-dsDNA was determined by reading the absorbance at 450 nm/570 nm reference.

For anti-RNA ELISAs, DNA-BIND™ (Corning) plates were coated with 5 mg/ml yeast RNA (Ambion) and blocked in 0.1M PBS, 0.05% Tween-20, 5.0% FBS. The serum was diluted 1:1000 for the assay and incubated for 1 hour at 37° C. Wells were washed and incubated for 1 hour at 37° C. with rabbit anti-mouse IgG (Fisher Scientific) conjugated to HRP and developed with TMB substrate solution. 2M sulfuric acid (Sigma) solution was used to stop development. The concentration of anti-RNA IgG was determined by reading the absorbance at 450 nm/570 nm reference.

For anti-b2GPI ELISAs, Corning® 96-well EIA/RIA easy Wash™ clear flat-bottom polystyrene high-bind microplates were coated with 1 mg/ml recombinant b2GPI/ApoH (R&D Systems) and blocked in Pierce Protein-Free (PBS) Blocking Buffer (Thermo Scientific). The serum was diluted 1:100 for the assay and incubated at room temperature for 2 hours on a shaker. Wells were washed and incubated while shaking for 30 minutes at room temperature with goat anti-mouse IgG (Fisher Scientific) conjugated to HRP and developed with TMB substrate solution. 2M sulfuric acid (Sigma) solution was used to stop development. The concentration of anti-b2GPI was determined by reading the absorbance at 450 nm/650 nm reference.

For ERV gp70 protein ELISAs, Corning® 96-well clear flat-bottom polystyrene high-bind microplates were coated with 4 ng/ml mouse IgM anti-gp70 murine leukemia virus (MLV) envelope monoclonal antibody and blocked in 0.1M PBS, 2% BSA. The serum was diluted 1:100 for the assay and incubated for 1 hour at 37° C. Wells were washed and incubated while shaking for 30 minutes at 37° C. with 4 ng/ml rat IgG2a anti-gp70 MLV envelope monoclonal antibody. Wells were washed and incubated for 30 minutes at 37° C. with rabbit anti-rat IgG (Fisher Scientific) conjugated to HRP and developed with TMB substrate solution. 2M sulfuric acid (Sigma) solution was used to stop development. The concentration of anti-ERV gp70 was determined by reading the absorbance at a wavelength of 450 nm with a correction wavelength of 900 nm.

For anti-ERV gp70 immune complex (IC) ELISAs, Corning® 96-well clear flat-bottom polystyrene high-bind microplates were coated with 2 ng/ml rat IgG2a anti-gp70 MLV envelope monoclonal antibody and blocked in 0.1M PBS, 3% BSA and 5% FBS. Precipitation of ERV gp70 ICs was done as described (Maruyama et al., 1983, J Immunol, 130, 740-746). In brief, mouse serum was diluted 1:10 in 0.1M PBS containing 10% PEG with a molecular weight of 6,000 (Sigma) and was incubated for one hour at 4° C. The diluted serum was centrifuged at 2,500 g for 30 minutes and the precipitates, containing gp70 ICs with bound gp70, were washed with 0.1M PBS containing 10% PEG 6,000. The gp70 ICs were resuspended in 0.1M PBS containing 1% BSA at a dilution of 1:100. Wells were incubated with the diluted precipitates for 1 hour at 37° C. Wells were washed and incubated for 1 hour at 37° C. with rabbit anti-mouse IgG (Thermo Scientific) conjugated to HRP and developed with TMB substrate solution. 2M sulfuric acid (Sigma) solution was used to stop development. The concentration of anti-ERV gp70 ICs was determined by reading the absorbance at a wavelength of 450 nm with a correction wavelength of 900 nm.

Small Intestinal RNA Sequencing

Germ-free mice were gavaged with $1 \times 10^6$ CFU of E. gallinarum (EG), E. faecalis (EF), B. thetaiotaomicron (BT) or vehicle (CTRL). Mice were euthanized 8 hours later and dissected. The ileum was immediately flushed with RNA-later (RNA stabilization reagent, Qiagen). Samples were individually saved in tubes containing 500 mL of RNA-later at 4° C. and processed the following day. RNA was isolated using the RNAeasy plus mini kit (Qiagen) according to the manufacturer's instructions. RNA libraries were prepared in accordance with the Illumina kit protocol after poly-A selection and sequenced on the HiSeq 2500 platform in a stranded paired-end manner. The generated fastq files were trimmed using custom Perl scripts. The trimmed reads were aligned to the mm10 genome using TopHat2 (Trapnell et al., 2009, Bioinformatics, 25, 1105-1111). The transcript abundance estimation and differential gene expression was done using cuffdiff (Trapnell et al., 2013, Nat Biotechnol, 31, 46-53). The data was visualized using R and cummerbund (Haas et al., 2013, Nat Protoc, 8, 1494-1512).

*Enterococcus gallinarum* Genome Sequencing

Bacterial DNA samples were prepared in quadruplicates. *E. gallinarum* DNA was purified using UltraClean Microbial DNA Isolation kit (MO BIO Laboratories Inc.) according to manufacturer's instructions. *E. gallinarum* DNA samples were quantified using Quant-iT PicoGreen dsDNA kit (Molecular Probes). The library was built using Nextera XT DNA Library Prep kit (Illumina Inc.) according to the manufacturer's instructions. Briefly, transposome was used to tagment *E. gallinarum* gDNA and the DNA fragments were tagged with adapter sequences and then the tagmented DNA were amplified. In the next step, beads were used to purify the library DNA and to remove short library fragments. The quality of the libraries was checked using a High Sensitivity DNA chip on an Agilent Technology 2100 Bioanalyzer. Then, DNA samples were normalized to ensure more equal library representation in the pooled library. The four libraries were pooled and combined equal volumes of normalized libraries in a single tube. The four samples were sequenced on a HiSeq 2500 system (Illumina Inc.) and assembled individually using the SPAdes assembler, as each sample's data consisted of approx. 500× coverage of the genome (merging the datasets could introduce high-depth artifactual contig breaks). SPAdes was run twice on each dataset, once with options "-t 20 --careful" and a second time adding the "--plasmid" option, to maximize the potential of assembling any plasmids present in the sample Bankevich et al., 2012, J Comput Biol, 19, 455-477). The two assemblies for each sample were compared to each other, but no additional sequences were found from the plasmid assembly. Each of the four sample assemblies (run without --plasmid) were filtered for contigs shorter than 2,000 bp, resulting in assemblies with 27, 27, 29 and 32 contigs and 3.631-3.635 MB in total length. They were then cross-compared for contiguity using BLAT, and the assembly with 27 contigs and 3,633,913 bp was chosen as the final result. A complete list of all *E. gallinarum* genes is summarized in FIG. 24.

Proteinuria 24 week-old (NZWxBXSB)$F_1$ mice were tested semi-quantitatively for proteinuria with albumin test strips (Multistix10SG Siemens) once every other week when spot urine was collected. Urine was placed in test strips and evaluated after 60 seconds for negative, trace, 30 mg/dL (+), 100 mg/dL (++), 300 mg/dL (+++) and 2000 mg/dL or more (++++).

In Vivo Gut Permeability Test with FITC-Dextran 14-week-old mice were weighed and fasted for 4 hours prior to oral FITC-Dextran (4 kDa, Sigma) administration. A total concentration of 250 mg/kg body weight was administered via gavage. After 4 hours of the administration, blood samples were collected through the tail vein and serum was placed in a fluorescence plate reader to determine the concentration by fluorescence excitation at 495 nm/519 nm reference.

Assessment of Bacterial Translocation and Tissue Burden

14-, 16- and 18-week-old mice underwent sterile laparotomy and nose, mouth, small intestine (luminal and adherent fractions), mesenteric veins, mesenteric lymph nodes (MLN), liver and spleen were aseptically collected in BBL Mycoflask Thioglycollate (Fluid) Prepared Media (BD Diagnostic Systems) and incubated for 72 hours in anaerobic conditions at 37° C. Gifu Media Agar plates were streaked with the content from the BBL Mycoflask Thioglycollate and incubated for 48 hours in an anaerobic chamber at 37° C. Colony Formation Units (CFU) were counted and concentration determined per milligram of tissue. Single colonies were grown in Gifu anaerobic media for 48 hours in an anaerobic chamber at 37° C. and aliquots from each sample were collected and centrifuge for 10 minutes at 10000×g. DNA was extracted from bacterial pellets using DNeasy Blood and Tissue kit (Qiagen) and submitted to PCR amplification of the 16S region and Sanger sequencing. In addition, purified DNA was used for eubacterial, *Enterococcus* genus and *Enterococcus gallinarum* PCR assays.

*E. gallinarum*, *E. Faecalis* and *B. thetaiotaomicron* Monocolonization Experiments Germ-free C57BL/6 mice were colonized by a single oral gavage with 1×10$^6$ CFU of *E. gallinarum*, *E. faecalis* or *B. thetaiotaomicron*. Animals were sacrificed at day 28. Mice were assessed for bacterial translocation and burden as described above. The relative abundance of *E. gallinarum* was determined by species-specific PCR at the indicated time points after isolation of fecal DNA.

In Vitro Hepatocyte Experiments

Human and mouse hepatocytes were provided by the Yale Liver Center. Human hepatocytes were maintained in HMM medium (Lonza) plus 100 nM insulin (Sigma), 100 nM dexamethasone (PromoKine), 50 µg/ml gentamicin (Sigma) and 50 g/ml SPA antibiotic-antimyotic (Gibco). Human hepatocytes were plated on Corning® BioCoat™ Collagen I plate (Corning). For sandwich culture, human hepatocytes were overlaid with 1:25 Matrigel (Corning) in cold maintenance HMM medium. Mouse hepatocytes were maintained in Corning® Specialty Media Hepato-STIM Hepatocyte Culture Medium plus 50 µg/ml gentamicin (Sigma) and 50 µg/ml SPA antibiotic-antimyotic (Gibco). Mouse hepatocytes were plated on Corning® BioCoat™ Collagen I plate (Corning). For sandwich culture, murine hepatocytes were overlaid with 1:25 Matrigel (Corning) in cold maintenance medium. Hepatocytes were challenged with 100 ng/ml *E. coli* LPS (ecLPS; InvivoGen), 5 mg/ml imiquimod (InvivoGen), 10 mg/ml *E. gallinarum* lysates, 10 mg/ml *E. gallinarum* RNA, 10 mg/ml *E. gallinarum* lysates RNAse treated, 10 mg/ml *E. gallinarum* lysates RNAse and DNAse treated, 10 mg/ml *E. faecalis* lysates, 10 mg/ml *E. faecalis* RNA, 10 mg/ml *B. thetaiotaomicron* lysates or 10 mg/ml *B. thetaiotaomicron* RNA.

Isolation of Splenic Dendritic Cells

Total dendritic cells were isolated from 18-week-old (NZWxBXSB)$F_1$ mice using the Miltenyi Biotec kit. Briefly, spleens were cut into small pieces and placed in a 6-cm petri-dish with 2 mg/mL of Collagenase D (containing 10 mM Hepes-NaOH, pH 7.4, 150 mM NaCl, 5 mM KCl, 1 mM $MgCl_2$, 1.8 mM $CaCl_2$) and incubated for 30 minutes at 37° C. on a shaker. Subsequently, the remaining spleen fragments were gently filtered through a 70 µm cell strainer using a plunger. Cells were collected in a 15-mL falcon tube and washed twice with PBS. Afterwards, the cells were resuspended in buffer containing phosphate-buffered saline (PBS), pH 7.2, 0.5% bovine serum albumin (BSA), and 2 mM EDTA. Next, pan-DCs were purified according to the manufacturer's protocol (Miltenyi Biotec, cat. #130-100-875). Isolated pan-DCs (1×10$^5$ cells per well) were cultured with *E. gallinarum* (10 mg/ml) or *E. gallinarum* RNA (10 mg/ml) on 96-wells flat-bottom cell culture plates. Parallel cultures maintained without stimuli were used as controls.

Quantitative Reverse Transcription PCR (RT-qPCR) Analysis

RNA was isolated from hepatocytes, dendritic cells or ileum using the RNAeasy plus mini kit (Qiagen) according to the manufacturer's instructions. cDNA was generated using the QuantiTect Reverse Transcription Kit (Qiagen). RT-PCR was performed on cDNA using TaqMan primers and probes in combination with TaqMan PCR Master Mix (Applied Biosystems), and reactions were run on an RT-PCR system (QuantiStudio 6 Flex; Applied Biosystems). Gene expression is displayed as fold increase and normalized to Hprt (for hepatocytes) or GAPDH (for dendritic cells and ileum).

For *E. gallinarum* qPCRs, DNA was isolated from human liver biopsies using QIAamp DNA FFPE tissue kit (Qiagen) according to the manufacturer's instructions. DNA isolated from liver biopsies was quantified on a Nanodrop 1000 (Thermo Scientific) and then run for quantitative PCR assays on the QuantiStudio 6 Flex (Applied Biosystems) with the Power SYBR Green Master Mix (Applied Biosystems). For gel-PCR reactions, thermal cycler (Applied Biosystems Veriti) was programmed to run with the following conditions:

*Enterococcus* genus: 94° C. for 5 minutes followed by 30 cycles of 94° C. for 10 seconds, 60° C. for 30 seconds and 72° C. for 30 seconds. Afterwards, samples were kept at 72° C. for 5 minutes. The following primer sequences were used: ENT-fwd (5'-TACTGACAAACCATTCATGATG-3' (SEQ ID NO: 1), ENT-rev (5'-AACTTCGTCAC-CAACGCGAAC-3' (SEQ ID NO: 2), IC-fwd (5'-TCTCGAGCTCTGTACATGTCC-3' (SEQ ID NO: 3)) and IC-rev (5'-GTTCTAGAGGTACCGGTTGTT-3' (SEQ ID NO: 4));

*Enterococcus gallinarum:* 95° C. for 4 minutes followed by 50 cycles of 95° C. for 30 seconds, 55° C. for 60 seconds and 72° C. for 60 seconds. Afterwards, samples were kept at 72° C. for 7 minutes. The following primer sequences were used: EG-fwd (5'-TTACTTGCTGATTTTGATTCG-3' (SEQ ID NO: 5)) and EG-rev (5'-TGAATTCTTCTTT-GAAATCAG-3' (SEQ ID NO: 6));

Eubacterial: 94° C. for 5 minutes followed by 30 cycles of 94° C. for 10 seconds, 60° C. for 30 seconds and 72° C. for 30 seconds. Afterwards, samples were kept at 72° C. for 5 minutes. The following primer sequences were used: EUB1114-fwd (5'-CGGCAACGAGCGCAACCC-3' (SEQ ID NO: 7)) and EUB1221-rev (5'-CCAT-TGTAGCACGTGTGTAGCC-3' (SEQ ID NO: 8)).

The primer sequences above were used for PCR and qPCR.

Multiple Soluble Analytes Immunoassays

Cytokine levels were determined from culture supernatants using LEGENDplex™ (BioLegend), a bead-based immunoassay. The preformed mouse T helper cytokine panel was used. Experimental samples were assayed with the standards and controls included with the kit according to the manufacturer's instructions. Data was collected using a BD Fortessa Flow Cytometer. Data analysis was carried out with the LEGENDplex (7.0) analysis software.

Leukocyte Isolation from Lamina Propria

Mice were euthanized and small intestines (SI) were collected and placed in iced cold cHBSS (HBSS containing 5% fetal bovine serum and 1% penicillin-streptomycin). The lumen of the intestine was flushed with ice-cold cHBSS using a 10-ml syringe and 21 G needle. Peyer's patches were removed and intestines were cut longitudinally in a 10-cm petri dish containing PBS. Intestines were transferred to a 50-mL Falcon containing cold cPBS (PBS containing 2% fetal bovine serum and 1% penicillin-streptomycin) and mixed on a vortexer for 5 seconds. Tissue was washed two times with 20 mL of cPBS.

Next, the small intestine was processed using the following digestion steps. SI was transferred to a 50-mL falcon containing 20 ml of cPBS at room temperature. 200 uL of 0.5 M EDTA was added to the tube. Tubes were sealed and placed horizontally in a shaker (200 rpm, 25 min, 37° C.). After incubation, tubes were vortex and supernatant was discarded. The solution was replaced with 20 mL of cold cPBS and vortex for 5 seconds on maximum speed. The procedure was repeated two more times using 20 mL of cold cHBSS. After the last washing step, the tissue was placed in a 5-cm Petri dish at room temperature and 7 mL of cHBSS containing collagenase D (2 mg/mL, Roche) and DNAse I (0.1 mg/mL, Roche) was added. Next, SI was minced into small pieces and incubated in a shaker (70 rpm) for 30 minutes at 37° C. Samples were filtered through a 100-µm strainer and washed in the Petri dish with 10 mL of cHBSS (50 ml Falcon, room temperature). Next, 10 ml of cHBSS were added to the strainer and the suspension transferred to a new tube through a 40 µm strainer (at room temperature) and centrifugated (500×g) for 5 minutes at 4° C., then washed one more time with 20 mL of cHBSS by centrifugating the mixture at a speed of 500×g for 5 minutes at 4° C. Finally, the cells were resuspended in 1 mL of media.

Intracellular Cytokine Detection and Flow Cytometry

For direct ex vivo intracellular cytokine detection, cells isolated from small intestinal lamina propria, MLN or spleen were immediately treated with GolgiStop (BD Bioscience) and surface-stained in FACS buffer (PBS, 2% bovine serum albumin, 0.2 mg of sodium azide, 2 mM EDTA) for 30 minutes in the dark at room temperature with fluorescently conjugated antibodies specific for CD3, CD4, CD11b, CD11c, CD44, CD62L, CD19, CD45, CD45R (B220), CXCR5, GITR, IL-17, IFN-g, Ly6C, NK1.1, PDCA-1, PD-1 and PSGL-1. After staining for surface antigens, some B cells and T cells were stained for intracellular cytokines using intracellular cytokine fixation buffer (eBioscience) and fluorescently conjugated antibodies specific for IL-17, IFN-g and FoxP3 (eBioscience) for 30 minutes in the dark at room temperature. Cell viability was assessed with Zombie NIR Fixable Viability Kit (BioLegend).

For the vancomycin in vitro assays, total cells from MLN were culture in a 96-well plate with vancomycin (8 mg/mL; Acros), anti-CD3 (0.6 mg/mL; BioLegend) and anti-CD28 (1 mg/mL; Biolegend) for 48 hours and GolgiStop (1 mL/mL; BD Bioscience) during the last 4 hours of in vitro culture. In vitro samples were stained as described above. All samples were collected using an LSR II flow cytometer (Becton Dickinson). All flow cytometry data were analyzed by FlowJo version 9.7 (Tree Star).

*Salmonella typhimurium* Infection Experiments

*S. typhimurium* strain derivative of SL1344 with a clean deletion on spiA gene was provided (Spano et al., 2011, Proc Natl Acad Sci USA, 108, 18418-18423). The attenuated strain does not contain an active SPI-2-encoded type III secretion system and was used throughout the in vivo experiments. Strain SL1344 is naturally resistant to streptomycin, which was used for selection. Bacteria were cultured in LB growth medium (Difco) containing streptomycin (100 mg/mL; EMD Millipore). *E. gallinarum* was cultured in Gifu anaerobic media without antibiotics. (NZWxBXSB) $F_1$ mice were treated with broad-spectrum antibiotics (vancomycin, ampicillin, neomycin and metronidazole) for 2 weeks in the drinking water. Broad-spectrum antibiotics were exchanged for streptomycin (5 g/l) in the drinking water at the end of the 2-week period. 24 hours later, mice were gavage with $1\times10^6$ CFU of *S. typhimurium*, *E. gallinarum* or vehicle and continued with streptomycin treatment in the drinking water. After one month, sera were collected for assessment of autoantibodies and gut barrier leakiness using FITC-dextran. Mice were euthanized 24 hours later for translocation assays as described above.

AhR Antagonist Experiments (NZWxBXSB)$F_1$ mice were treated with broad-spectrum antibiotics (vancomycin, ampicillin, neomycin and metronidazole) from 10 weeks to 14 weeks of age. 24 hours later mice were gavaged with *E. gallinarum* every week for 4 weeks. Subsequently, mice were injected i.p. with 300 mg of CH223191 (a selective AhR antagonist; Sigma-Aldrich) or mock 5 days a week for the entire duration of the experiment starting at 14 weeks of age. After 4 weeks of bacterial gavage and AhR antagonist treatment, sera were collected for assessment of autoantibodies and mice were euthanized for FACS analysis of MLN Th17 cells.

*E. gallinarum* Culture and Vaccine Formulation

Vancomycin-resistant *E. gallinarum* (with resistance confirmed by vanC gene PCR (Patel et al., 1997, J Clin Microbiol, 35, 703-707) and in vitro testing) was grown in a broth (pH 7.3±0.1) containing 10 g/L of peptic digest of animal tissue, 3 g/L of papaic digest of soyabean meal, 10 g/L of proteose peptone, 13.5 g/L of digested serum, 5 g/L of yeast extract, 2.2 g/L of beef extract, 1.2 g/L of liver extract, 3 g/L of dextrose, 2.5 g/L of potassium dihydrogen phosphate, 3 g/L of sodium chloride, 5 g/L of soluble starch, 0.3 g/L of L-cysteine hydrochloride and 0.3 g/L of sodium thioglycollate.

*E. gallinarum* was centrifuged for 10 minutes at 5,000× g, and washed 2 times with Milli-Q water in the same condition. Next, *E. gallinarum* was suspended in endotoxin-free water and heat-killed for 10 minutes at 110° C. prior to lyophilization. 100 mg of dried *E. gallinarum* was equivalent to $10^6$ colony-forming units (CFU) prior to being heat-killed. Each *E. gallinarum* vaccination dose was administrated once a week for two weeks and contained 100 mg of heat-killed *E. gallinarum*, 0.125 mg of aluminum phosphate, 100 mg of polysorbate 80, 295 mg of succinate and MilliQ water.

Human Subjects and Microbiota Samples

Exclusion criteria for the longitudinal patient cohorts used for fecal and serum studies were as follows: active infection, viral hepatitis, human immunodeficiency virus or acquired immunodeficiency syndrome, use of antibiotics or probiotic use within three months, major gastrointestinal surgery in the last 5 years, gastrointestinal bleeding history, inflammatory bowel disease, bulimia or anorexia nervosa, morbid obesity, uncontrolled diabetes mellitus, or malignancy in the past year. Subjects with SLE and healthy controls completed up to three study visits for blood and stool collections and a detailed medical and dietary history as part of ongoing microbiome studies (ClinicalTrials.gov identifier NCT02394964). Peripheral blood was collected by venipuncture and serum stored at −80° C. Stool samples were collected by subjects at home in sterile containers and shipped overnight on ice to the laboratory, at which time they were aliquoted and stored at −80° C. 100 to 300 mg of human stool was combined with 1 ml MoBio Bead Solution and 1 mm ceramic beads (BioSpec) and bead beat twice for 1 minute with a rest on ice between each beating. Samples were centrifuged and supernatant was transferred to a MoBio Garnet Bead tube, heated for 10 minutes at 65° C., followed by 10 minutes for 95° C., then processed per the MoBio Power Soil DNA Isolation Kit protocol.

Liver biopsies were obtained retrospectively from subjects with SLE, AIH or non-AIH-related cirrhosis (chronic hepatitis B or C). Table 1 summarizes clinical and histopathology details. All control liver biopsies were sterilely obtained from subjects who were organ donors for orthotopic liver transplants with thoroughly screened, healthy livers following the UNOS protocol (United Network for Organ Sharing). Absolute contraindications were followed per published literature (D'Alessandro et al., 1991, Transplant Proc, 23, 1536-1537). All cadaveric liver tissues were histologically unremarkable pre-transplantation. Samples were sterilely handled for 16S rDNA sequencing or species- and genus-specific PCRs as above for assessment of *Enterococcus* genus and *E. gallinarum* DNA, respectively.

TABLE 1

Clinical and histopathologic features of patients who underwent liver biopsies. The table summarizes the major clinical features of patients with liver biopsies used for microbiome studies shown in FIG. 6C-FIG. 6E. The three patient groups were systemic lupus erythematosus (SLE) patients who underwent liver biopsies for abnormal liver function tests of unclear etiology, autoimmune hepatitis (AIH) patients, and cirrhosis patients with liver disease unrelated to AIH (non-AIH cirrhosis group). Age and sex as well as the main clinical features are listed for all groups. AIH patient information includes also if patients are in remission versus flaring, if newly diagnosed and untreated, and major comorbidities. Non-AIH cirrhosis cases were all due to chronic viral hepatitis, either hepatitis B or C, with liver pathology showing stage 4 fibrosis except for CIR02.

| Patient Group | Age (years) | Sex | Clinical Features | Liver Biopsy |
|---|---|---|---|---|
| SLE | | | | |
| SLE01 | 44 | F | Glomerulonephritis (class V lupus nephritis), arthritis, pericarditis, ANA titer 1:640, dsDNA+ | Chronic hepatitis with mild portal and lobular activity, portal and focal periportal fibrosis (stage 2/4), moderate macrovesicular steatosis |
| SLE02 | 53 | F | Proteinuria, hair loss, urticaria, Raynaud's, ANA titer 1:640 | Lymphoplasmacytic portal inflammation with mild interface activity (grade 2/4), mild portal and pericellular firbrosis (stage 1-2/4), moderate macrovesicular steatosis |
| SLE03 | 71 | F | Polyarthritis, myositis, Raynaud's, ANA titer 1:2560 | Chronic hepatitis with mild interface activity, portal and periportal fibrosis, mild macrovesicular steatosis |
| AIH | | | | |
| AIH01 | 10 | M | AIH in remission (on azathioprine, corticosteroids, IVIG), common variable immunedeficiency, lichen planus | Features of autoimmune hepatitis with minimal activity, fibrosis stage 3/4 |

TABLE 1-continued

Clinical and histopathologic features of patients who underwent liver biopsies. The table summarizes the major clinical features of patients with liver biopsies used for microbiome studies shown in FIG. 6C-FIG. 6E. The three patient groups were systemic lupus erythematosus (SLE) patients who underwent liver biopsies for abnormal liver function tests of unclear etiology, autoimmune hepatitis (AIH) patients, and cirrhosis patients with liver disease unrelated to AIH (non-AIH cirrhosis group). Age and sex as well as the main clinical features are listed for all groups. AIH patient information includes also if patients are in remission versus flaring, if newly diagnosed and untreated, and major comorbidities. Non-AIH cirrhosis cases were all due to chronic viral hepatitis, either hepatitis B or C, with liver pathology showing stage 4 fibrosis except for CIR02.

| Patient Group | Age (years) | Sex | Clinical Features | Liver Biopsy |
|---|---|---|---|---|
| AIH02 | 32 | F | AIH in flare (newly diagnosed, untreated), autoimmune polyglandular syndrome type I, pancreatitis, panhypopituitarism, pernicious anemia, premature ovarian failure, vitiligo, cholelithiasis, deep vein thrombosis | Feature of autoimmune hepatitis with moderate to marked activity with plasma cells, fibrosis stage 3/4 |
| AIH03 | 51 | F | AIH in flare (newly diagnosed, untreated), papillary throid carcinoma, Sjorgen's syndrome | Features of autoimmune hepatitis with minimal activity, fibrosis stage 1/4 |
| AIH04 | 25 | F | AIH in remission (on 6-mercaptopurine, corticosteroids), Crohn's disease, endometriosis | Features of cirrhosis and autoimmune hepatitis with mild inflammation, fibrosis stage 4/4 |
| AIH05 | 21 | F | AIH in flare (newly diagnosed, untreated), autoimmune polyglandular syndrome type I, hypothroidism, pernicious anemia, hypoparathyroidism | Features of autoimmune hepatitis with minimal activity, stage 1/4 |
| Non-AIH Cirrhosis | | | | |
| CIR01 | 53 | M | Chronic hepatitis C | Cirrhosis, fibrosis stage 4/4 |
| CIR02 | 32 | M | Chronic hepatitis C, rectal myosarcoma | Fibrosis stage 2/4 |
| CIR03 | 42 | M | Chronic hepatitis B | Cirrhosis, fibrosis stage 4/4 |
| CIR04 | 27 | M | Chronic hepatitis C, X-linked hyper IgM syndrome | Cirrhosis, fibrosis stage 4/4 |
| CIR05 | 64 | M | Chronic hepatitis C | Cirrhosis, fibrosis stage 4/4 |

Fecal Mouse Microbiota Sampling

Fresh fecal pellets were collected sterilely from (NZWxBXSB)$F_1$ mice at the same time of the day and then placed immediately on dry ice before transfer into −80° C. Mice were mixed across experimental groups before the start of antibiotic treatments to mitigate cage bias. Pellets were first taken before antibiotic treatment at 6 weeks of age to determine the baseline microbiome across multiple cages and parental origins. Pellets were also collected every other week post-treatment for 16S rDNA sequencing as detailed below. Fecal DNA was isolated using the MoBio PowerSoil DNA Isolation kit and processed for V4 16S rDNA sequencing on the Illumina MiSeq platform as below.

16S rDNA High-Throughput Sequencing

DNA isolation from microbiota samples was performed as above. The V4 region of the 16S rDNA was PCR amplified, normalized, pooled, and sequenced using the Illumina MiSeq with 2×250 bp paired-end reads as described (Kozich et al., 2013, Appl Environ Microbiol, 79, 5112-5120). Analysis of 16S sequencing reads was performed as described (Cullen et al., 2015, Science, 347, 170-175) with the following minor modifications: QIIME analysis was performed with version 1.8 and a quality score cutoff of 30. Mouse 16S rDNA reads were filtered to remove single operational taxonomic units (OTUs) and OTUs were rarefied to a depth of 4,000 sequences per sample. Human liver 16S OTUs representing less than 0.01% of total abundance were excluded from further analysis. Due to low reads per sample in the healthy human liver samples these samples were not rarefied.

Immunofluorescence Studies

Intestinal samples were fixed for 4 hours in paraformaldehyde, L-lysine pH 7.4 and $NaIO_4$ (PLP buffer). They were then washed, dehydrated in 20% sucrose overnight and included in OCT compound (Sakura). 5 μm cryosections were rehydrated, blocked with 0.1M Tris-HCl pH 7.4, 2% FBS, 0.3% Triton X-100 for 30 minutes and stained with the following antibodies: anti-mouse PLVAP (clone MECA32, BD Pharmingen, 1:100), polyclonal anti-CLDN2 (Abcam, 1:50), polyclonal anti-CLDN3 (clone Z23.JM, Invitrogen, 1:100), polyclonal anti-CLDN5 (clone Z43.JK, Invitrogen, 1:100), anti-ZO1 (clone ZMD.436, Invitrogen, 1:50), anti-mouse JAM-A (Abcam, 1:50), anti-mouse VE-cadherin (Abcam, 1:50), anti-occludin (clone OC-3F10, Invitrogen, 1:100), anti-mouse CD31 (clone P2B1, Abcam, 1:100), anti-mouse CD34 (clone ICO-115, Abcam, 1:100), anti-cingulin (Abcam, 1:50), anti-mouse LYVE1 (clone ALY7, Novus Biologicals, 1:50), anti-mouse β-catenin (clone 12F7, BioLegend, 1:100). Primary antibodies were mixed and then incubated overnight at 4° C. Slides were then rinsed 3× with PBS for 5 minutes before incubating with the appropriate species-specific fluorophore-conjugated secondary antibody/mix (1:600 for Cy2 or Cy3, 1:300 for Cy5). After another washing step (3×PBS for 5 minutes), some panels were subsequently stained for F-actin using an AlexaFluor-350 phalloidin (Invitrogen, 1:100) or AlexaFluor-647 phalloidin (Cell Signaling Technologies, 1:100), other slides were counterstained with 4',6-diamidin-2-fenilindolo (DAPI) before imaging. Finally, slides were mounted using coverslips and Prolong anti-fading mounting medium (Invitrogen).

Confocal microscopy was performed on a Leica TCS SP5 laser confocal scanner mounted on a Leica DMI 6000B inverted microscope equipped with motorized stage. Violet (405-nm laser 6 diode), blue (488-nm argon laser), yellow (561-nm laser diode) and red (633-nm laser diode) laser lines have been used for excitation. All images were acquired with a HCX PL APO 40× (NA 1.25) oil immersion objective. Leica LAS AF was used for all acquisitions. ImageJ software package or Imaris (Bitplane) were used for image analysis and quantification of fluorescence.

Fluorescence In Situ Hybridization (FISH)

Bacterial in situ hybridization experiments were carried out on mesenteric lymph node and liver samples. Briefly, tissues were fixed for 4 hours in paraformaldehyde, L-lysine pH 7.4 and $NaIO_4$ (PLP buffer). They were then washed, dehydrated in 20% sucrose overnight and embedded in OCT compound (Sakura). 5 μm cryosections were rehydrated and incubated with 20 μl of hybridization buffer (0.02 M Tris, 0.9 M NaCl, 0.05% SDS and 20% formamide, pH 7.5) with 0.5 ng/mL of *E. gallinarum* (EGA141) (Wellinghausen et al., 2007, J Clin Microbiol 45, 3424-3426) and eubacterial control (EUB338) (Wellinghausen et al., 2007, J Clin Microbiol 45, 3424-3426) oligonucleotide probe (Biomers.net). The hybridization samples were incubated for 2 hours at 46° C. in a humid chamber. Next, samples were washed with distilled water and pre-warmed with post-hybridization buffer (0.02 M Tris, 0.215 M NaCl, 0.025 M EDTA and 0.05% SDS, pH 7.5) for 5 minutes at 46° C. Samples were rinsed with distilled water and air-dried. Air-dried samples received antifade mountant with DAPI (Molecular Probes) and coverslip slides were placed on top. Lastly, slides were analyzed by confocal microscopy on a Leica TCS SP5 laser confocal scanner mounted on a Leica DMI 6000B inverted microscope equipped with motorized stage microscopy with a FITC (absorption wavelength, 494 nm; emission wavelength, 518 nm) and Cy3 (absorption wavelength, 552 nm; emission wavelength, 570 nm) filter. The following FISH probe sequences were used: EUB338, all bacteria 16S rRNA GCTGCCTCCCGTAGGAGT (SEQ ID NO: 9) on Cy3, and EGA141, *E. gallinarum* 23S rRNA ATTCACAACTGTGTAACATCCTAT (SEQ ID NO: 10) on Cy2 (FITC).

Fecal Calprotectin and Albumin Assays

Fecal calprotectin and albumin levels were measured in a single frozen stool sample from all subjects.

For calprotectin, Legend Max™ ELISA kit (BioLegend) was used. Stool samples were aliquoted into pre-weighed bead-containing tubes and stored at −80° C. until sample preparation. 100 mg of stool samples were diluted with 1 ml Tris pH 7.4 followed by bead-beating for 5 seconds. Samples were then spun down at 10,000×g and 4° C. for 10 minutes. The supernatant was carefully transferred to a new microcentrifuge tube avoiding the pellet. The supernatant was centrifuged again using the same settings as above. The resulting supernatant was transferred to a new tube and diluted 1:20 with dilution buffer supplied in the Legend Max™ ELISA kit. Experimental samples were assayed with the standards and controls included with the kit according to the manufacturer's instructions.

For albumin, stool samples were aliquoted into pre-weighed bead-containing tubes and stored at −80° C. until sample preparation. 100 mg of stool samples were diluted with dilution buffer containing 1 ml 50 mM Tris, pH 7.4, 0.14 M NaCl, 1% bovine serum albumin, 0.05% Tween 20 followed by bead-beating for 5 seconds. Samples were then spun down at 10,000×g and 4° C. for 10 minutes. The supernatant was carefully transferred to a new microcentrifuge tube avoiding the pellet. The supernatant was centrifuged again using the same settings as above. The resulting supernatant was transferred to a new tube and diluted 1:20 with dilution buffer, as described, and analyzed by enzyme-linked immunosorbent assay using human albumin (Cat. No. E80-129) The Human Albumin and Calprotectin ELISA Quantification Sets (Bethyl Laboratories) were run according to the manufacturer's instructions.

Anti-*E. gallinarum* Serum IgG and IgA ELISA

Corning® 96-well EIA/RIA easy Wash™ clear flat-bottom polystyrene high bind microplates were coated with 20 mg/ml of *E. gallinarum* lysates and blocked in Pierce Protein-Free Blocking Buffer (Thermo Scientific). The serum was diluted 1:100 for the assay and incubated at room temperature for 2 h on a shaker. All wells were washed and incubated while shaking for 30 minutes at room temperature with goat anti-human IgG or IgA (Fisher Scientific) conjugated to HRP and developed with TMB substrate solution. 2M sulfuric acid (Sigma) solution was used to stop the reaction. The concentration of anti-*E. gallinarum* lysate IgG or IgA or anti-*E. gallinarum* RNA IgG or IgA was determined by reading the absorbance at 450 nm/650 nm reference.

Statistical Analysis

Statistical analysis was carried out with GraphPad Prism (7.01). All data are presented as means±SE. An unpaired Student's t-test was used to evaluate the difference between two groups. Correlation and regression curves were analyzed using Pearson's correlation coefficient; for more than two groups, one-way ANOVA was used. The differences in autoantibodies levels (anti-dsDNA, anti-RNA, anti-b2GPI), *E. gallinarum* antibodies and cytokine levels were assessed by repeated measures two-way ANOVA. A probability value of <0.05 was considered significant. If a significant difference was recognized, a Bonferroni multiple comparison test was performed. For 16S rDNA analysis, differences in the relative abundance of individual taxa between defined groups were tested for significance using the "group_significance" algorithm, implemented within QIIME. Tests were performed using the non-parametric Kruskal-Wallis one-way analysis of variance, generating a Benjamini-Hochberg false-discovery rate (FDR)-corrected p-value. Taxa with an average abundance of <1% across the entire sample set were removed from such analyses. 16S rDNA data was further analysed using linear discriminant analysis effect size (LEfSe) (Segata et al., 2011, Genome Biol, 12, R60).

The results of these experiments are now described.

Figures 1F, 1G, 1H, 1I, 1J, 1K, 1L, 1M, 1N:
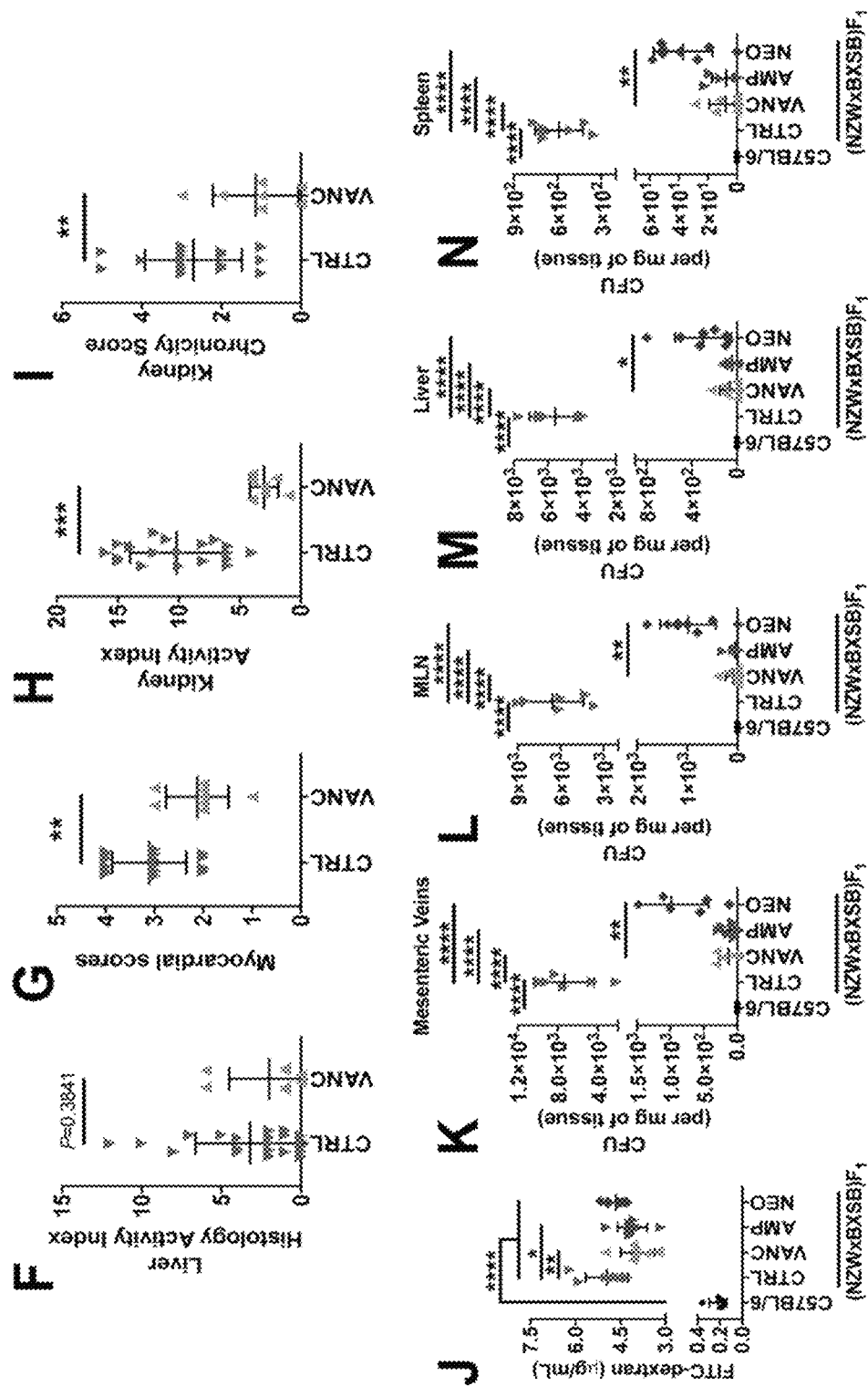
(FIG. 1J) Serum levels of orally administered FITC-dextran as an indicator of gut barrier leakiness (*$P=0.0148$, $P=0.0064$ and **$P<0.0001$, ANOVA followed by the Bonferroni and Student t test). Cultures of tissues from 16-week-old mice showed a selective growth of *E. gallinarum* in the mesenteric veins (FIG. 1K), MLN (FIG. 1L), liver (FIG. 1M), and at 18 weeks of age, also in spleen (FIG. 1N) (*$P<0.05$, $P<0.002$ and *$P<0.0001$, ANOVA followed by the Bonferroni and Student t test). In all cases, suppression of growth was significantly higher in VANC—compare to NEO-treated animals (*$P=0.0337$ and **$P<0.005$, Student t test).
Figures 2A, 2B:
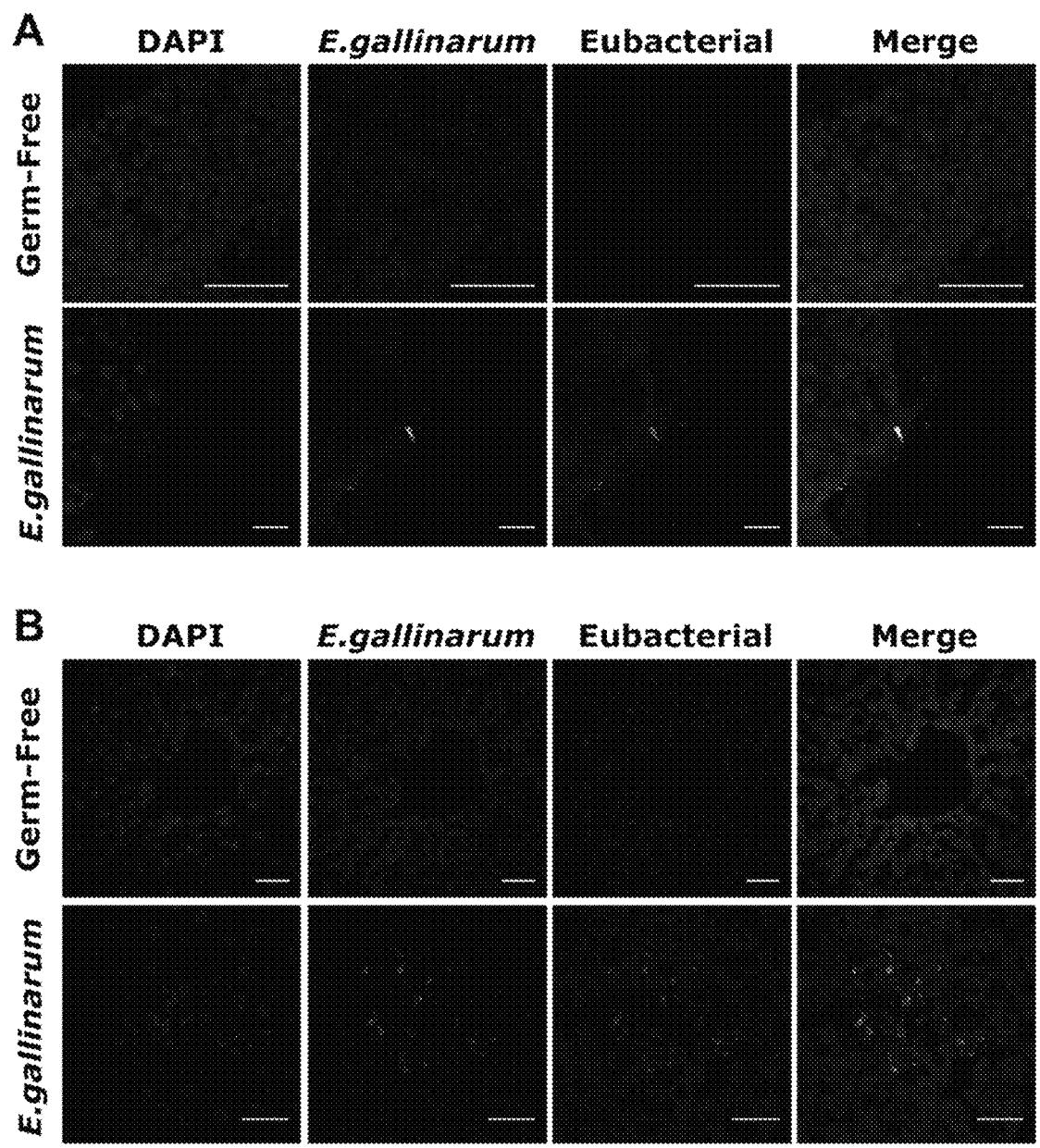
FIG. 2A and FIG. 2B, depicts the results of example experiments illustrating *E. gallinarum* colonization of mesenteric lymph nodes and liver. An *E. gallinarum*-specific FISH probe detects *E. gallinarum* in (FIG. 2A) MLN (Scale bars: 20 µm) and (FIG. 2B) liver (Scale bars: 30 µm) of *E. gallinarum*-monocolonized mice 3 weeks after colonization in comparison to germ-free mice. Shown is one representative section from one mouse each out of multiple sections with *E. gallinarum* signals within the tissues, also representative of three mice in total.
Figures 11A, 11B, 11C, 11D, 11E:
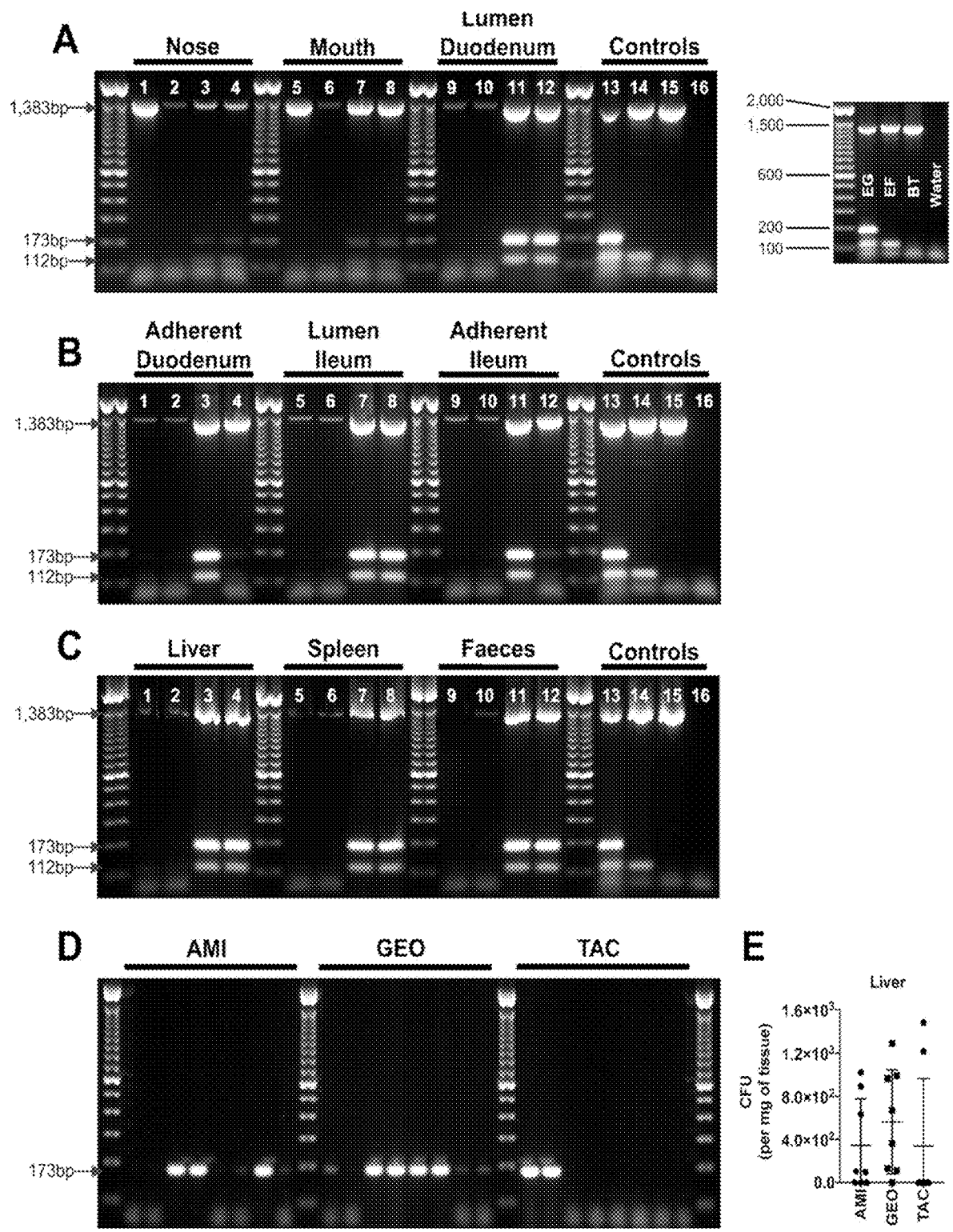
FIG. 11A through FIG. 11E, depicts the results of example experiments demonstrating the detection of *E. gallinarum* by PCR in faecal samples, mucosal tissues, and internal organs from (NZWxBXSB)F$_1$ mice at different animal facilities after culture of samples for 72 hours in growth medium. Nasal and oral swabs, adherent and luminal mucosal tissues from the gastrointestinal tract, tissues from internal organs (liver, spleen), and faecal pellets were harvested from (NZWxBXSB)$F_1$ at 16 weeks of age after control water or broad-spectrum antibiotics (ABX; 0.5 g/L of vancomycin, 1.0 g/L ampicillin, 1.0 g/L metronidazole and 1.0 g/L neomycin) in the drinking water for 8 weeks as detailed in FIG. 8. All samples were first cultured for 72 hours in thioglycollate medium before DNA was purified for PCR specific for eubacteria, Enterococcus genus and E. gallinarum. Product sizes are 1,383 bp for eubacteria (EUB), 112 bp for Enterococcus and 173 bp for E. gallinarum.

First, it was tested if the phenotype in the (NZWxBXSB) $F_1$ hybrid model is modified by altering the gut microbial communities using different orally applied antibiotics (vancomycin, ampicillin, metronidazole, and neomycin, respectively). Mortality, lupus-related autoantibodies, and autoimmune manifestations were prevented by oral vancomycin or ampicillin suggesting involvement of gram-positive pathobionts (FIG. 1A-FIG. 1I). Besides anti-dsDNA and -RNA autoantibodies (FIG. 1B and FIG. 1C), anti-$β_2$GPI, hepatic and serum ERV gp70, and anti-ERV gp70 immune complexes (ICs) were all suppressed as well by vancomycin (FIG. 7). Uptake of orally fed FITC-dextran into the systemic circulation indicated a functionally impaired gut barrier in the hybrid mice compared to non-autoimmune C57BL/6 mice, which was only slightly affected by oral antibiotics (FIG. 1J). Consequently, detection of marked bacterial growth in the mesenteric veins, followed by MLN and liver, at late stages also in the spleen (FIG. 1K-FIG. 1N) was observed. Translocation was profoundly suppressed by either antibiotic that prevented mortality, but only to a lesser degree by neomycin that did not alter clinical outcomes (FIG. 1K-FIG. 1N). Growth of bacteria in the kidney, however, was not detected suggesting that colonization of different organs follows a particular tropism (data not shown; n=15 kidneys cultured anaerobically at 18 weeks of age with no growth after 5 days of culture). Full-length 16S rDNA sequencing of single colonies from aerobic and anaerobic MLN, liver and spleen cultures revealed that *Enterococcus gallinarum*, a gram-positive, anaerobic gut commensal, found in murine and human hosts, is the main species in 82% of isolates that translocate to mesenteric veins in (NZWxBXSB)F$_1$ hybrid mice. *E. gallinarum* could also be visualized in situ in MLNs and livers using FISH (FIG. 2). Non-autoimmune mice showed no bacterial growth consistent with the notion that spontaneous translocation along the gut-liver axis is unique to the autoimmune-prone host. Taxa identified by longitudinal faecal 16S rDNA sequencing revealed the *Enterococcus* genus only enriched in some faecal samples (FIG. 8A-FIG. 8C and FIG. 9). In addition, a highly sensitive species-specific PCR did not pick up *E. gallinarum* DNA in human or murine stool samples except for monocolonized mice that carry a high burden (FIG. 10A-FIG. 10D). However, faecal or mucosal tissue culture followed by species-specific PCR revealed consistently *E. gallinarum* not only in the faeces but also in its primary niche of the small intestine (both the adherent and luminal fractions) as well as livers (FIG. 11A-FIG. 11C). Of note, *E. gallinarum* colonization of livers was also observed in two other animal facilities (FIG. 11D), suggesting translocation is independent from a specific microbiota.

Figure 3A:
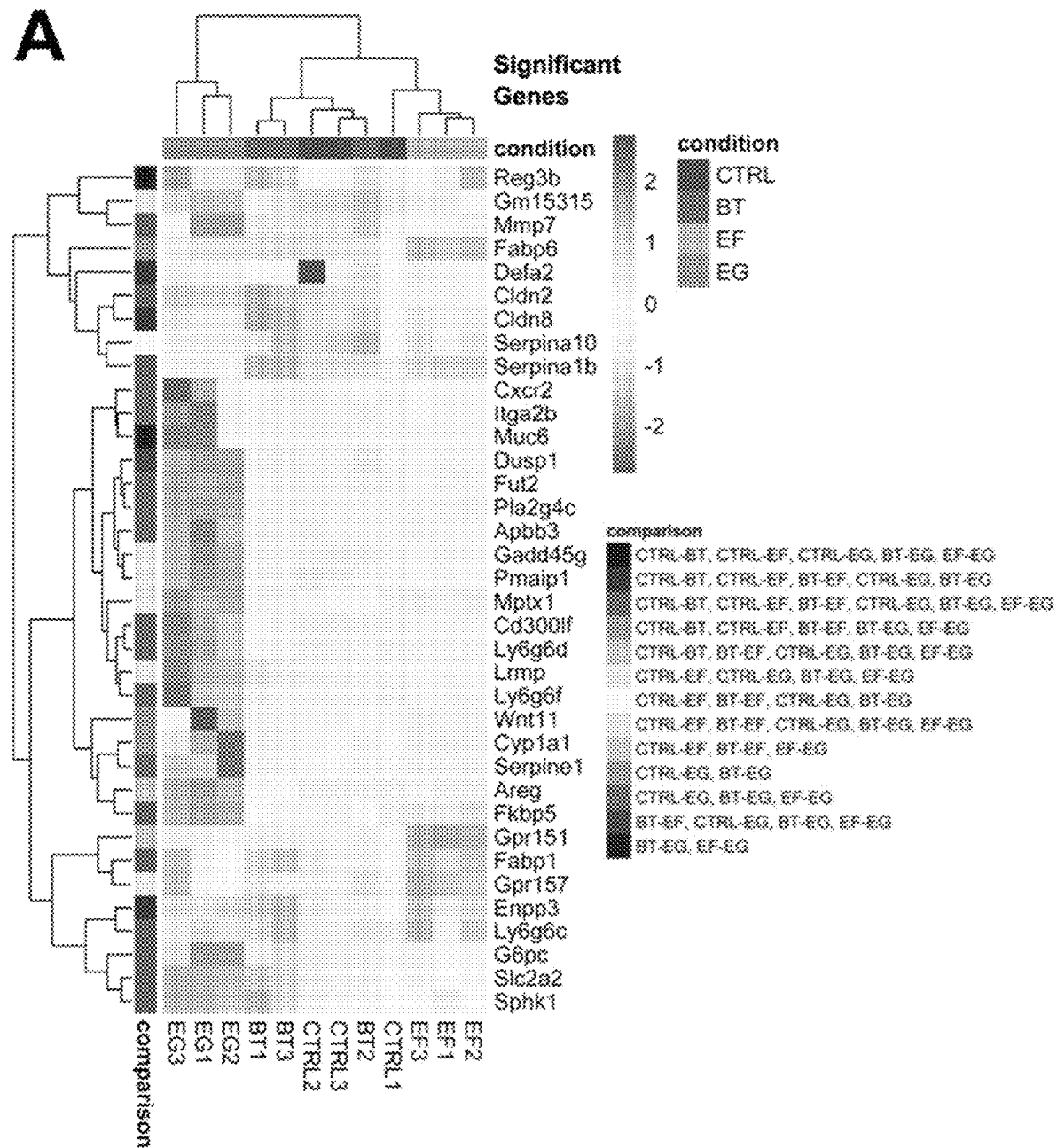
FIG. 3A through FIG. 3O, depicts the results of example experiments illustrating RNA expression profiling and plasmacytoid dendritic cell frequencies of small intestinal lamina propria from germ-free mice monocolonized with *E. gallinarum*, *E. faecalis* or *B. thetaiotaomicron*. Germ-free C57BL/6 mice were monocolonized with *E. gallinarum*, *E. faecalis* or *B. thetaiotaomicron* for RNA-seq and FACS analyses of the small intestine.
Figures 3B, 3C, 3D, 3E, 3F, 3G, 3H, 3I, 3J, 3K, 3L, 3M:
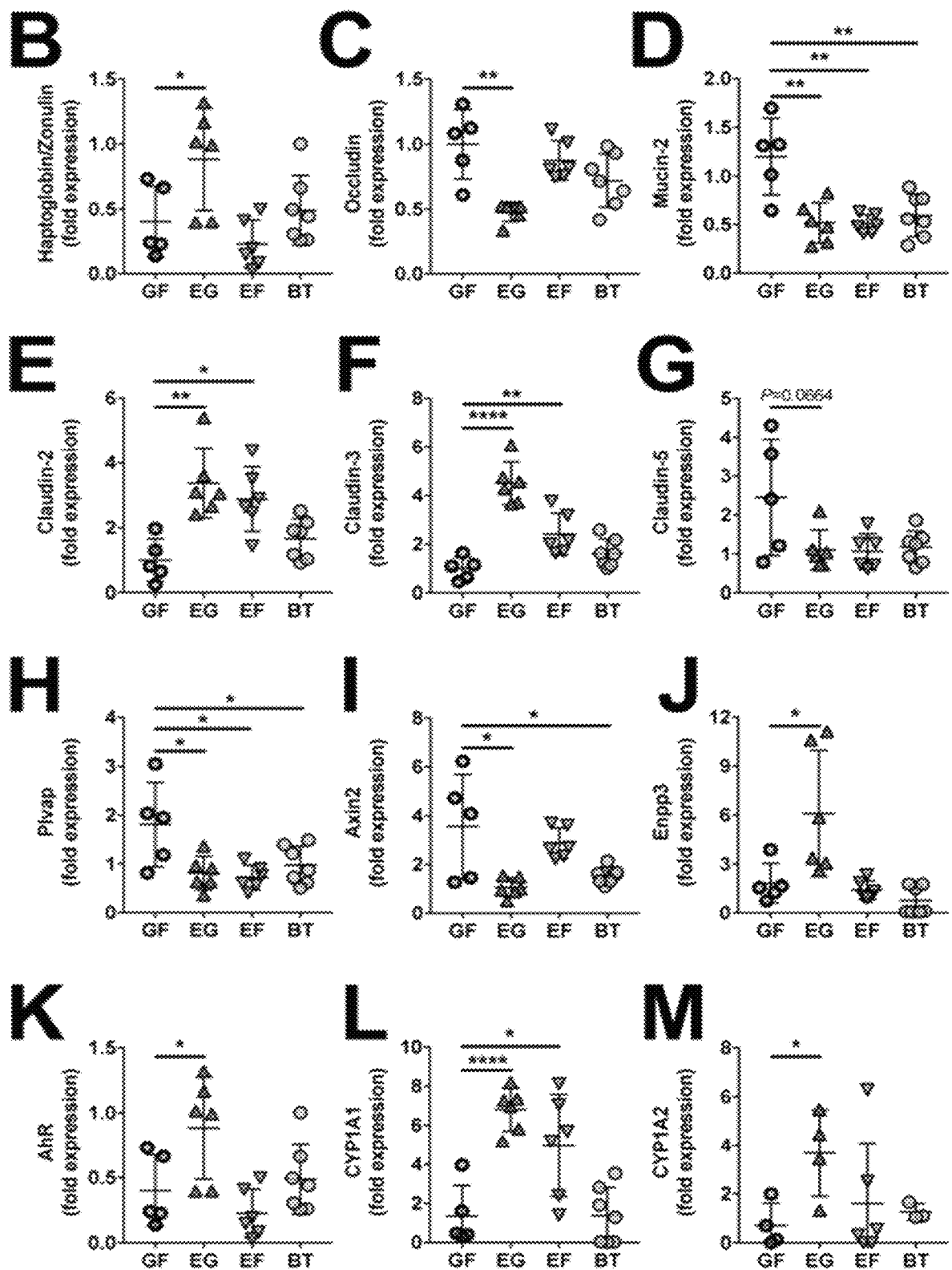
(FIG. 3B-FIG. 3M) RT-qPCR analysis of ileum RNA as described in (FIG. 3A).
Figure 3N:
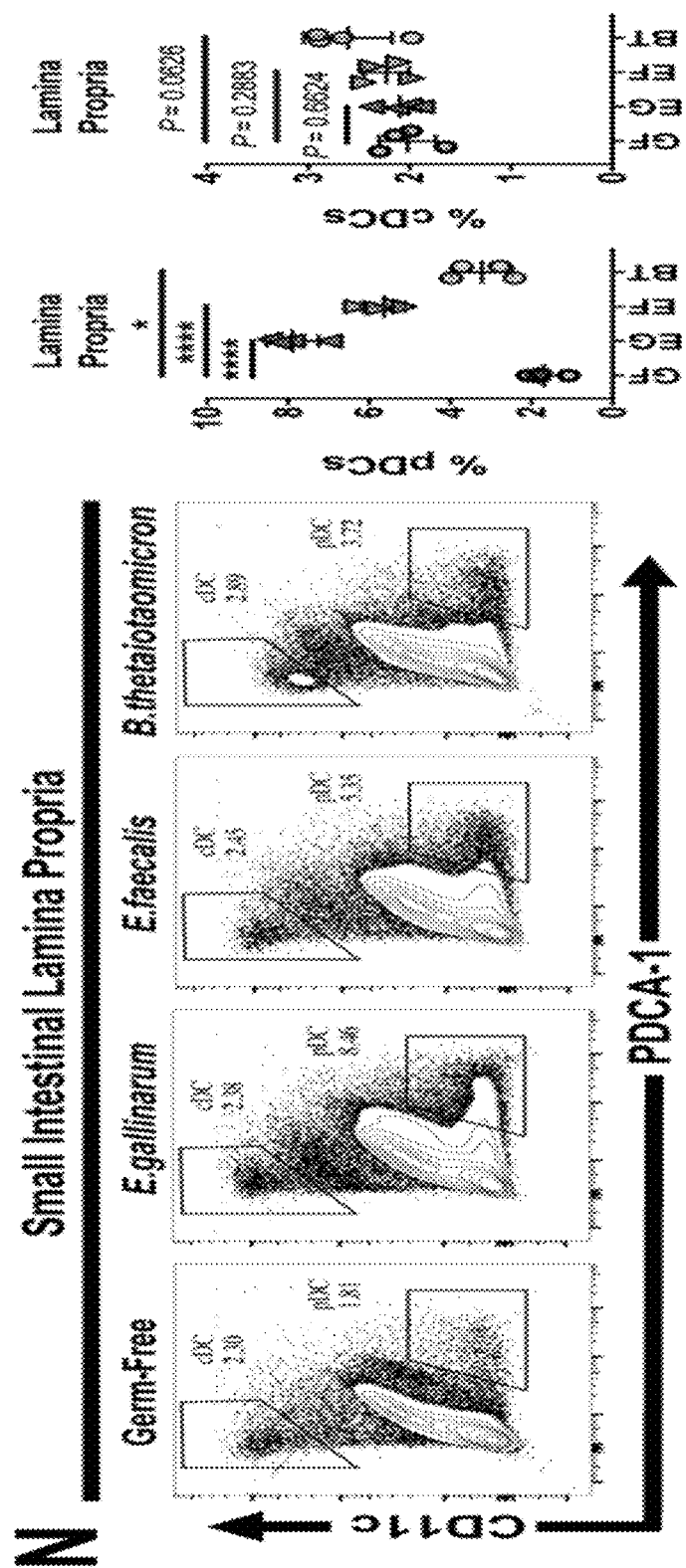
(FIG. 3N) Plasmacytoid dendritic cell (pDC) and conventional dendritic cell (cDC) frequencies in the small intestinal lamina propria mice of 12-week-old germ-free mice that were evaluated 3 weeks after monocolonization for pDC and cDC frequencies by FACS analysis.
Figure 3O:
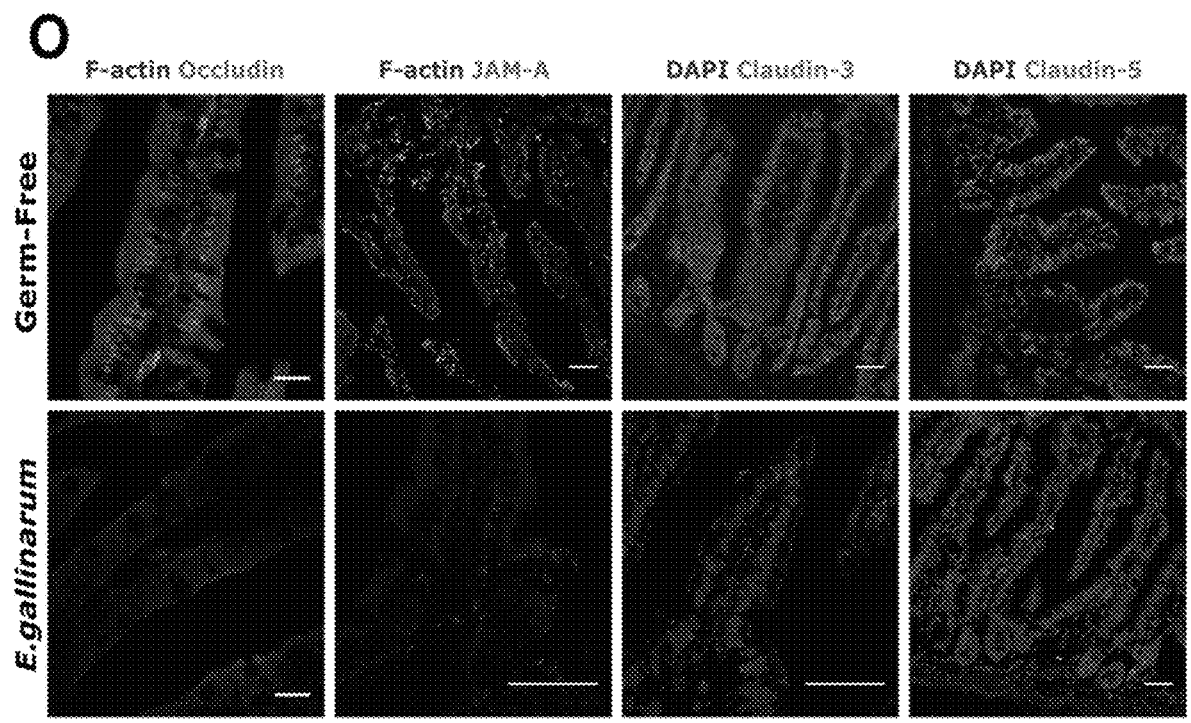
Figure 12:
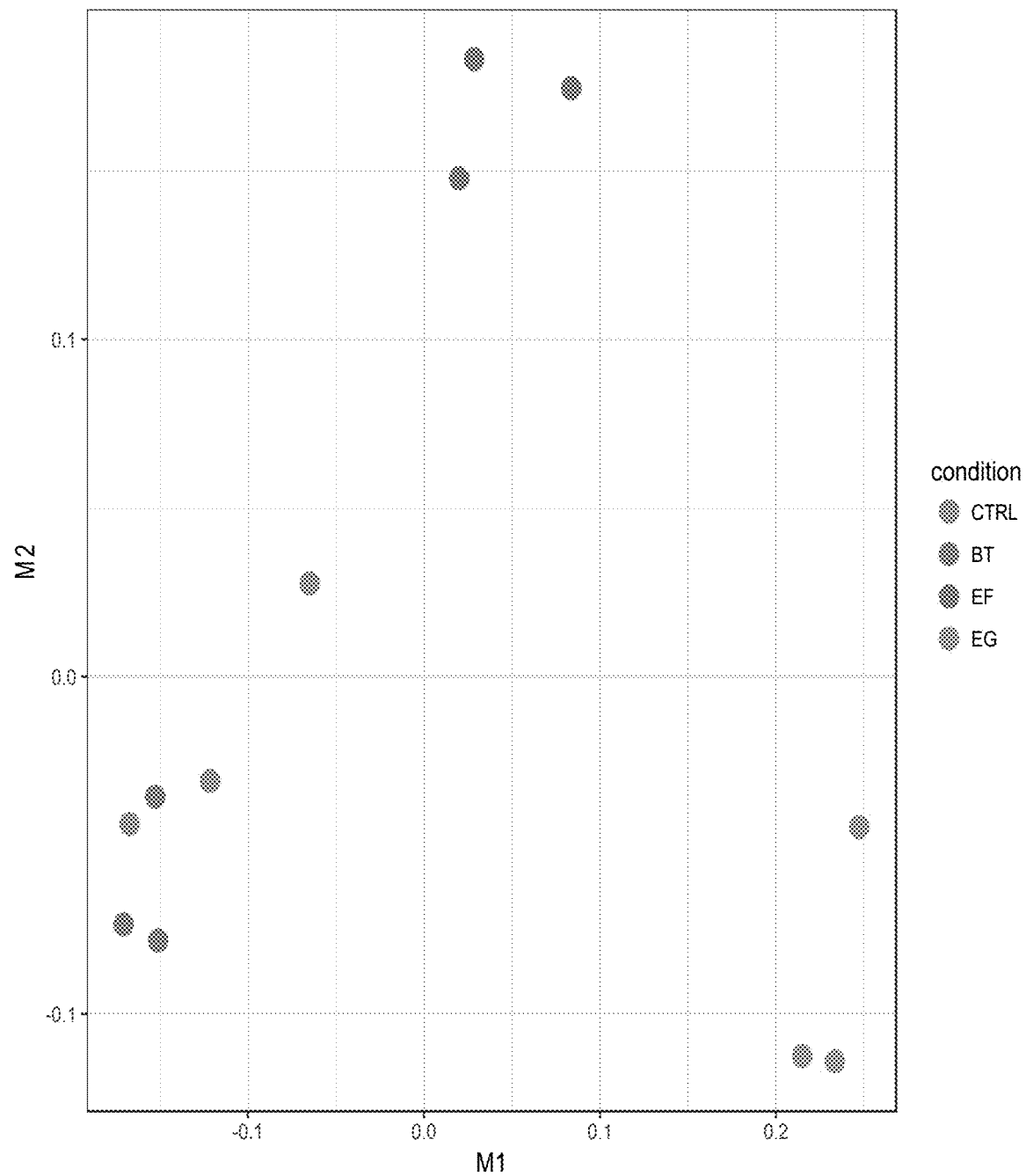
FIG. 12 depicts multi-dimensional scaling plots of RNA expression profiling of ileal samples from germ-free C57BL/6 mice monocolonized with E. gallinarum, E. faecalis, B. thetaiotaomicron. Germ-free 14 week-old C57BL/6 mice were kept sterile (controls, CTRL) or monocolonized with E. gallinarum (EG), E. faecalis (EF) or B. thetaiotaomicron (BT) for 8 hours prior to RNA isolation of ileal tissue for RNA-seq analysis as described elsewhere herein. Multi-dimensional scaling plots (MDS) are shown from pooled samples (n=3 each) of the most differentially induced genes as shown in FIG. 13.
Figure 13:
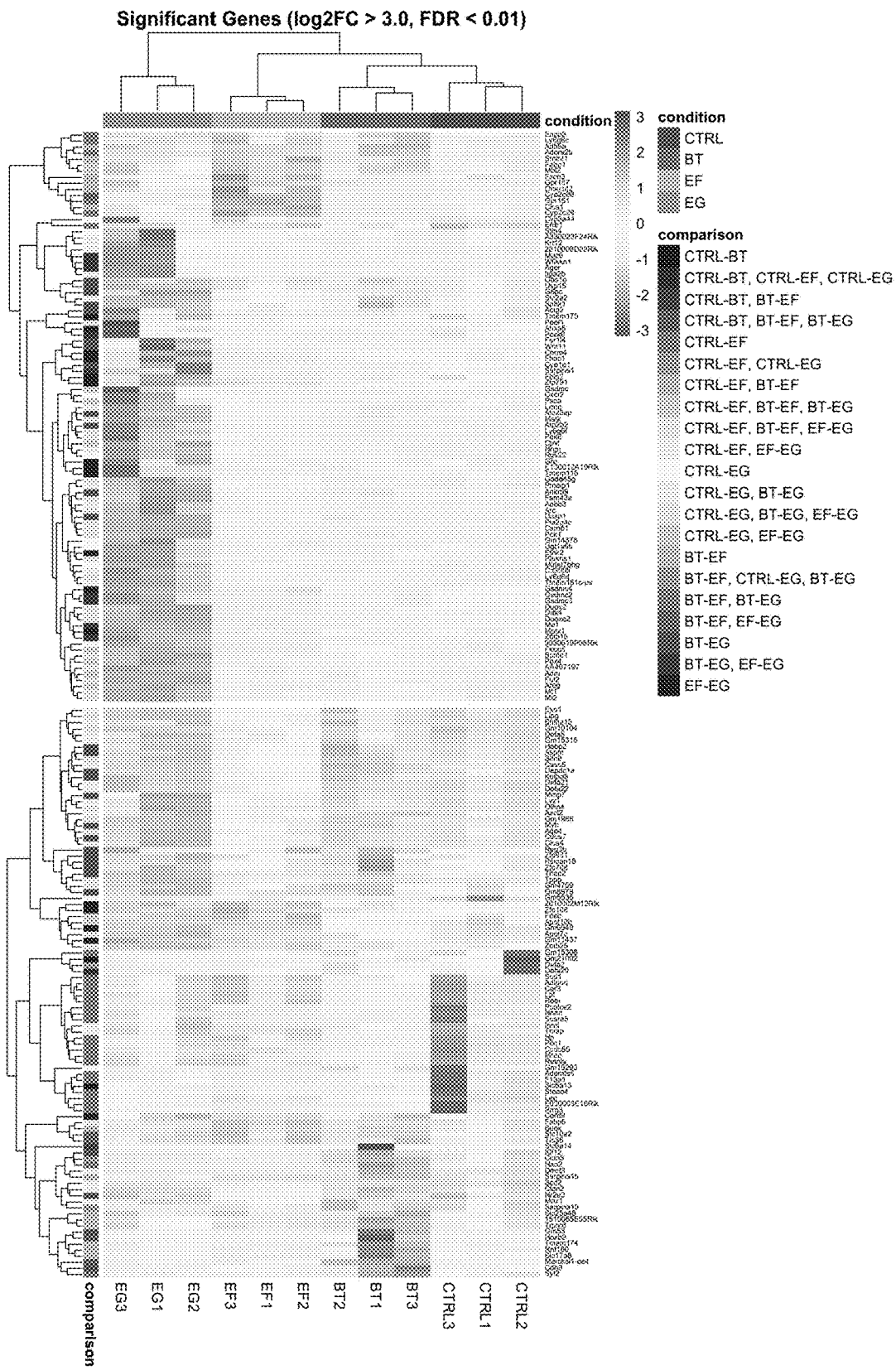
FIG. 13 depicts the results of example experiments demonstrating RNA expression profiling of small intestinal tissue from germ-free mice monocolonized with E. gallinarum, E. faecalis or B. thetaiotaomicron. Germ-free 14 week-old C57BL/6 mice were kept sterile (controls, CTRL) or monocolonized with E. gallinarum (EG), E. faecalis (EF) or B. thetaiotaomicron (BT) for 8 hours prior to RNA isolation of ileal tissue for RNA-seq analysis as described elsewhere herein. Heatmap shows hierarchical clustering of differentially expressed transcripts (log 2FC>3, false discovery rate >3). See Manfredo-Vieira et al., (2018, The Enemy Lies Within: Spontaneous Translocation of a Gut Pathobiont Drives Autoimmunity, Science).
Figures 14A, 14B:
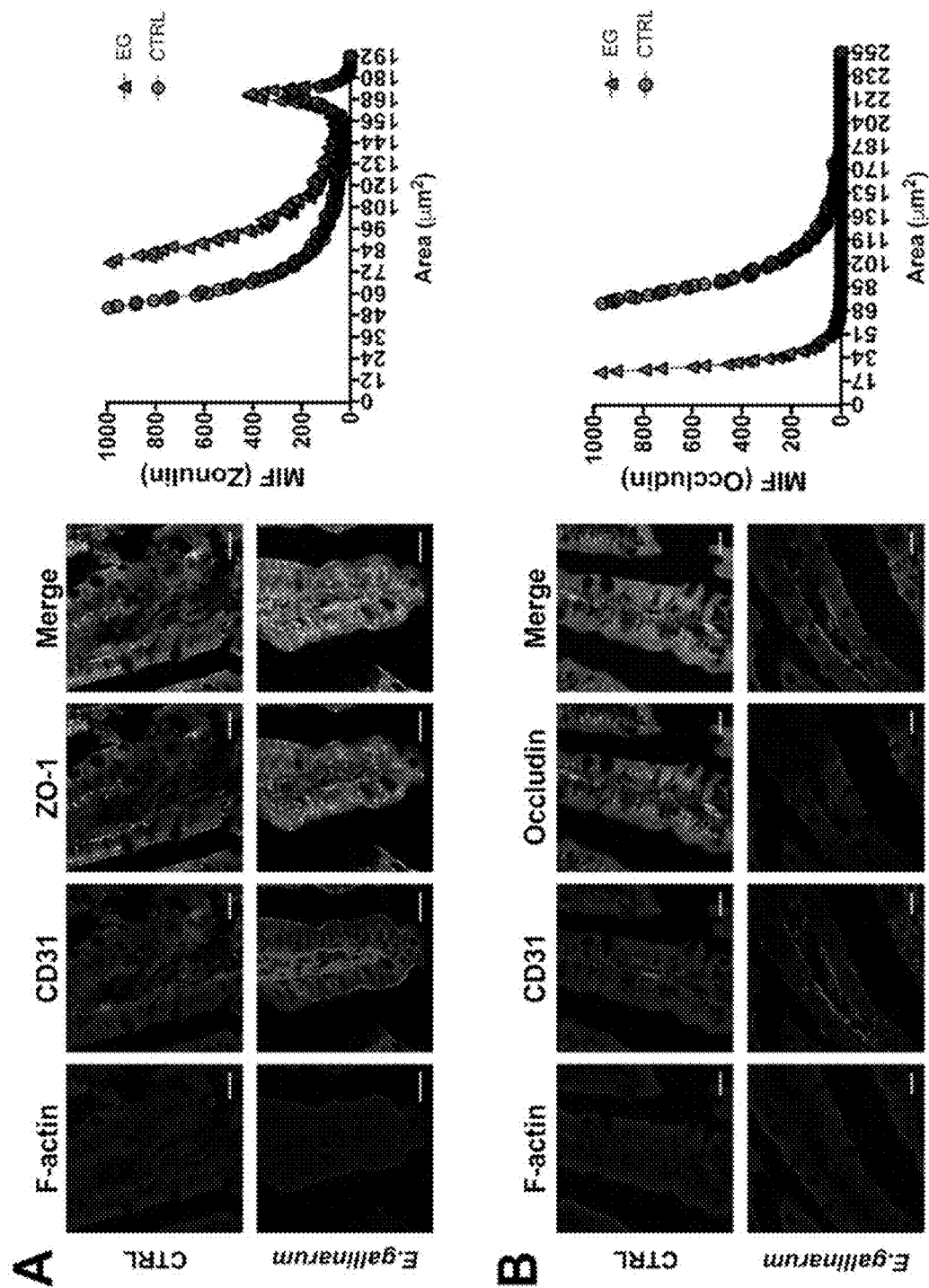
FIG. 14 depicts the results of example experiments depicting the distribution of tight junction proteins on small intestinal endothelial cells of E. gallinarum-monocolonized versus germ-free C57Bl/6 mice. Confocal imaging of gut tissues was performed as described elsewhere herein. Shown are the localizations of TJ proteins on blood vessels (CD31, red). In green: (I) ZO-1 and (J) occludin. Images are representative of 6 different mice each. Scale bars: 20 µm.
Figures 15A, 15B:
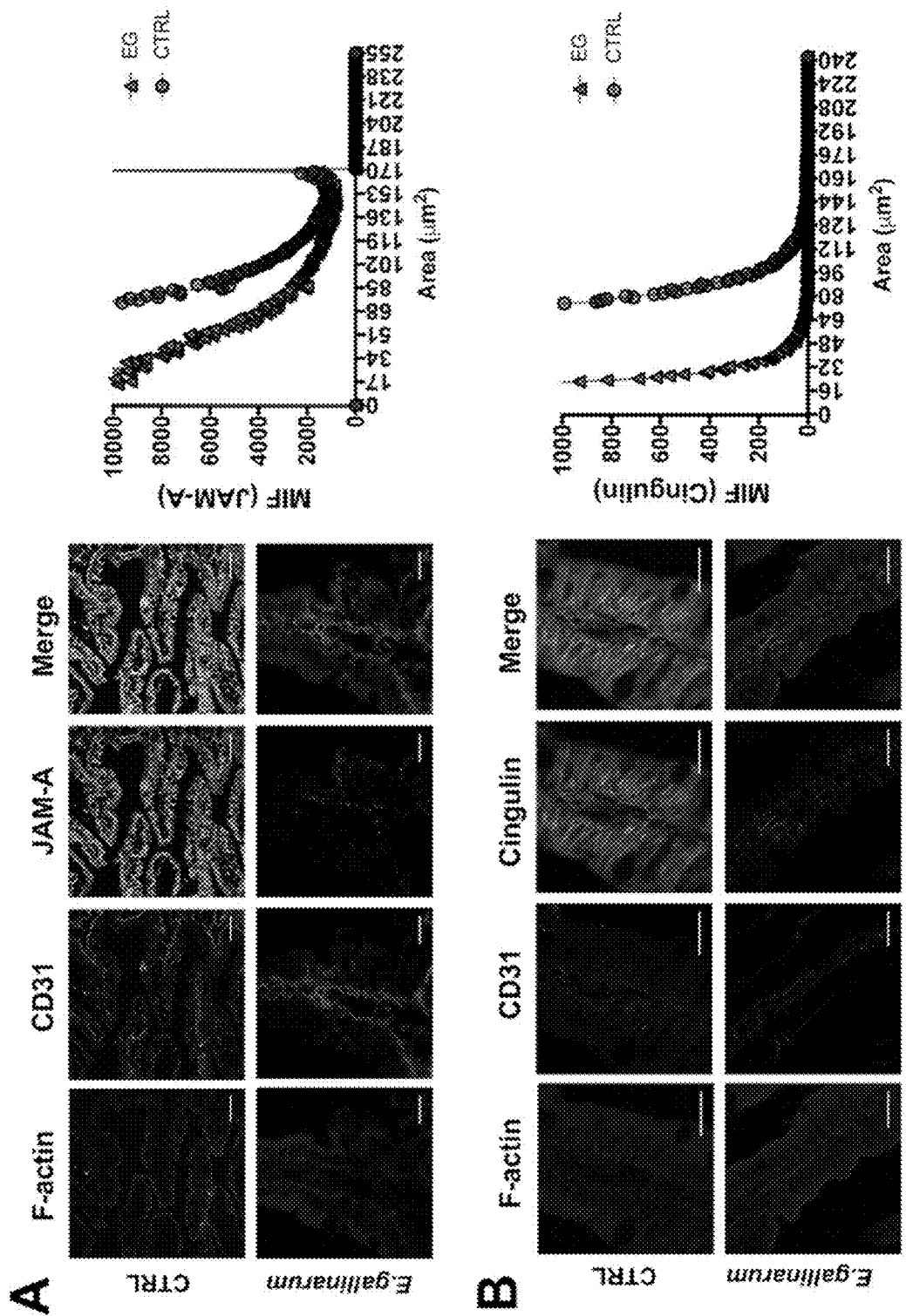
FIG. 15A and FIG. 15B, depicts the results of example experiments depicting the distribution of tight junction proteins on small intestinal endothelial cells of E. gallinarum-monocolonized versus germ-free C57Bl/6 mice. Confocal imaging of gut tissues was performed as described elsewhere herein. Shown are the localizations of TJ proteins on blood vessels (CD31, red). In green.
Figures 16A, 16B:
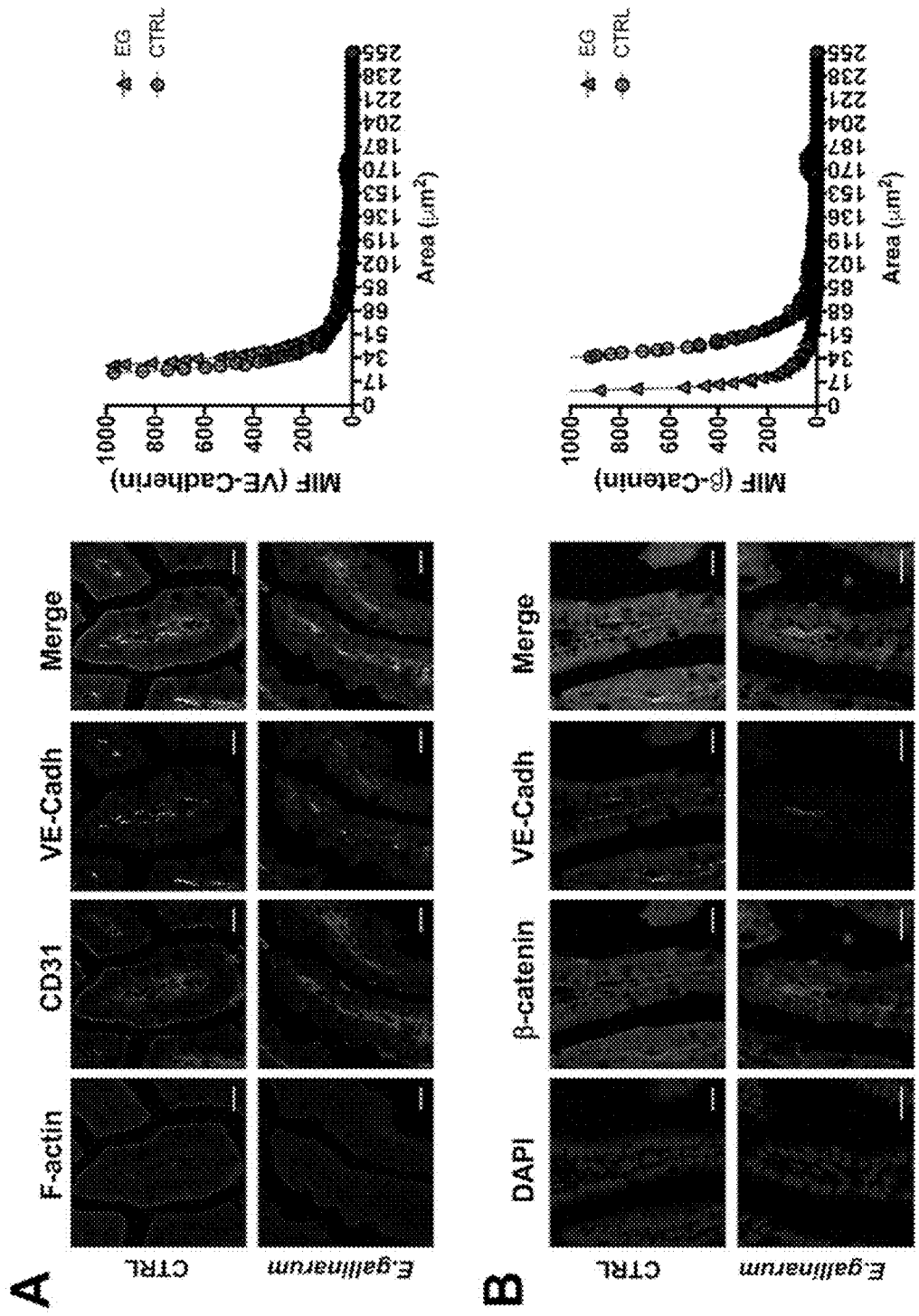
FIG. 16A and FIG. 16B, depicts the results of example experiments depicting the distribution of adherent junction proteins on small intestinal vessels of E. gallinarum-monocolonized versus germ-free C57Bl/6 mice. Confocal imaging of small intestinal gut tissues was performed as described elsewhere herein. Shown are the localizations of AJ proteins on endothelial cells.
Figures 17A, 17B, 17C:
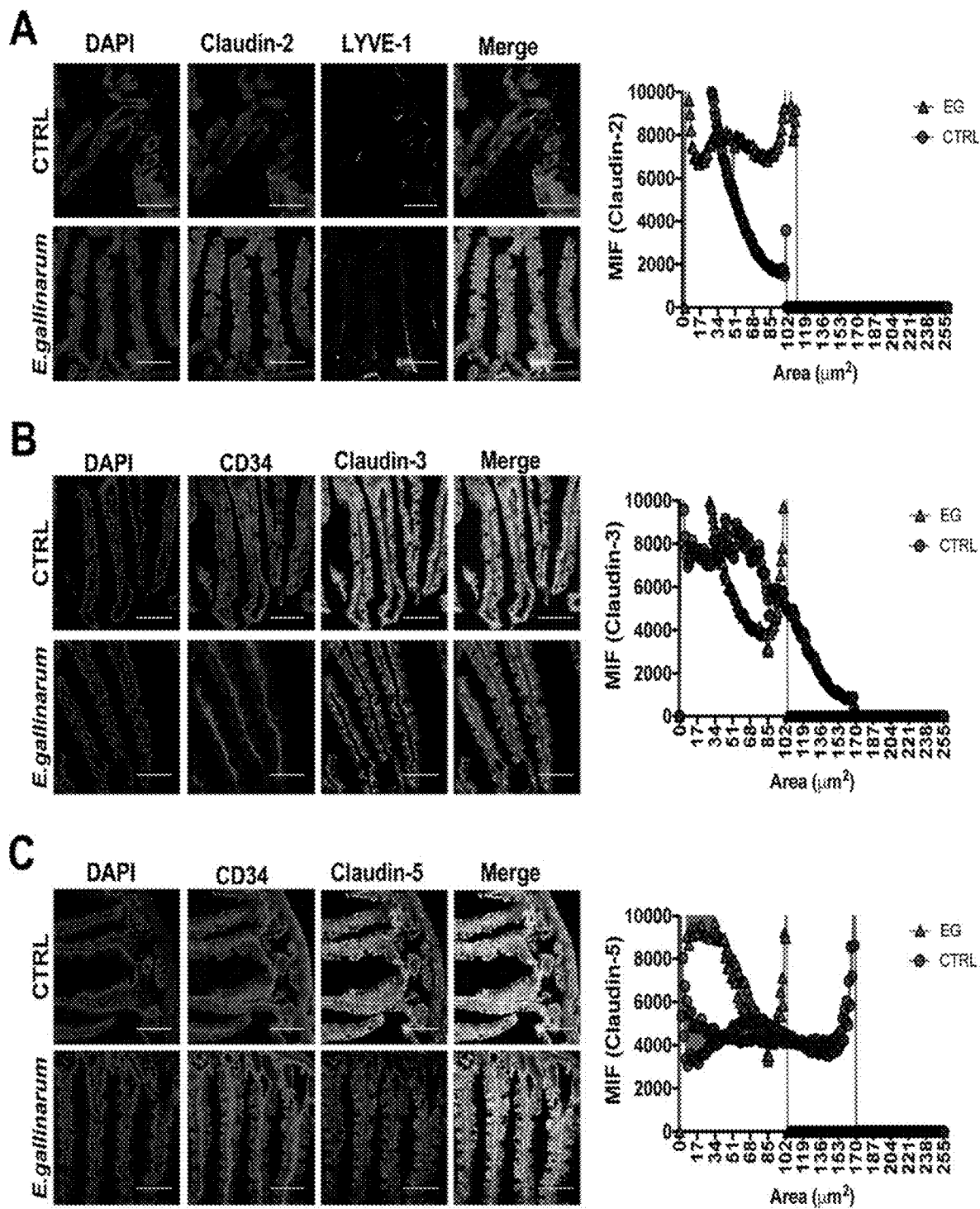
FIG. 17A through FIG. 17C, depicts the results of example experiments demonstrating that claudin-2, -3 and -5 are altered by E. gallinarum monocolonization of germ-free C57Bl/6 mice. Confocal imaging of small intestinal tissues was performed as described elsewhere herein. Shown are the localizations of claudin-2, -3 and -5. Intestinal sections were stained for (FIG. 17A) CLDN2 (red) and LYVE-1 (green), (FIG. 17B) CLDN3 (green) and CD34 (red) and (FIG. 17C) CLDN5 (green) and CD34 (red) to mark blood vessels. All the intestinal sections were stained with DAPI (blue) to visualize cell nuclei. Images are representative of 6 different mice each. Scale bars: 20 µm.

To test if *E. gallinarum* induces pro-inflammatory pathways and alters gut barrier-related molecules in small intestinal tissue to translocate to internal organs, RNA expression profiling of *E. gallinarum*-versus *E. faecalis*- and *B. thetaiotaomicron*-monocolonized mice was performed (FIG. 3, FIG. 12 and FIG. 13). *E. gallinarum* indeed altered ileal molecules related to barrier function (occludin, claudins, Plvap, Axin2), the mucus layer (mucin, Fut2), antimicrobial defence (Reg3b, Defa2), and inflammation (Cxcr2, AhR/Cyp1a1, Enpp3). Enpp3 increases plasmacytoid dendritic cells (pDCs), key cells contributing to the IFN signature in human SLE (Crow, 2014, J Immunol, 192, 5459-5468; Eloranta et al., 2013, Arthritis Rheum, 65, 853-863; Furuta et al., 2017, PLoS One, 12, e0172509), which were induced by *E. gallinarum* in the small intestinal lamina propria (FIG. 3N). To visualize gut epithelial, vascular and lymphatic barrier molecules altered on RNA level, confocal microscopy was performed. Intestinal epithelial and endothelial cells have tight junctions (TJ) and adherent junctions (AJ) (Luissint et al., 2016, Gastroenterology, 151, 616-632). TJ are formed by occludin, zonula occludens-1 (ZO-1), cingulin, and junctional adhesion molecule-A (JAM-A); adherent junctions (AJ) are formed by vascular endothelial cadherin (VE-cadherin) and β-catenin. The majority of these junctional proteins were altered in gnotobiotic mice monocolonized with *E. gallinarum* to support increased barrier leakiness (FIG. 3O and FIG. 14-FIG. 16). Claudin-2, -3 and -5 are expressed in lymphatic endothelial TJ and their expression was altered as well to support barrier disintegration in *E. gallinarum*-monocolonized mice (FIG. 3O and FIG. 17).

Figures 4A, 4B, 4C, 4D, 4E, 4F, 4G, 4H, 4I:
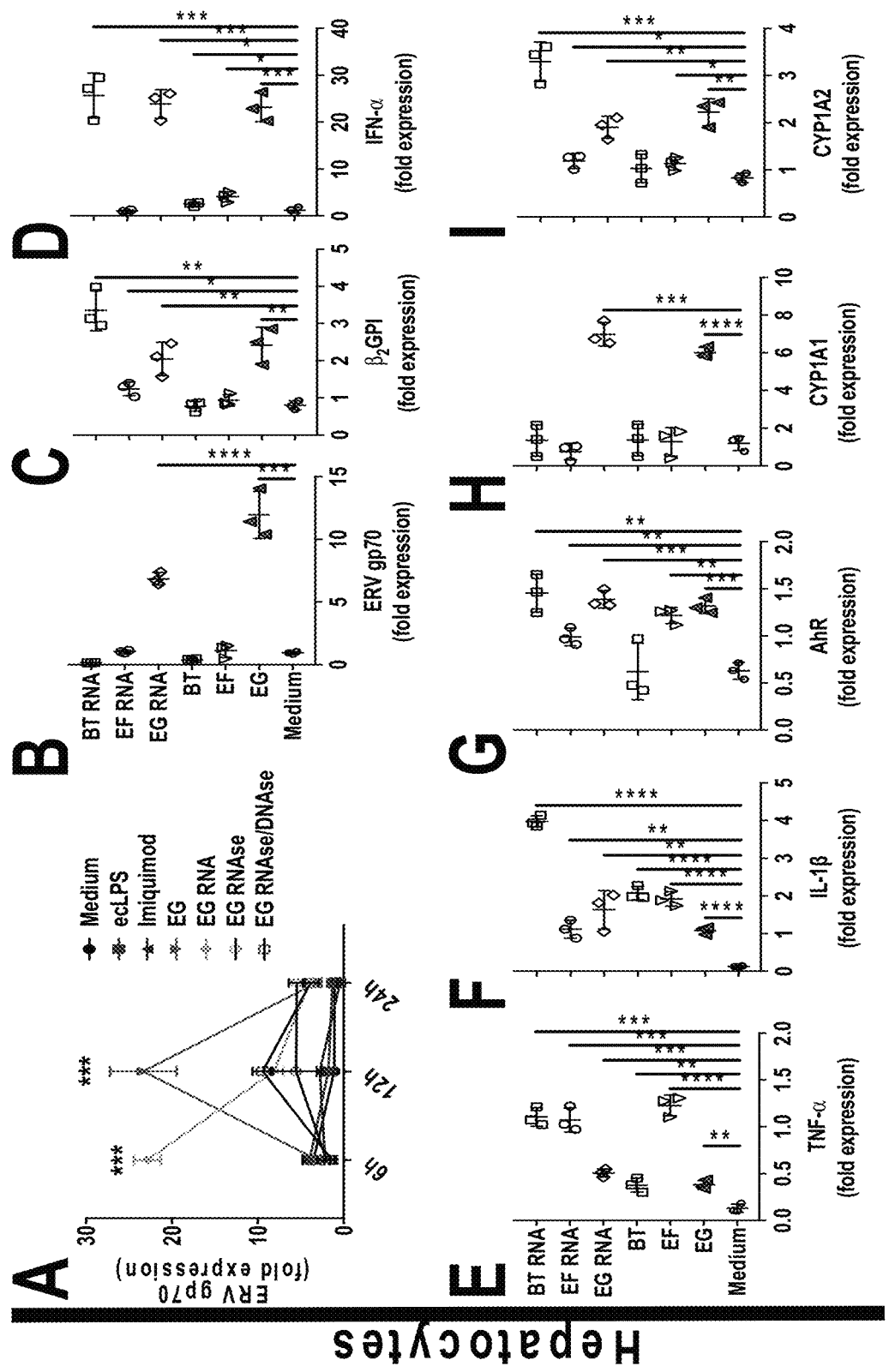
FIG. 4A through FIG. 4P, depicts the results example experiments examining *E. gallinarum*-hepatocyte co-cultures, whole genome sequencing, and AhR antagonism in vivo.
(FIG. 4B-FIG. 4I) EG, *E. faecalis* (EF) *B. thetaiotaomicron* (BT) lysates or isolated RNA were co-cultured with hepatocytes as in (FIG. 4A) and the expression of ERV gp70, the autoantigen β2GPI, cytokines and AhR were measured 6 hours later (*$P<0.0001$, ANOVA followed by the Bonferroni test). Dendritic cells from 16-week-old (NZWxBXSB)$F_1$ mice were co-cultured with bacterial stimuli as in (FIG. 4B) to determine expression levels of cytokines (FIG. 4J-FIG. 4M) by RT-qPCR ($P<0.002$ and ***$P<0.0006$, ANOVA followed by the Bonferroni test).
Figures 4J, 4K, 4L, 4M:
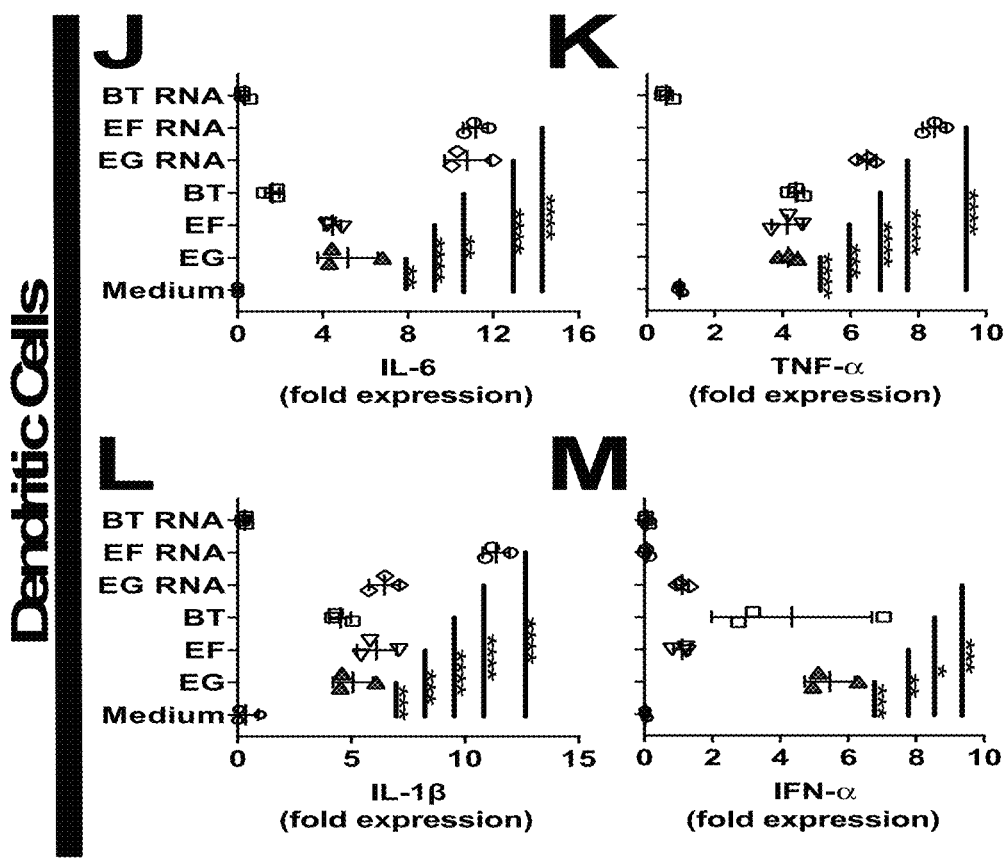
FIG. 4, comprising
(FIG. 4N) *E. gallinarum* full genome sequencing as detailed elsewhere herein. Selected genes from each gene cluster (1-27) are shown in red, genes encoding enzymes involved in the shikimate pathway in green. Serum anti-RNA (FIG. 4O) and anti-dsDNA (FIG. 4P) IgG of 16-week-old (NZWxBXSB)$F_1$ mice gavaged with vehicle or EG and treated with AhR antagonist CH223191 or mock as detailed elsewhere herein (*$P<0.05$, $P<0.01$, *$P<0.001$ and ****$P<0.0001$, Student's t test).
Figures 4N, 4O, 4P:
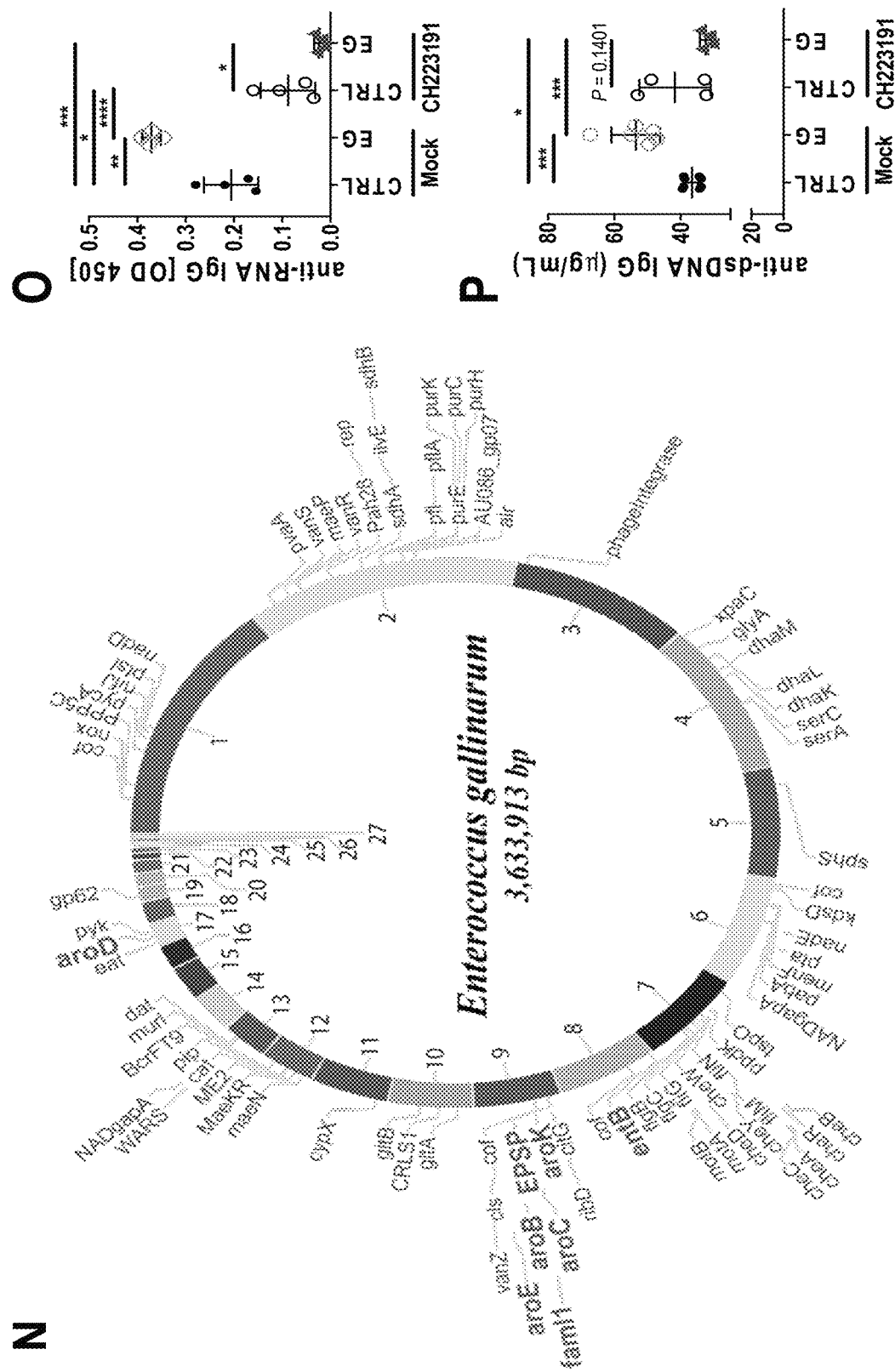
Figure 18:
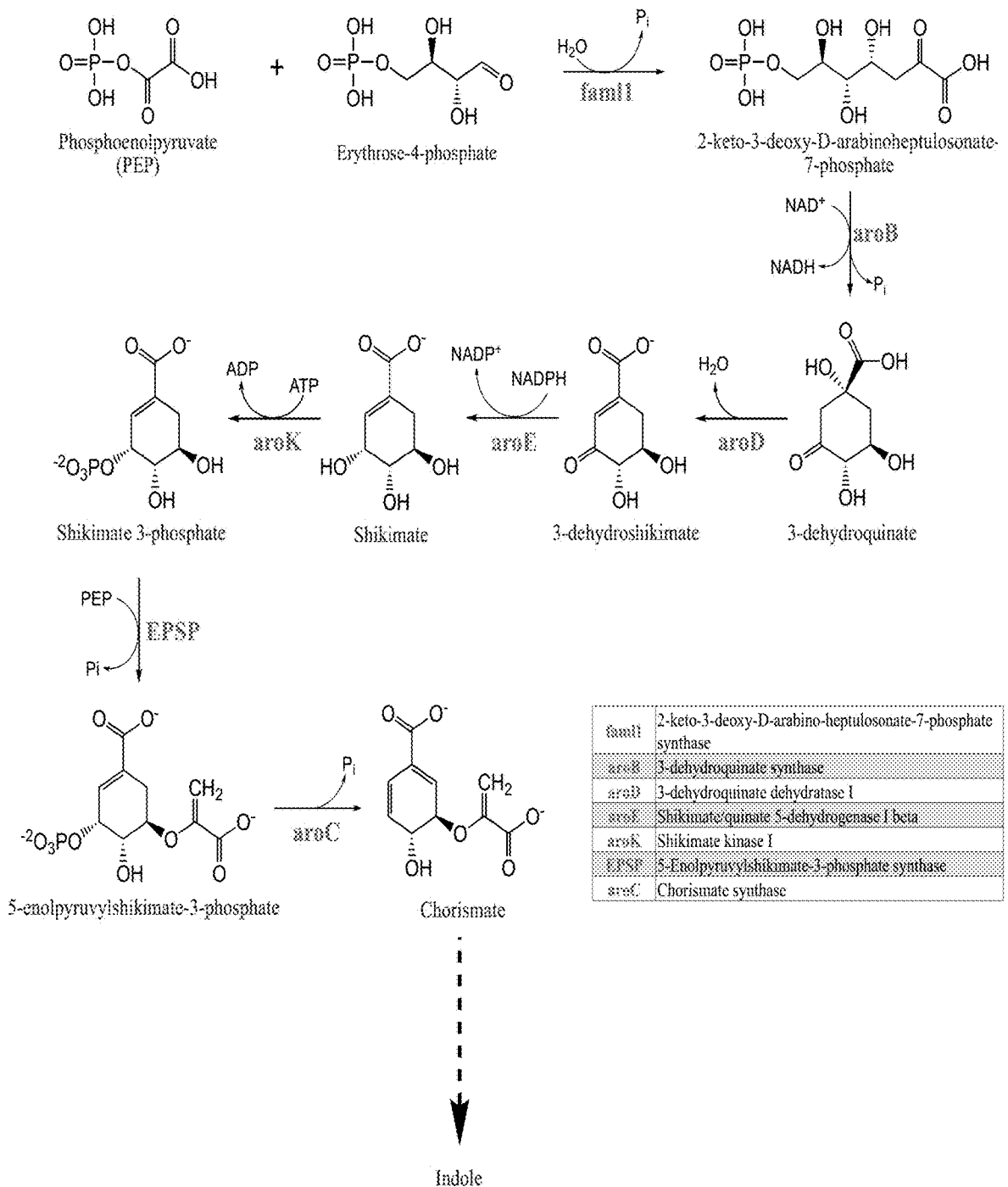
FIG. 18 depicts biochemical modelling of the shikimate pathway based on enzymes encoded in the E. gallinarum genome. Phosphoenolpyruvate and erythrose-4-phosphate react to form 2-keto-3-deoxy-D-arabinoheptulosonate-7-phosphate in a reaction catalyzed by the enzyme 2-keto-3-deoxy-D-arabino-heptulosonate-7-phosphate synthase (fam11). 2-keto-3-deoxy-D-arabinoheptulosonate-7-phosphate is then transformed to 3-dehydroquinate in a reaction catalyzed by NAD+ and 3-dehydroquinate synthase (aroB). 3-Dehydroquinate is dehydrated to 3-dehydroshikimate by the enzyme 3-dehydroquinate dehydratase (aroD), which is reduced to shikimate by the enzyme Shikimate/quinate 5-dehydrogenase I beta (aroE), which uses nicotinamide adenine dinucleotide phosphate (NADPH) as a cofactor. Then, shikimate kinase (aroK) catalyzes the ATP-dependent phosphorylation of shikimate to form shikimate 3-phosphate. Subsequently, shikimate 3-phosphate reacts with phosphoenolpyruvate to form 5-enolpyruvylshikimate-3-phosphate in a reaction catalyzed by 5-enolpyruvylshikimate-3-phosphate synthase (EPSP) followed by loss of pyrophosphate in a reaction catalyzed by chorismate synthase to form chorismate. Chorismate can be further metabolized to indole and tryptophan by E. gallinarum (KEGG pathway ega01230).

Next, it was examined whether liver-resident *E. gallinarum* could induce hepatic overexpression of ERV gp70 that fuels anti-ERV IC formation and systemic autoimmunity, which is suppressed by vancomycin as shown above (see FIG. 7). Indeed, hepatocyte coculture with *E. gallinarum* induced multiple autoimmune-promoting factors. *E. gallinarum*, in particular its RNA (a potential TLR7 ligand), potently induced the autoantigens ERV gp70 and 32GPI (FIG. 4A-FIG. 4C). It also induced expression of the signature cytokine in lupus, type I IFN, as well as other proinflammatory cytokines and pathways (FIG. 4D-FIG. 4I). These effects occurred not only in hepatocytes but also in dendritic cells (FIG. 4J-FIG. 4M). The AHR-CYP1A1 pathway, a known innate antimicrobial defence mechanism and inducer of Th17 cells (Veldhoen et al., 2008, Nature, 453, 106-109; Moura-Alves et al., 2014, Nature, 512, 387-392; Schiering et al., 2017, Nature, 542, 242-245; Stockinger et al., 2014, Annu Rev Immunol, 32, 403-432), was also upregulated (FIG. 4G-FIG. 4I). Since tryptophan-derived indoles are bacterial ligands for AHR, it was examined if *E. gallinarum* encodes genes for enzymes involved in the production of AHR ligands. Whole genome sequencing of *E. gallinarum* revealed multiple genes encoding enzymes involved in the shikimate pathway leading to chorismate that give rises to tryptophan and indoles after further bacterial degradation (FIG. 4N, FIG. 18 and FIG. 24) (Stockinger et al., 2014, Annu Rev Immunol, 32, 403-432; Dosselaere and Vanderleyden, 2001, Crit Rev Microbiol, 27, 75-131).

Figures 19A, 19B:
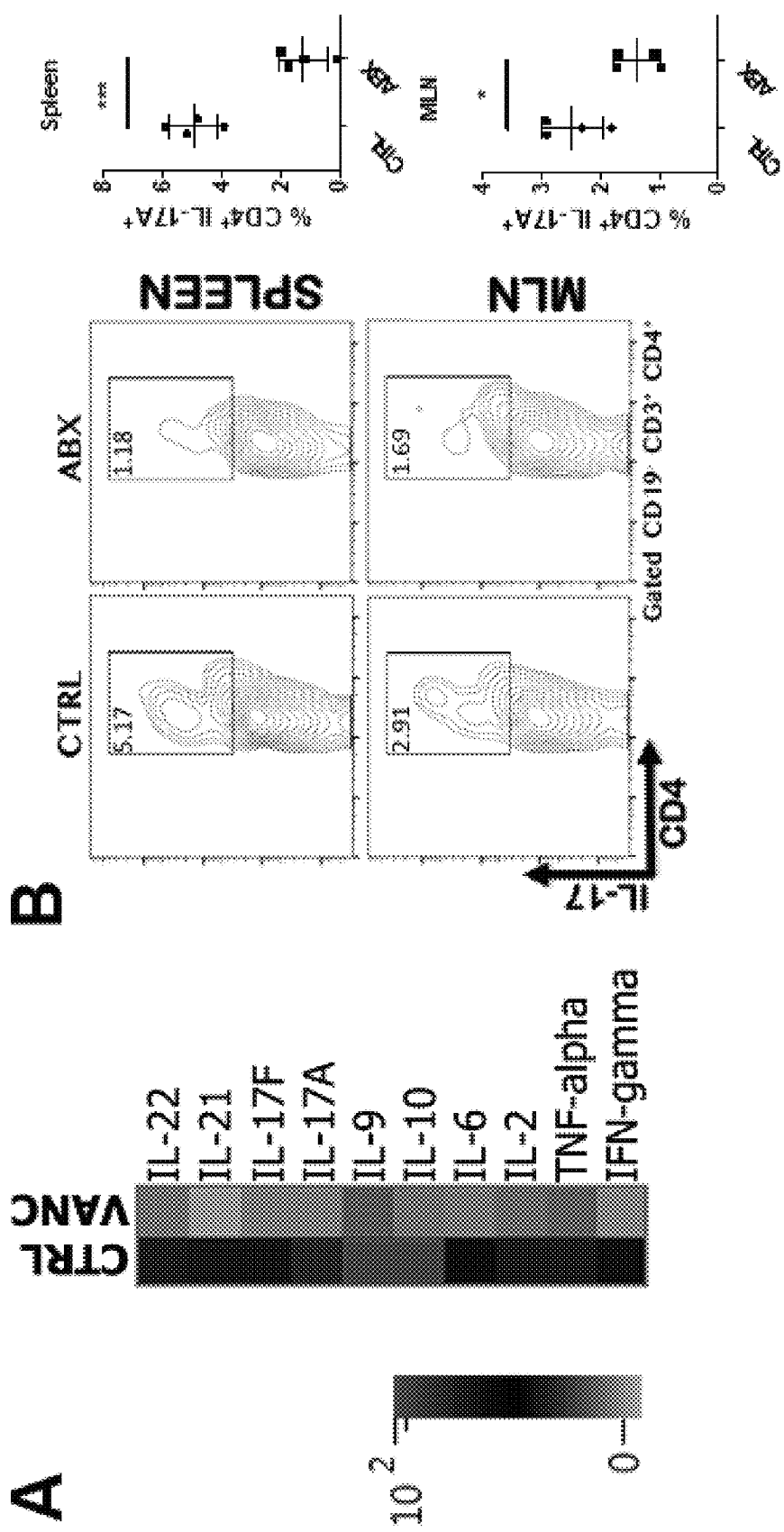
FIG. 19A through FIG. 19D, depicts the results of example experiments demonstrating vancomycin treatment suppresses inflammatory cytokines in (NZWxBXSB)$F_1$ splenocyte supernatants and Th17 and Tfh cell subsets in secondary lymphoid organs.
Figure 19C:
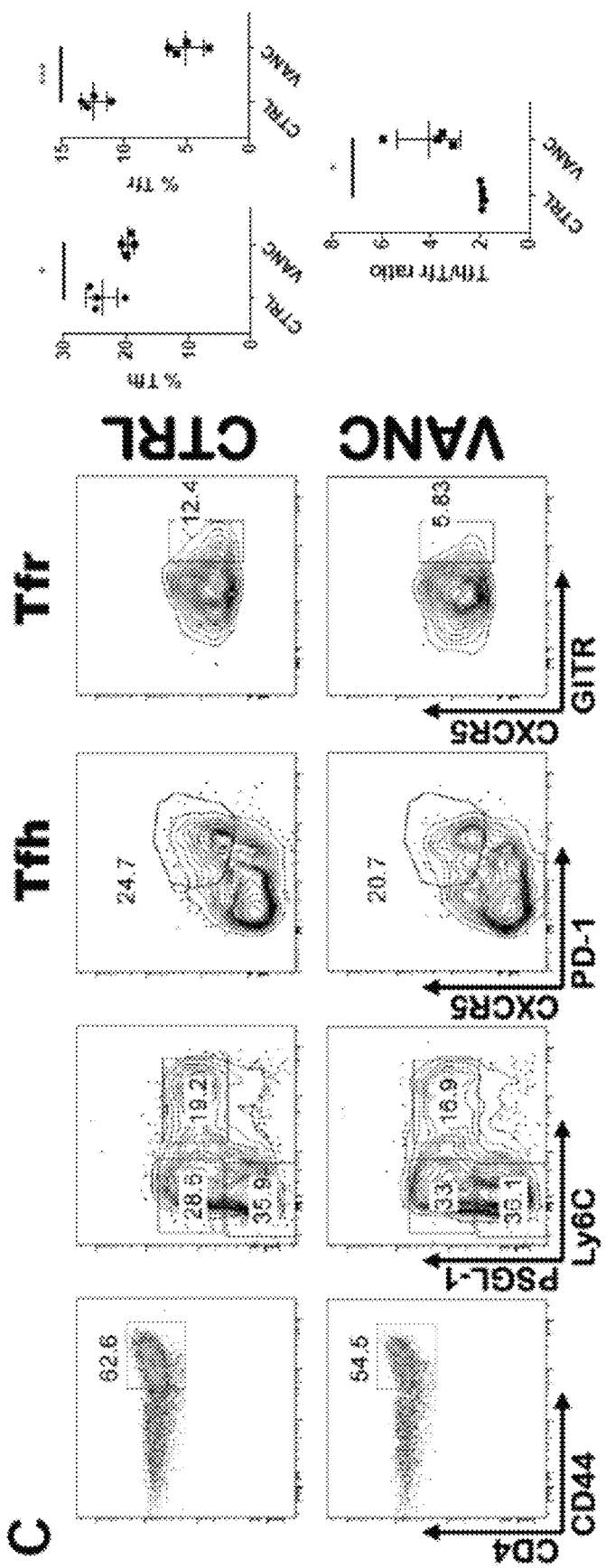
Figure 19D:
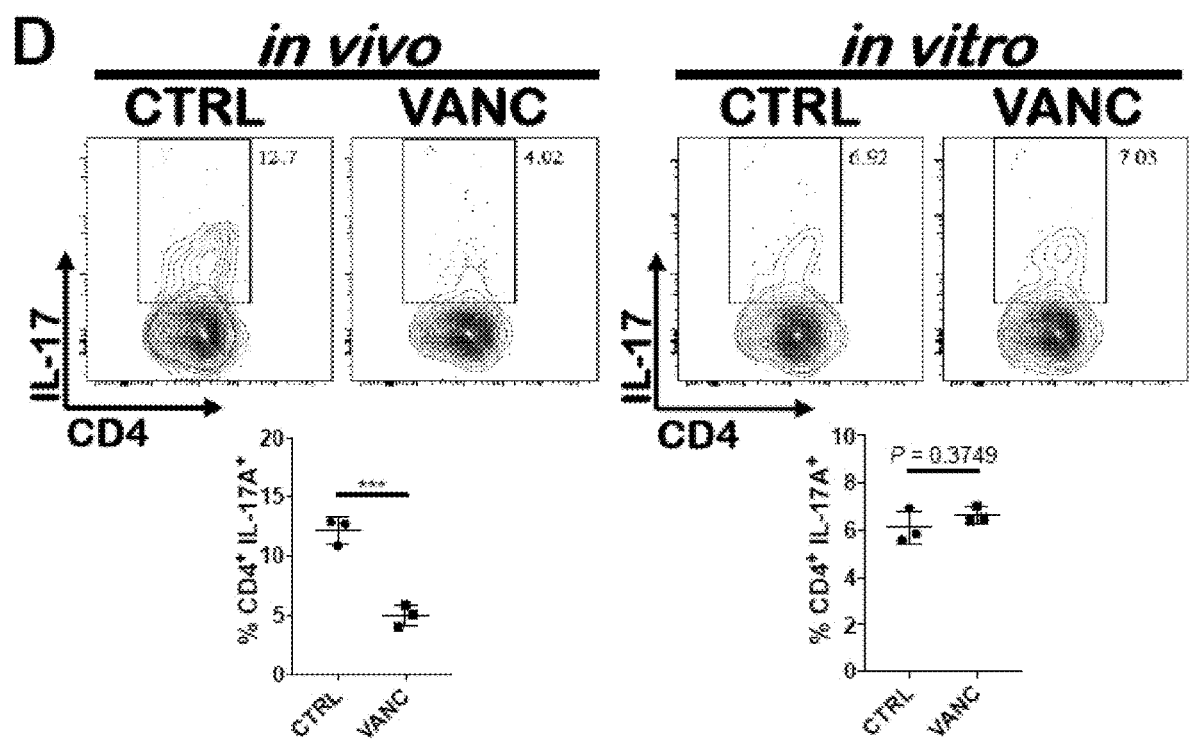
Figure 20:
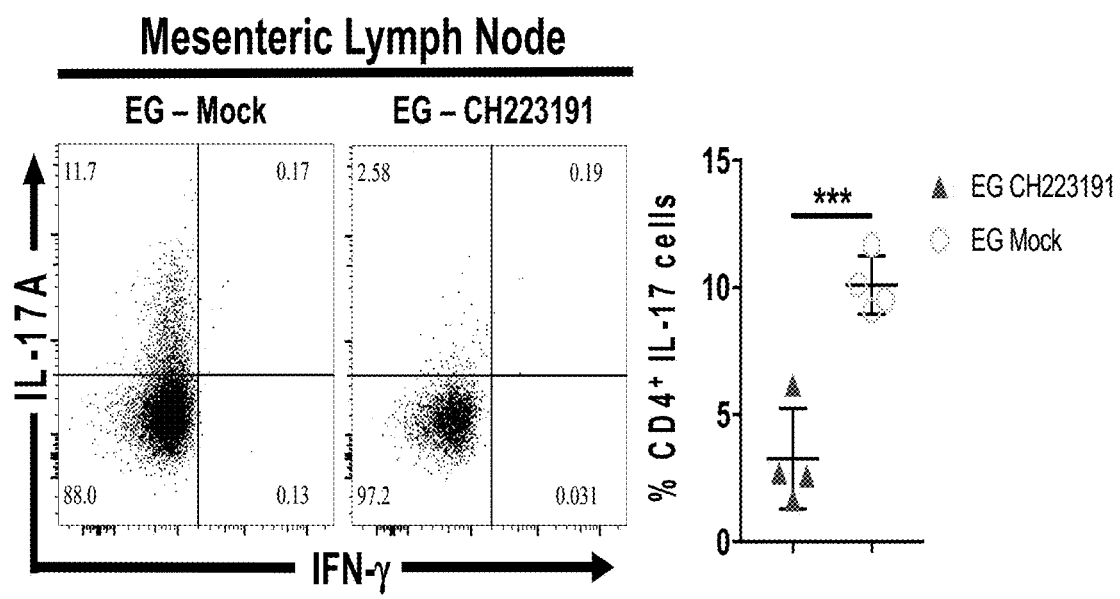
FIG. 20 depicts the results of example experiments demonstrating that AHR inhibition reverses Th17 cell and autoantibody induction by E. gallinarum. 14-week-old $(NZWxBXSB)F_1$ mice (n=4) were treated with broad-spectrum antibiotics (ABX; 0.5 g/L of vancomycin, 1.0 g/L ampicillin, 1.0 g/L metronidazole and 1.0 g/L neomycin) in the drinking water from 10 weeks to 14 weeks of age. 24 hours later mice were gavaged with E. gallinarum every week for 4 weeks. Subsequently, mice were injected i.p. with CH223191 (300 µg/mouse/day) (a selective AhR antagonist; Sigma-Aldrich) or mock 5 days a week for the entire duration of the experiment starting at 14 weeks of age. After 4 weeks of bacterial gavage and AhR antagonist treatment, mice were euthanized for FACS analysis of MLN Th17 cells. Th17 cell frequencies were determined in the mesenteric lymph node by intracellular staining of IL-17A in $CD3^+$ $CD4^+$ $CD19^-$ $CD44^+$ cells. Shown are representative FACS plots and frequencies of Th17 cells from individual mice. Shown is one representative experiment out of three experiments (***P=0.001, Student's t test).

Next, it was tested if *E. gallinarum*-immune interactions, possibly via the AHR pathway, induce Th17 and T follicular helper (Tfh) cells in vivo given that these CD4 T cell subsets are crucial for systemic autoantibody production (Craft, 2012, Nat Rev Rheumatol, 8, 337-347; Crotty, 2014, Immunity, 41, 529-542). Broad-spectrum antibiotics or vancomycin treatment in (NZWxBXSB)F$_1$ mice (negative for segmented filamentous bacteria) indeed reduced Th17 and Tfh cells and its cytokine signatures (FIG. 19A-FIG. 19C) along with *E. gallinarum* translocation (see FIG. 7K-FIG. 7N). Vancomycin itself had no direct influence on immune cells in vitro (FIG. 19D). The in vivo effects on T cells correlated with suppressed *E. gallinarum* translocation, immunopathology, and autoantibodies, as well as lower serum and hepatic levels of the ERV gp70 autoantigen and anti-ERV gp70 ICs (see FIG. 1 and FIG. 7) that are known to cause glomerulonephritis (Tabata et al., 2000, J Virol, 74, 4116-4126). Importantly, administration of an AHR-selective antagonist abrogated Th17- and autoantibodies-inducing effects of *E. gallinarum* in (NZWxBXSB)F$_1$ mice in vivo (FIG. 4O-FIG. 4P and FIG. 20), linking AHR signals with *E. gallinarum*-induced autoimmunity.

Figures 5A, 5B, 5C, 5D, 5E, 5F:
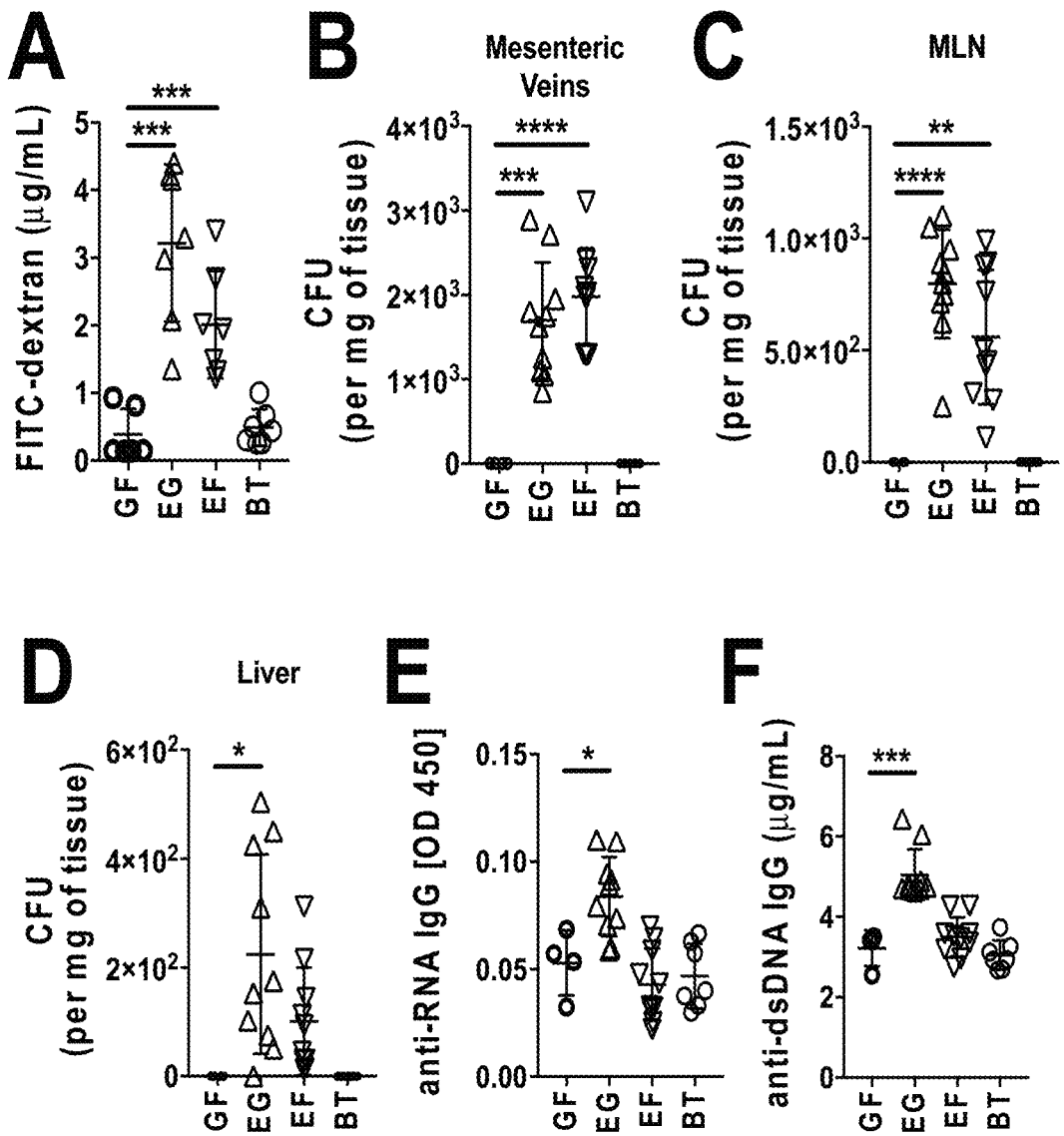
FIG. 5A through FIG. 5H, depicts the results of example experiments demonstrating that monocolonization of germ-free mice with *E. gallinarum* and *E. faecalis*, but not *B. thetaiotaomicron*, leads to impaired gut barrier and translocation, but only *E. gallinarum* induces autoantibodies and Th17 cells. C57BL/6 germ-free (GF) mice were monocolonized with *E. gallinarum* (EG), *E. faecalis* (EF) and *B. thetaiotaomicron* (BT) at 12 weeks of age and evaluated 3 weeks later for integrity of the gut barrier with FITC-dextran (FIG. 5A), and for translocation to the mesenteric veins (FIG. 5B) mesenteric lymph nodes (MLN) (FIG. 5C) and liver (FIG. 5D). C57BL/6 germ-free mice were monocolonized as in (FIG. 5A) and anti-RNA (FIG. 5E) and anti-dsDNA (FIG. 5F) IgG autoantibodies were measured 8 weeks later. Th17 cells and Th1 cell frequencies were determined by intracellular FACS analysis of IL-17A and IFN-γ in small intestinal lamina propria (FIG. 5G) and MLN (FIG. 5H) CD44+ CD45+ CD4+ T cells from GF and monocolonized mice (*P<0.05, P<0.01, *P<0.001 and ****P<0.0001, when compared to GF control, Student's t test).
Figures 5G, 5H:
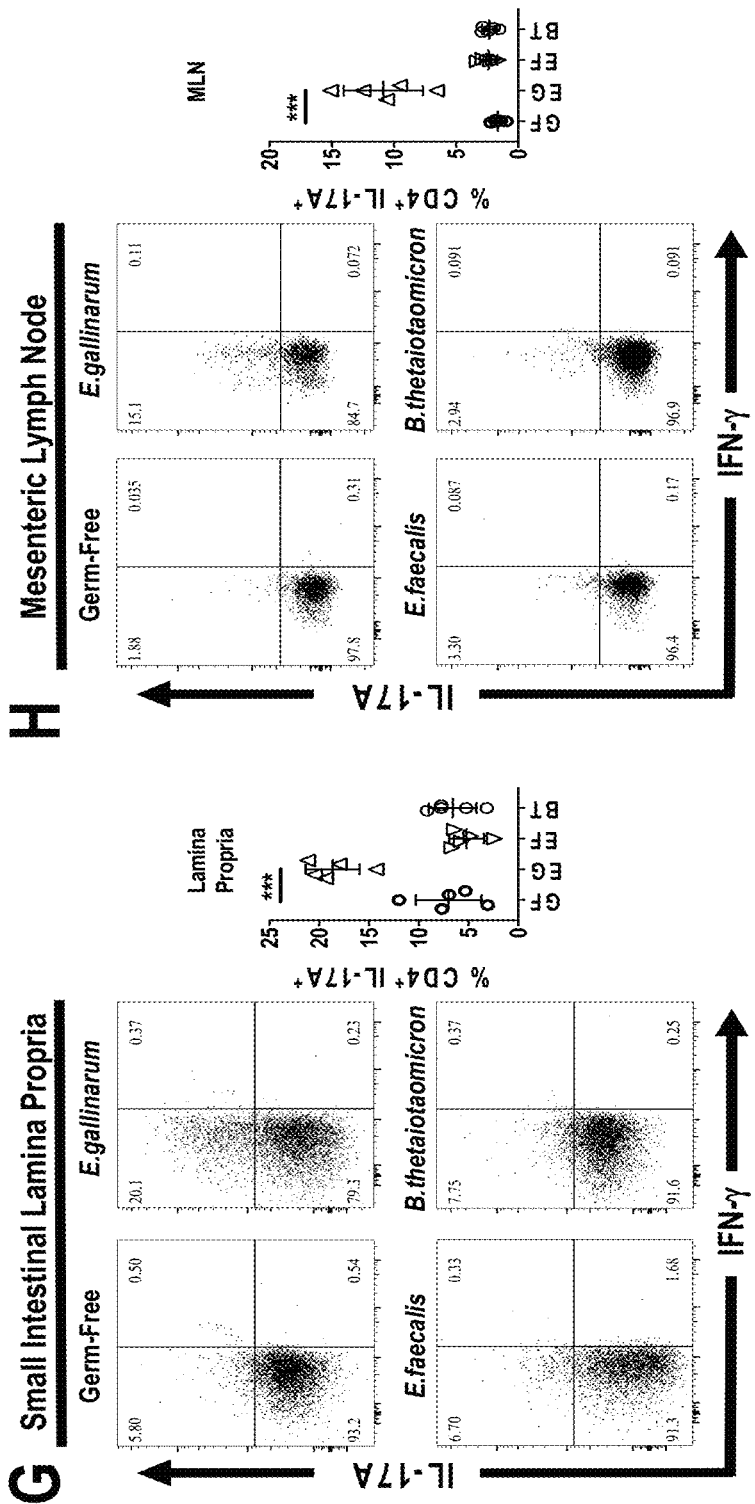
Figures 21A, 21B, 21C, 21D:
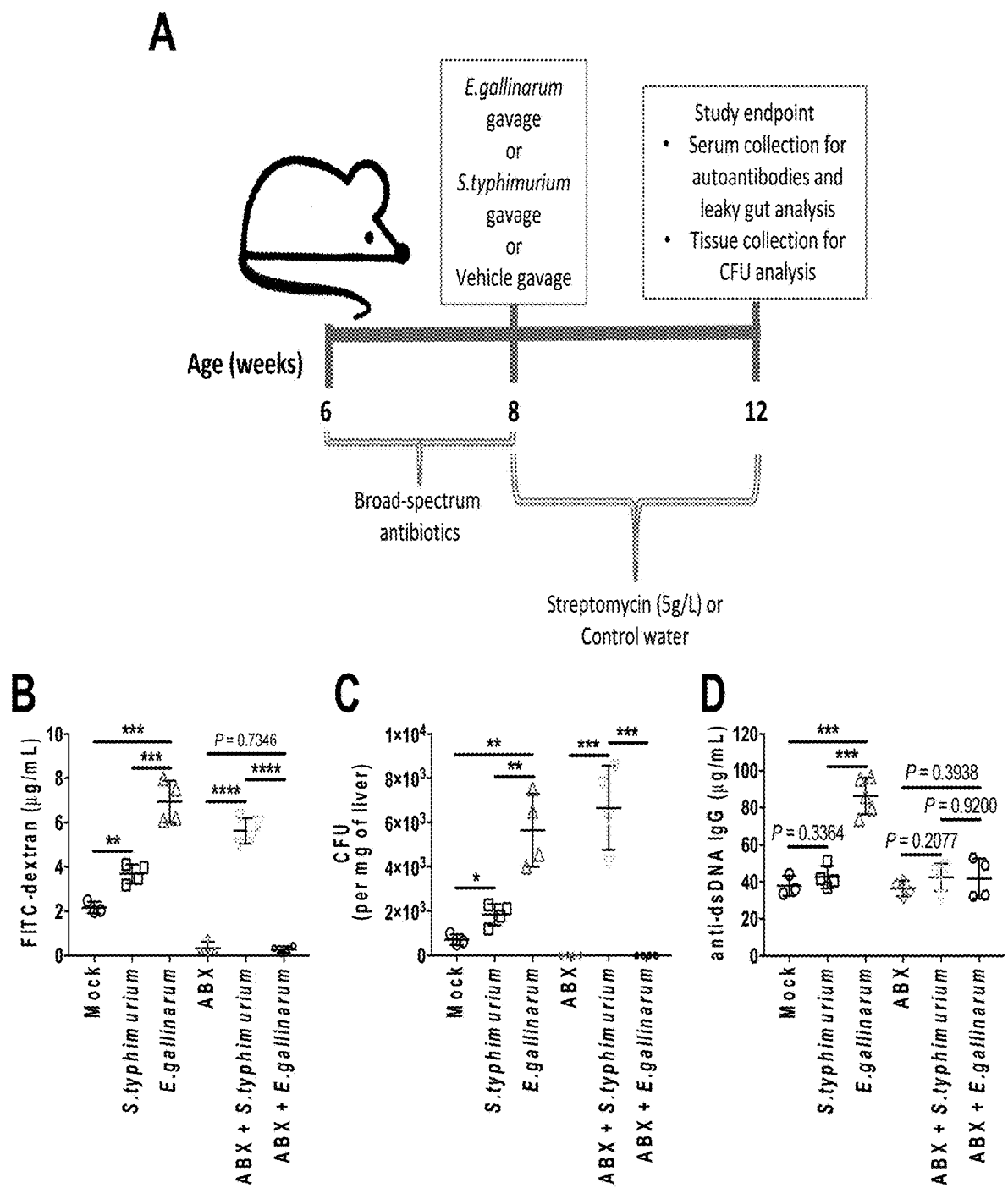
FIG. 21A through FIG. 21D, depicts the results of example experiments demonstrating that Salmonella typhimurium impairs the gut barrier and translocates in $(NZWxBXSB)F_1$ but does not induce autoantibodies. An attenuated strain of S. typhimurium with a streptomycin-resistance cassette was tested for translocation and autoantibody induction in $(NZWxBXSB)F_1$ mice. 6-week-old $(NZWxBXSB)F_1$ mice were treated with broad-spectrum antibiotics (ABX; 0.5 g/L of vancomycin, 1.0 g/L ampicillin, 1.0 g/L metronidazole and 1.0 g/L neomycin) in the drinking water for 2 weeks followed by gavage with E. gallinarum, S. typhimurium or vehicle every week starting at 8 weeks of age for 4 weeks.
Figure 22A:
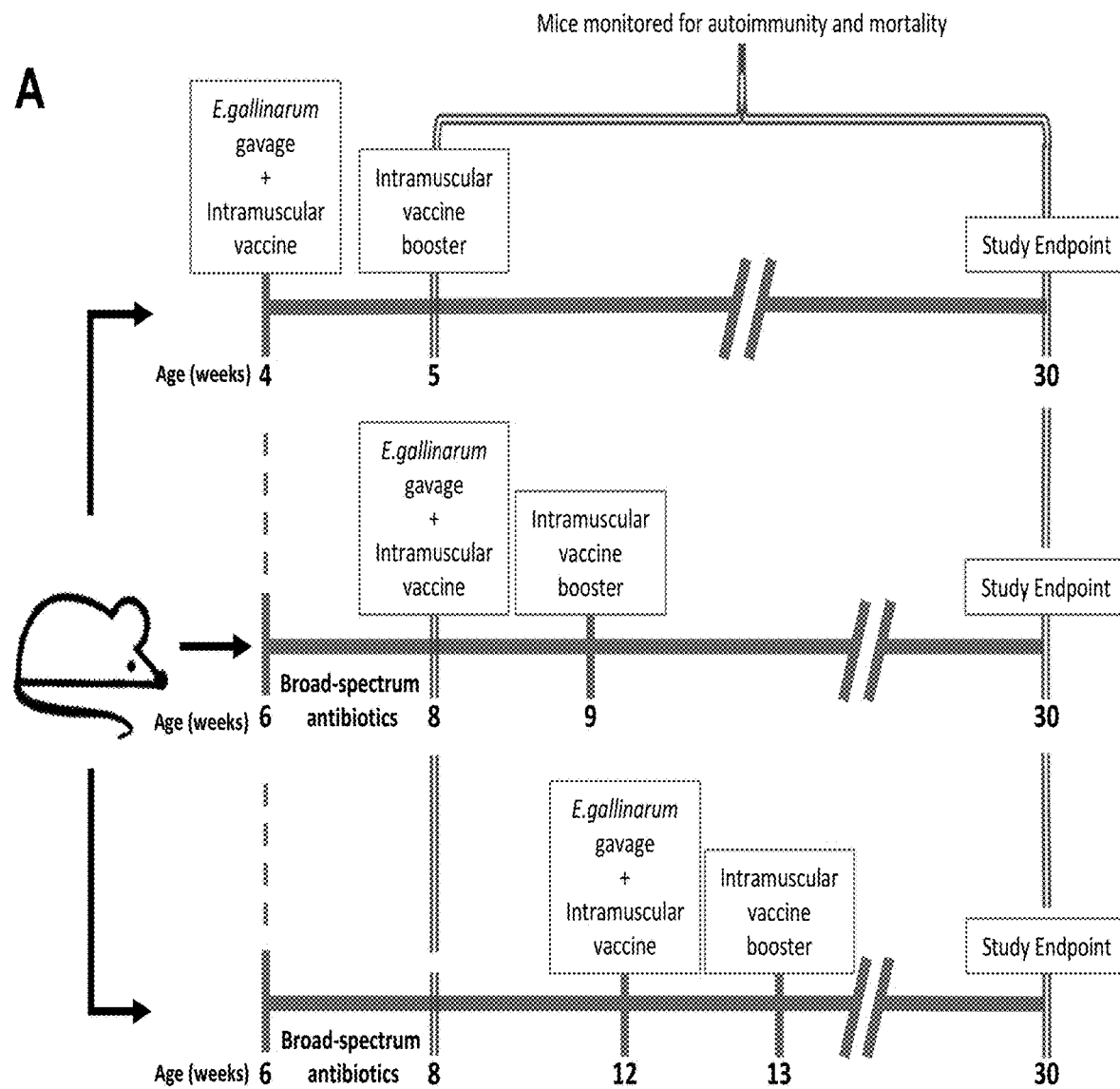
FIG. 22A through FIG. 22G, depicts the results of example experiments demonstrating that a therapeutic vaccine targeting E. gallinarum suppresses autoantibodies and prevents autoimmune mortality in $(NZWxBXSB)F_1$ mice.
Figures 22B, 22C, 22D, 22E, 22F, 22G:
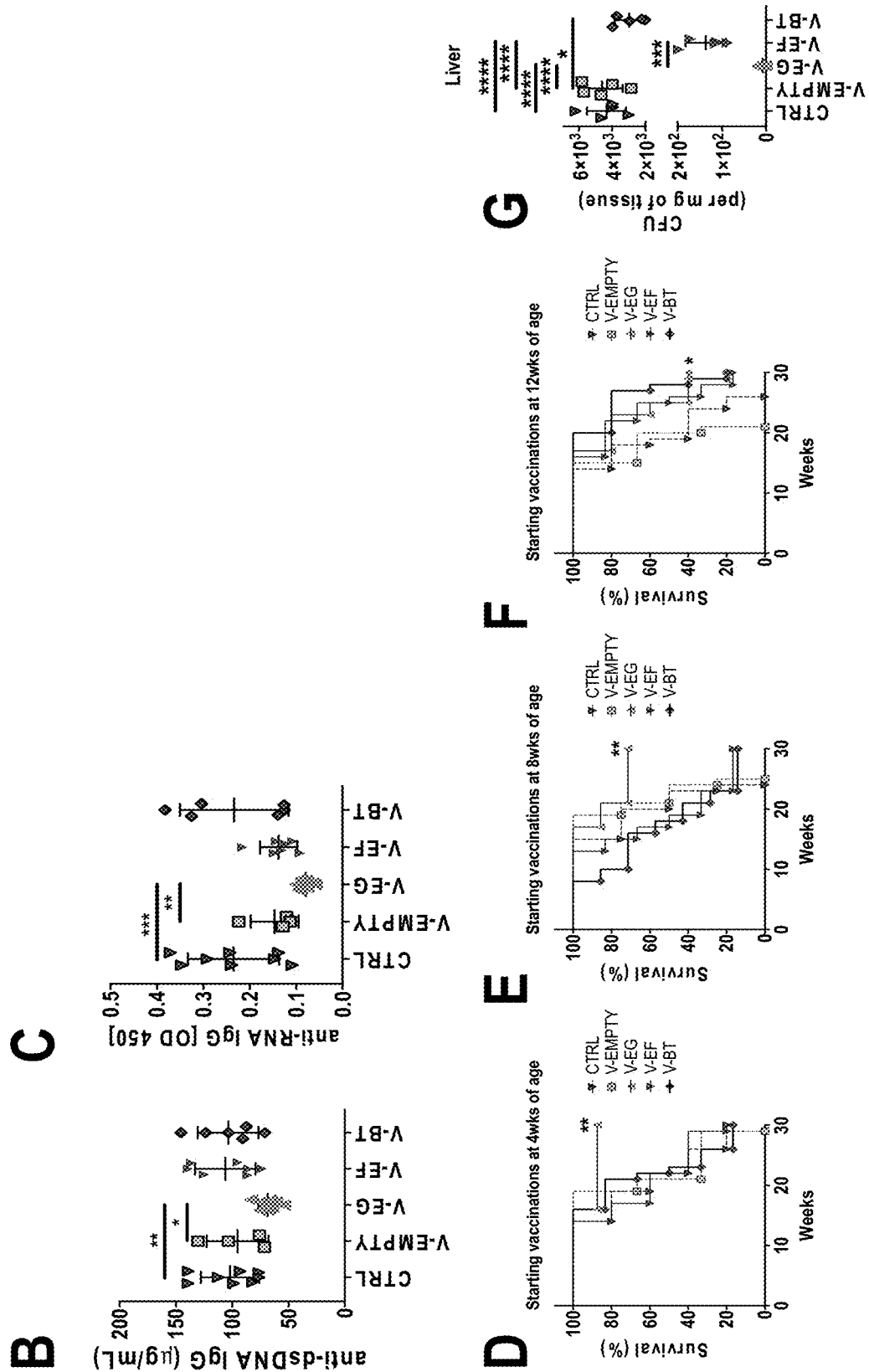

Since *E. gallinarum* has the potential for spontaneous translocation in the hybrid mice but not C57BL/6 mice under specific-pathogen-free (SPF) conditions, translocation was tested in germ-free mice monocolonized with *E. gallinarum* to determine if unrestricted growth allows for this phenomenon to occur. Indeed, *E. gallinarum* was capable of inducing barrier leakage and translocation to mesenteric veins, MLNs and livers of non-autoimmune mice within 3 weeks of colonization in the absence of a competing microbiota (FIG. 5A-FIG. 5D). Moreover, translocation promoted serum autoantibodies in aged mice (FIG. 5E-FIG. 5F). Autoantibody induction was not seen by monocolonization with other bacteria that either remain in the gut or translocate to tissues, i.e., *B. thetaiotaomicron* or *E. faecalis* (FIG. 5A-FIG. 5F). Monocolonization with *E. gallinarum* also induced Th17 in the lamina propria of the small intestine and MLN (FIG. 5G-FIG. 5H), consistent with the finding that Th17 cells are abundant in the hybrid model (in the absence of Th17-inducing segmented filamentous bacteria), and reduced with vancomycin (see FIG. 19). Furthermore, gavage of antibiotic-pretreated, autoimmune-prone hybrid mice with *E. gallinarum* versus a translocating pathogen, *S. typhimurium*, showed that only *E. gallinarum* induced autoantibodies, strongly supporting the autoimmune-promoting properties of *E. gallinarum* (FIG. 21). Gavage of antibiotic-pretreated (NZWxBXSB)$F_1$ hybrid mice with a high-level vancomycin-resistant *E. gallinarum* strain (isolated from the liver of a 16-week-old mouse that deteriorated despite chronic vancomycin treatment) also caused systemic autoimmune pathology (FIG. 21 and FIG. 22, control group); the phenotype was similar to that prevented by continuous antibiotic depletion in the spontaneous model without gavage of this strain (see FIG. 1), linking this pathobiont with translocation and induction of autoimmunity in vivo. Finally, to target the translocated pathobiont, an intramuscular vaccination strategy was developed using heat-killed *E. gallinarum* (FIG. 22A). Vaccination against *E. gallinarum*, but not *E. faecalis* or *B. thetaiotaomicron*, reduced the levels of serum autoantibodies and prolonged survival (FIG. 22B-FIG. 22F). Importantly, the vaccination also prevented translocation since no growth of *E. gallinarum* could be observed in internal organs (FIG. 22G). These findings support that a pathobiont-specific treatment approach can abrogate host autoimmune processes without targeting directly the immune system as conventional therapies do (such as immunosuppressive drugs) that associate with significant systemic adverse events.

Figures 6A, 6B, 6C:
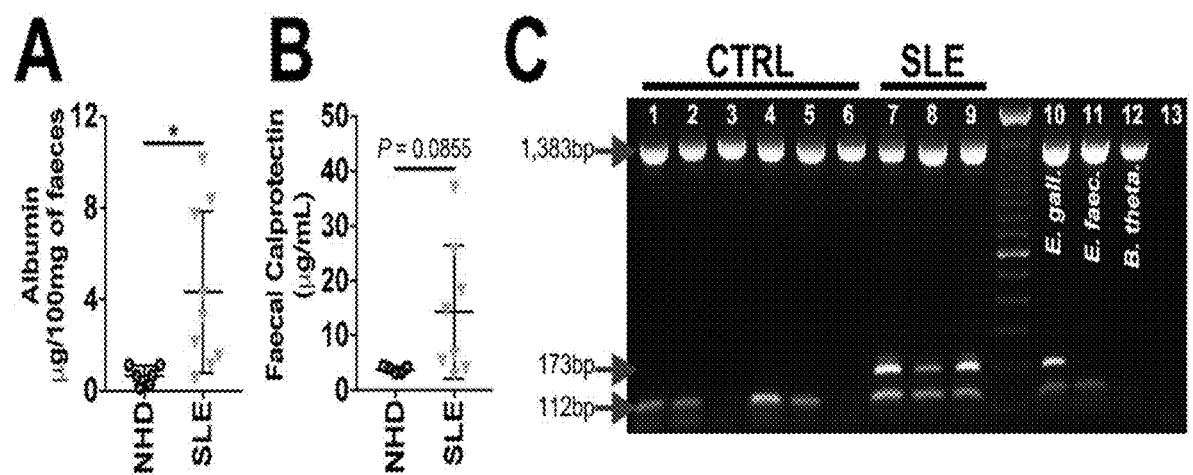
FIG. 6A through FIG. 6T, depicts the results of example experiments examining gut barrier function and *E. gallinarum* in liver biopsies of autoimmune patients with anti-*E. gallinarum* serum reactivities. Faeces from patients with SLE was screened for increased albumin (FIG. 6A) and calprotectin (FIG. 6B) as signs of an impaired gut barrier.
(FIG. 6C) Multiplex PCR for eubacterial (1,383 bp), *Enterococcus* genus (112 bp) and *E. gallinarum* (173 bp) DNA on sterilely obtained and processed liver biopsies from cadaveric liver transplant donors (CTRL) or SLE patients, bacterial strains as indicated, or water (lane 13).
Figure 6D:
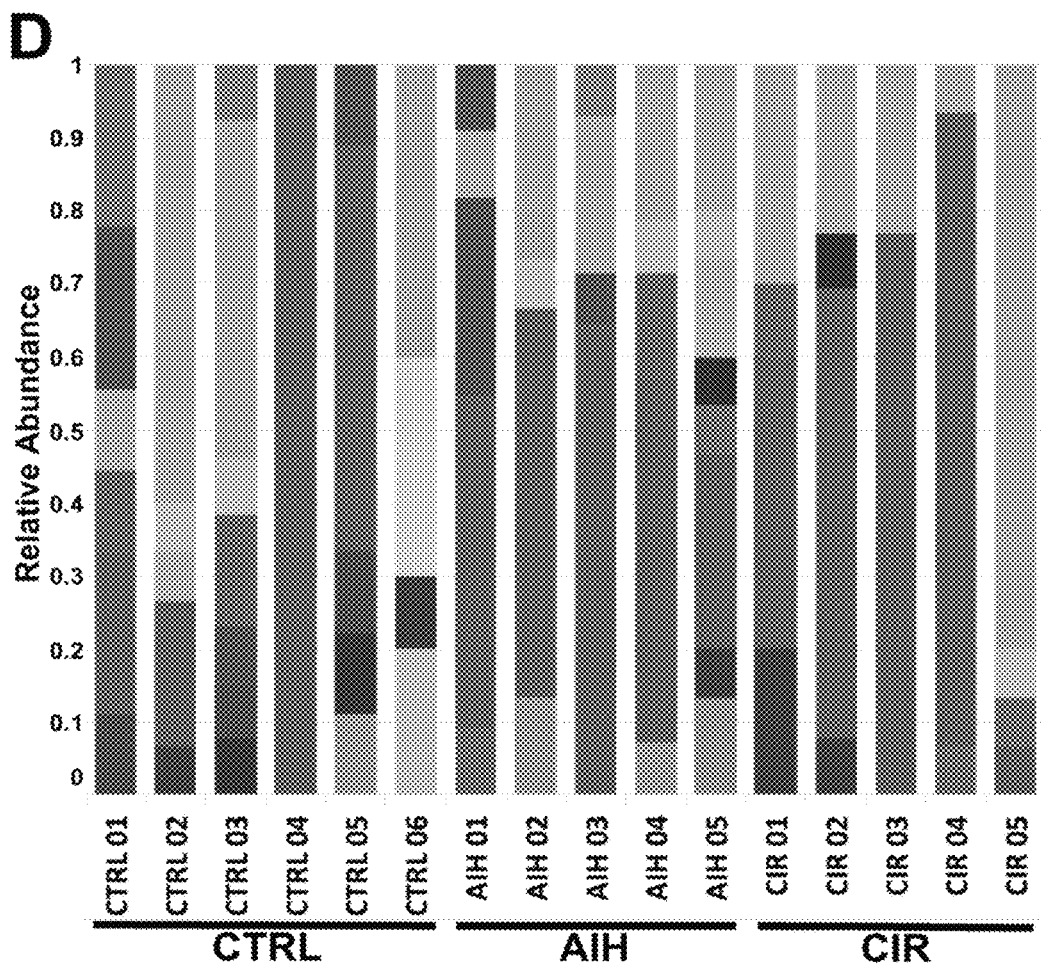
(FIG. 6D) 16S rDNA sequencing of controls as in (C), autoimmune hepatitis (AIH) and non-AIH cirrhosis (CIR) patients.
Figures 6E, 6F, 6G, 6H, 6I, 6J, 6K, 6L:
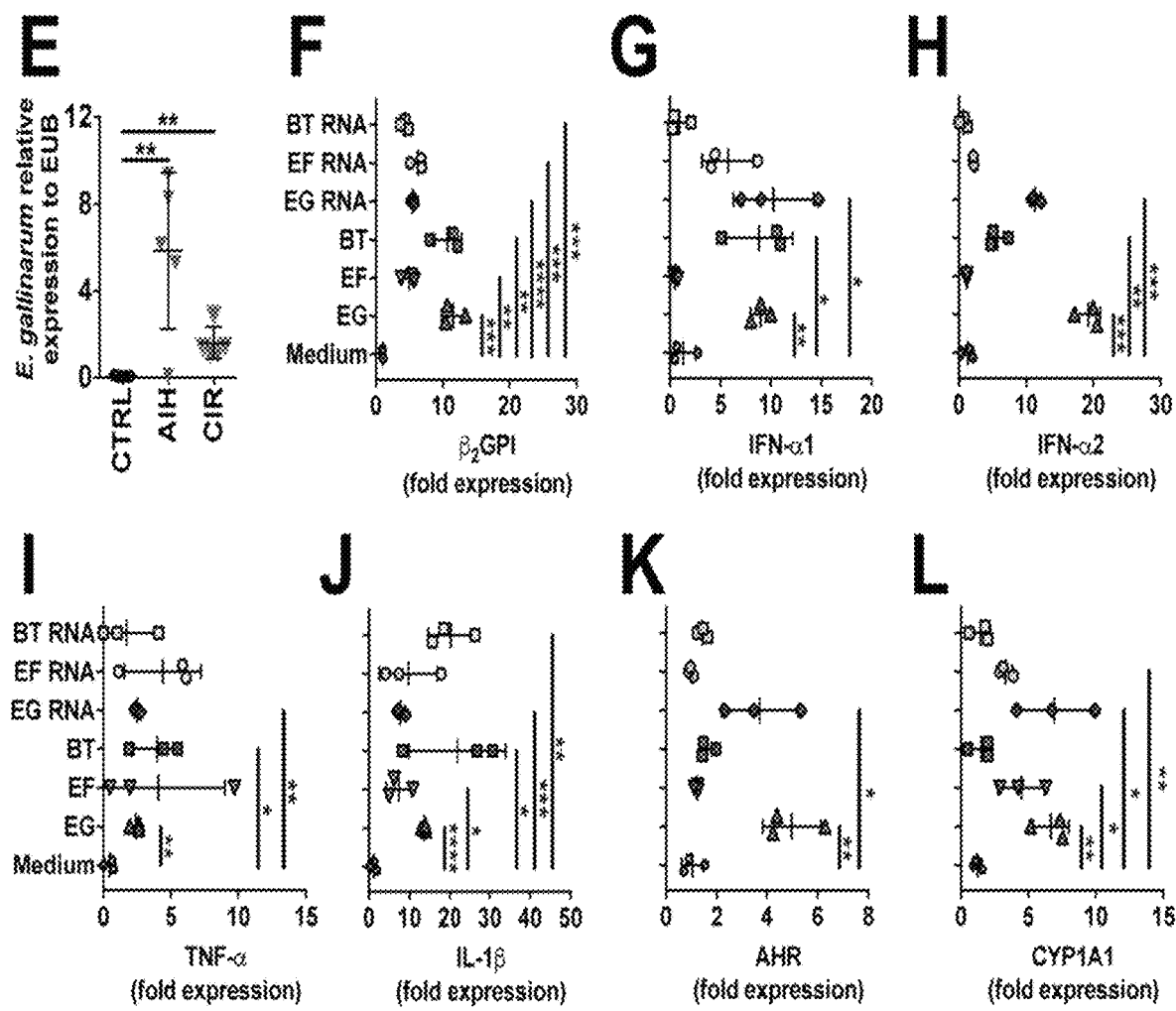
(FIG. 6E) Liver biopsies from CTRL, AIH and CIR patients were tested for *E. gallinarum* (EG) DNA by qPCR and normalized to any eubacterial (EUB) signal.
(FIG. 6F-FIG. 6L) RT-qPCR of human primary hepatocytes stimulated with EG, *E. faecalis* (EF), *B. thetaiotaomicron* (BT) as in FIG. 4. SLE and AIH sera were screened for anti-EG IgA (FIG. 6M), IgG (FIG. 6N), anti-EG RNA IgA (FIG. 6O), IgG (FIG. 6P) and anti-human RNA IgG (FIG. 6Q) by ELISA.
Figures 6M, 6N, 6O, 6P, 6Q, 6R, 6S, 6T:
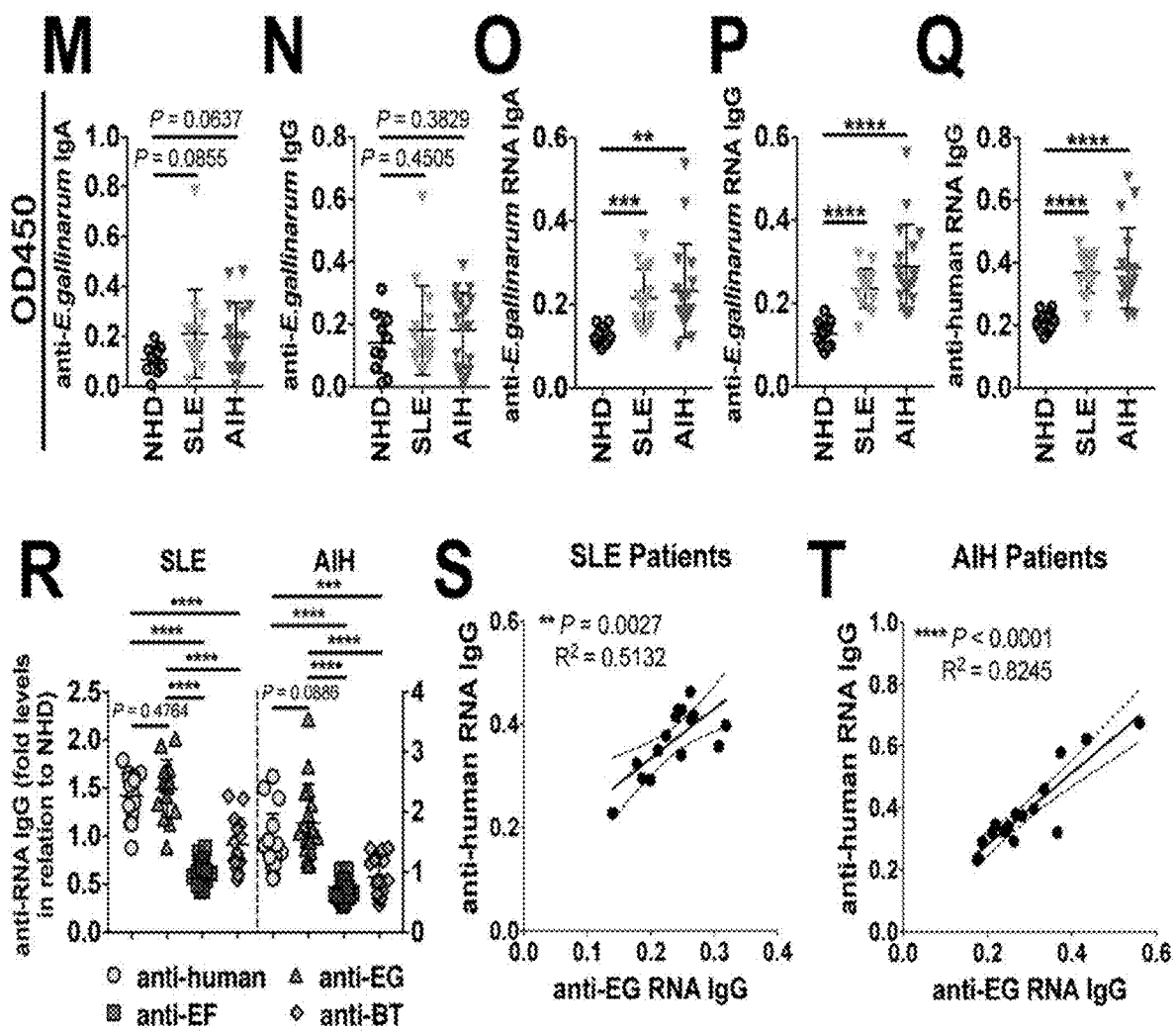
(FIG. 6R) SLE and AIH serum IgG levels against human, EG, EF, or BT RNA normalized to NHD sera. Correlation between anti-EG RNA IgG and autoantibodies in SLE (FIG. 6S) and AIH (FIG. 6T) patients. P<0.002, *P<0.0006 and ****P<0.0001, when compared with controls or medium (ANOVA followed by the Bonferroni test).
Figures 7A, 7B, 7C, 7D, 7E, 7F:
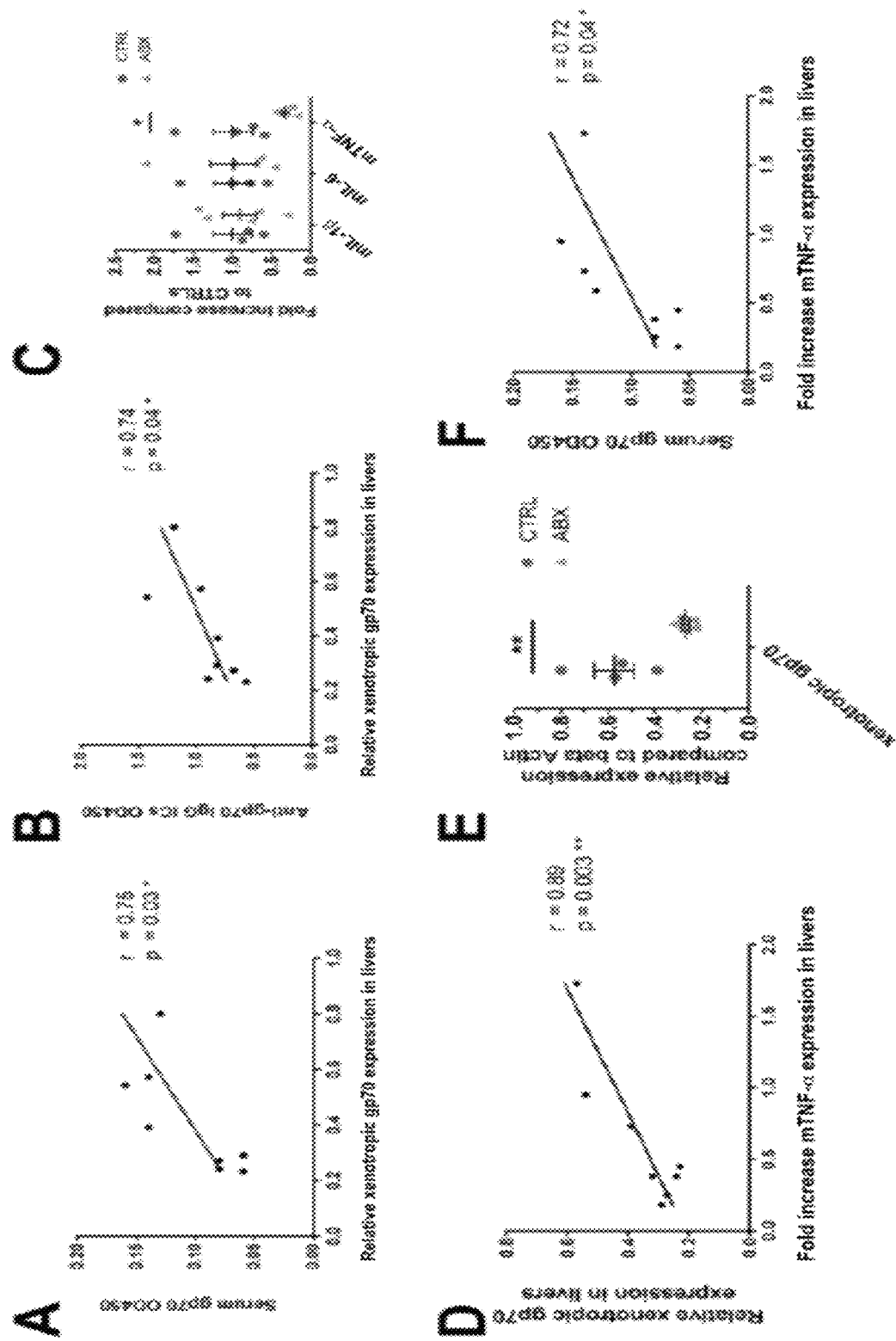
FIG. 7A through FIG. 7L, depicts the results of example experiments demonstrating the influence of oral antibiotics on serum and hepatic endogenous retroviral (ERV) protein gp70 and anti-ERV gp70- and -β$_2$GPI-directed autoimmune responses in (NZWxBXSB)F$_1$ mice. 5-week-old (NZWxBXSB)F$_1$ mice were treated for 8 weeks with control water (CTRL) or broad-spectrum antibiotics (ABX; 0.5 g/L of vancomycin, 1.0 g/L ampicillin, 1.0 g/L metronidazole and 1.0 g/L neomycin) in the drinking water. Serum ERV gp70 (FIG. 7A and FIG. 7F) and anti-ERV gp70 IgG immune complexes (ICs) (FIG. 7B and FIG. 7G) were determined by ELISA and correlated with the relative expression of xenotropic ERV gp70 in livers of 12-week-old (NZWxBXSB)F$_1$ mice that was defined by RT-qPCR. IL-1β, IL-6, TNF-α (FIG. 7C, FIG. 7D and FIG. 7F) and ERV gp70 (FIG. 7A, FIG. 7B, FIG. 7D, and FIG. 7E) expression in the liver were determined by RT-qPCR. Fold increase of cytokines in ABX—compared to control-treated animals is shown in (FIG. 7C), reduction of relative expression of xenotropic ERV gp70 by ABX is shown in (FIG. 7E). *P<0.04 and **P<0.003 when compared with control mice (Student's t-test). The linear regression equation, Pearson's correlation coefficient, and p-value are shown in the panels (FIG. 7A, FIG. 7B, FIG. 7D, and FIG. 7F). Vancomycin (0.5 g/L; VANC), ampicillin (1.0 g/L; AMP), metronidazole (1.0 g/L; METR), neomycin (1.0 g/L; NEO) or control water treatment (CTRL) were orally administered in the drinking water starting at 6 weeks of age. Serum levels of anti-β$_2$GPI IgG (FIG. 7H-FIG. 7J), ERV gp70 protein (FIG. 7K), and anti-ERV gp70 IgG ICs (FIG. 7L) were measured by ELISA at the indicated time points until 20 weeks of age or death from autoimmunity (*P<0.05, **P<0.002, ANOVA followed by the Bonferroni test).
Figures 7G, 7H, 7I, 7J:
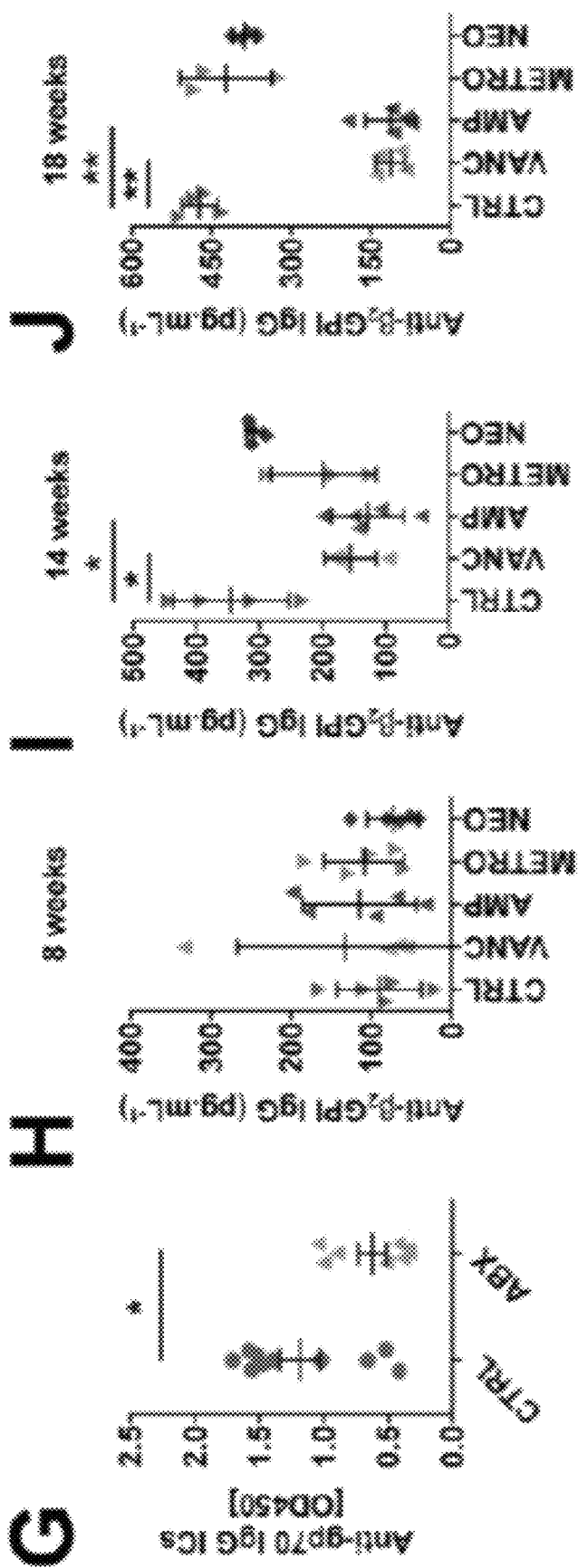
Figure 7K:
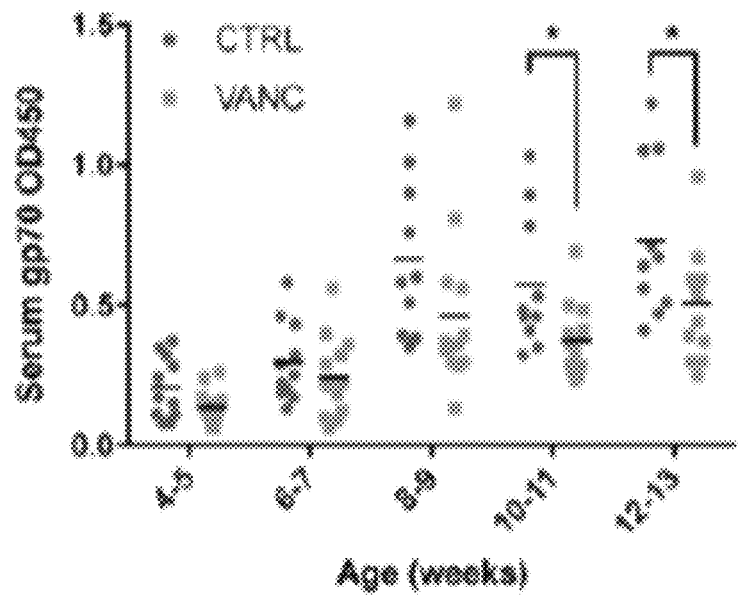
Figure 7L:
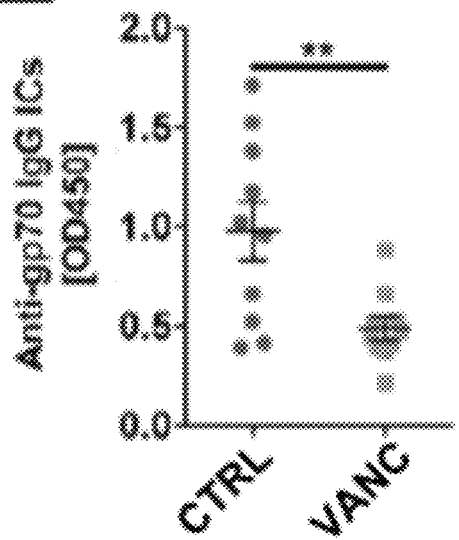
Figures 8A, 8B:
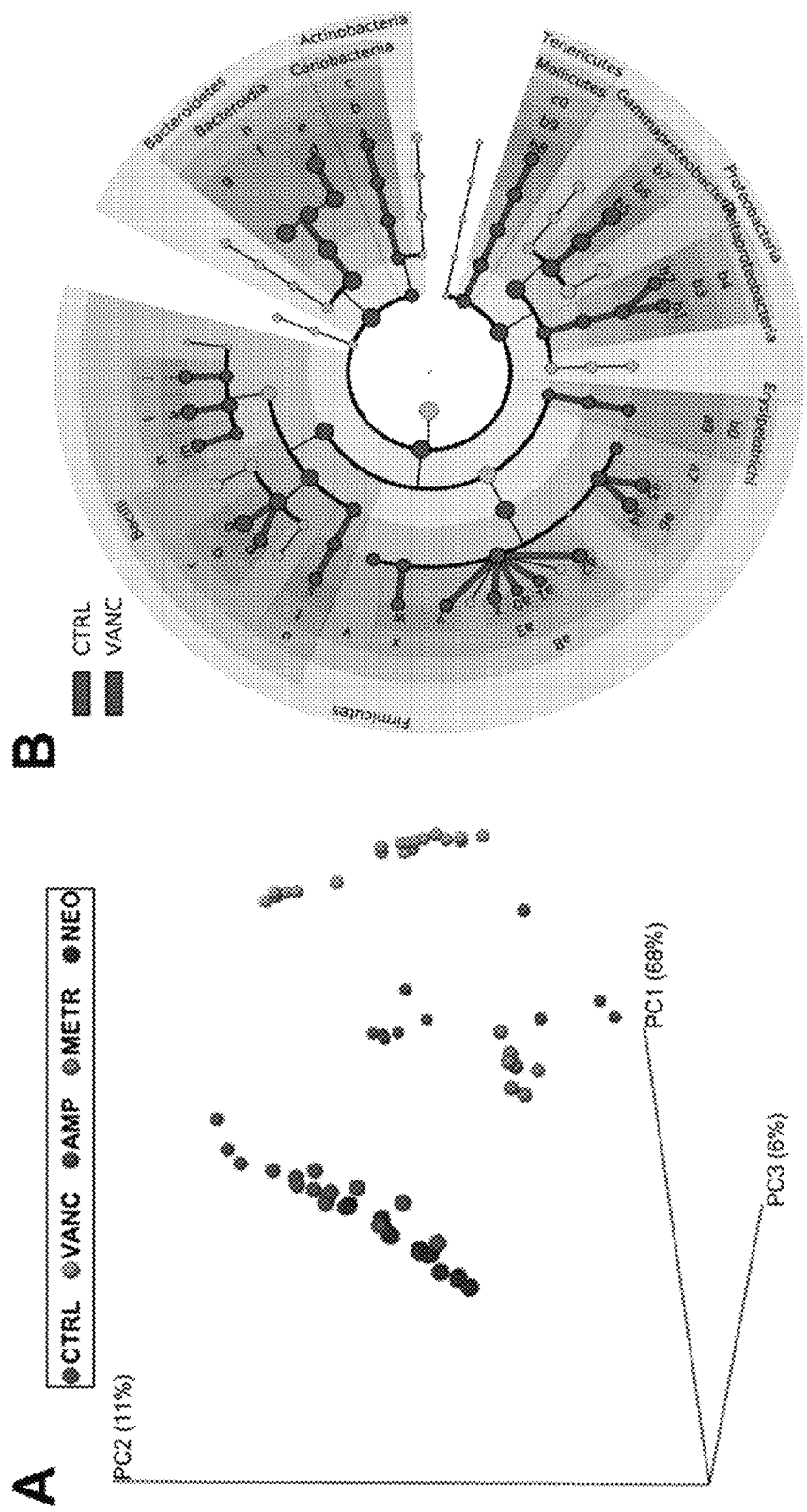
FIG. 8A through FIG. 8C, depicts the results of example experiments of 16S rDNA sequencing of faecal pellets from antibiotics- and control-treated (NZWxBXSB)F$_1$ mice. Dual-index 16S rDNA sequencing of the V4 variable region from longitudinally collected faecal pellets from (NZWxBXSB)F$_1$ mice was performed as described elsewhere herein. Vancomycin (0.5 g/L; VANC), ampicillin (1.0 g/L; AMP), metronidazole (1.0 g/L; METR), neomycin (1.0 g/L; NEO) or control water treatment (CTRL) were orally administered in the drinking water starting at 6 weeks of age and faecal pellets were analysed at 16 weeks of age.
Figure 8C:
Figure 9A:
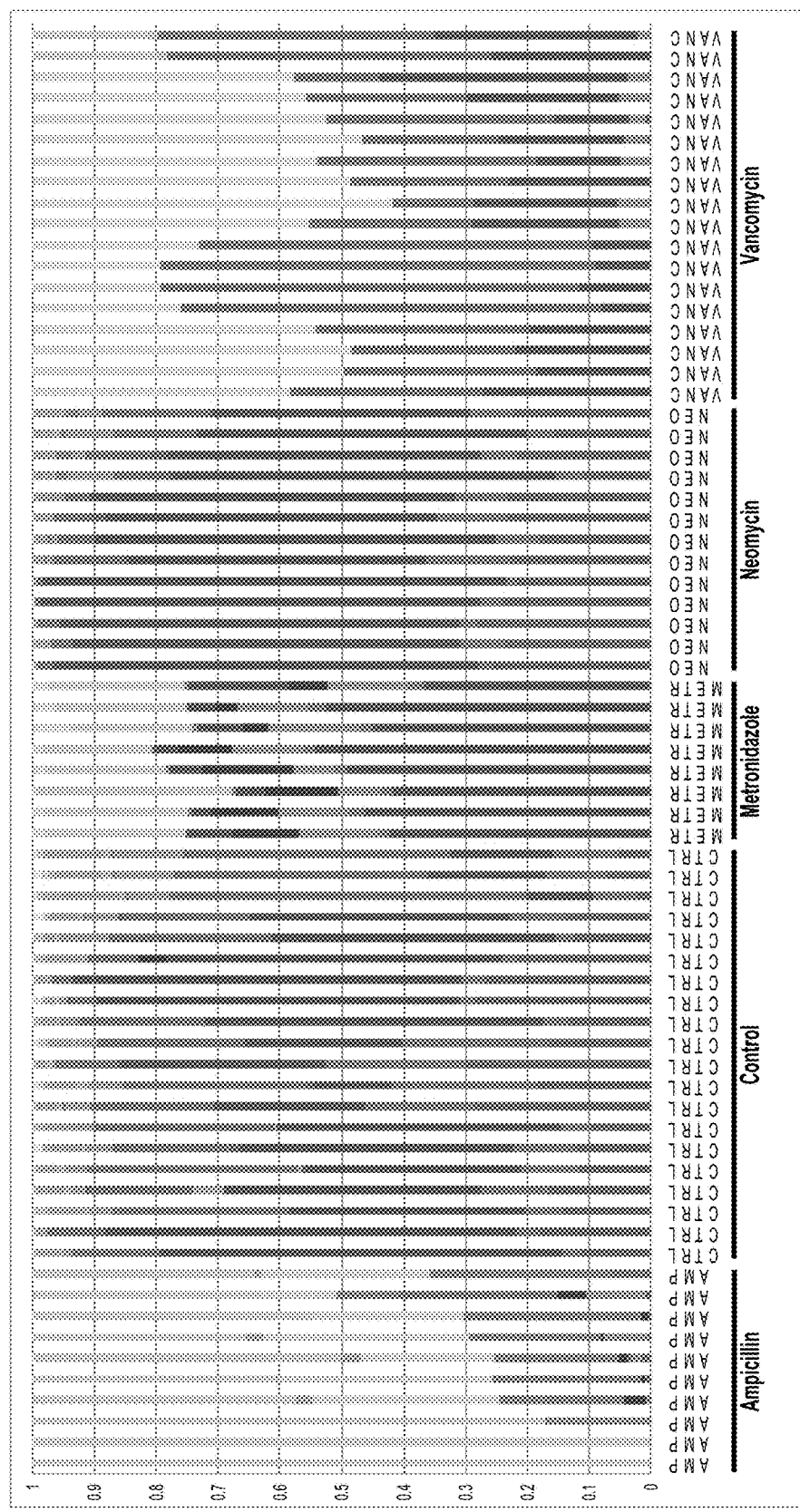
Figures 10A, 10B, 10C, 10D:
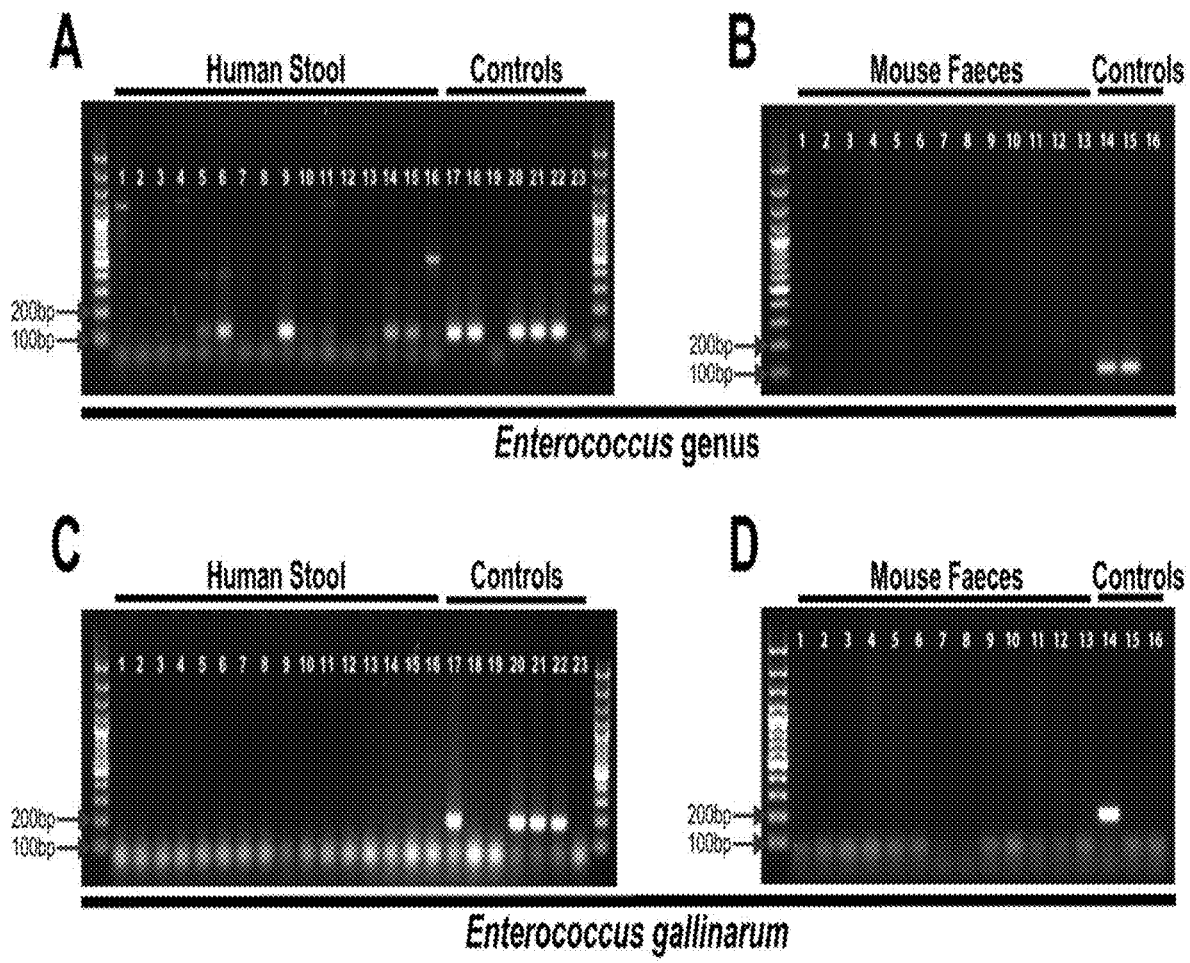
FIG. 10A through FIG. 10D, depicts the results of example experiments examining human and murine stool screening for *Enterococcus* genus and *Enterococcus gallinarum* by PCR.

Based on the autoimmune-promoting effects of *E. gallinarum* translocation in mice, patient cohorts with systemic and organ-specific autoimmunity was explored. Longitudinal stool analyses from SLE patients supported impaired gut barrier function with increased faecal albumin and calprotectin (FIG. 6A-FIG. 6B). *E. gallinarum* translocation to human livers was thus explored in patients with SLE and autoimmune hepatitis (AIH) that display serologic features of lupus including antinuclear antibodies and anti-dsDNA IgG (Table 1) (Fallatah and Akbar, 2012, Autoimmune Dis, 2012, 312817). Liver biopsies from 3 SLE patients indeed contained *E. gallinarum* compared to controls obtained from healthy liver transplant donors with normal liver histology (FIG. 6C). Interestingly, 4 out of 6 control livers contained signals of the *Enterococcus* genus suggesting that other species than *E. gallinarum* reside inside normal human livers. Next, 16S rDNA sequencing was performed on sterilely obtained human liver tissues from these controls, AIH, and cirrhosis patients that are known to have a grossly impaired gut barrier with multiple bacteria translocating (Qin et al., 2014, Nature, 513, 59-64). The microbial community analysis revealed that the *Enterococcus* genus predominates over other genera in diseased tissues (FIG. 6D). Importantly, the majority of AIH liver biopsies but not healthy control livers were positive specifically for E. *gallinarum* (FIG. 6E), supporting *E. gallinarum* translocation to human livers in both SLE and AIH. Similar to the effects seen with murine hepatocytes (see FIG. 4A-FIG. 4I), primary human hepatocytes stimulated with *E. gallinarum* led to marked induction of autoimmune-promoting factors and cytokines including type I interferon and AHR-CYP1A1 (FIG. 6F-FIG. 6L), the antimicrobial and Th17-inducing pathway discussed above (Veldhoen et al., 2008, Nature, 453, 106-109; Moura-Alves et al., 2014, Nature, 512, 387-392; Schiering et al., 2017, Nature, 542, 242-245). Lastly, signs of systemic immune responses to *E. gallinarum* were explored in patients with SLE and AIH. Consistent with enhanced adaptive immune responses to *E. gallinarum*, the majority of SLE and AIH patients showed increased serum IgA titers against *E. gallinarum* and particularly its RNA, which may act as a potential TLR7/8 stimulus and cross-reactive trigger (FIG. 6M-FIG. 6O). When comparing anti-human RNA IgG autoantibody titers in SLE and AIH patients with anti-*E. gallinarum* RNA IgG, they were equally increased compared to those against RNA from other bacteria (*E. faecalis, B. thetaiotaomicron*), and titers correlated with each other (FIG. 6P-FIG. 6T). This data indicates that the anti-*E. gallinarum* antibodies can be used to diagnose subjects with an autoimmune disorder, and to select treatment candidates for lowering or depleting *Enterococcus* sp.

Taken together, these findings support a scenario in which *E. gallinarum* translocates to the livers of autoimmune patients and individuals with impaired gut barrier function. This process leads to systemic inflammatory and adaptive immune responses that may promote autoantibody production, epitope spreading, and tissue damage.

Figure 23:
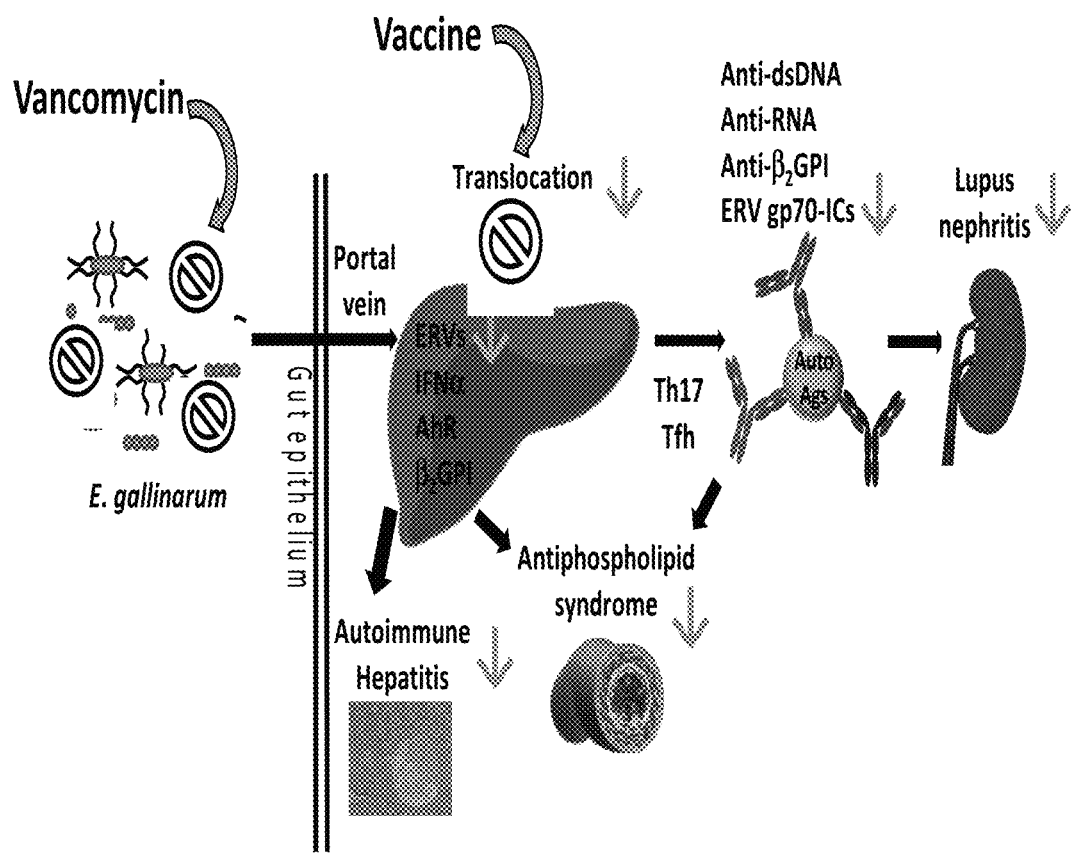
FIG. 23 depicts a schematic representation of the mechanisms of action of E. gallinarum on autoimmunity. E. gallinarum breaches the small intestinal barrier, translocates via lymphatics and portal vein to reach MLN and liver. Within the liver, E. gallinarum stimulates hepatocytes to induce endogenous retroviral proteins (ERVs), interferon (IFN)-α, aryl hydrocarbon receptor (AhR) and autoantigen 32GPI. In addition, Th17 and Tfh cells are induced in the gut and secondary lymphoid organs (not shown). These events culminate in organ inflammation with cellular infiltrates and induction of pathogenic autoantibodies that drive features of lupus nephritis, antiphospholipid syndrome and autoimmune hepatitis. Continuous administration of oral vancomycin or an intramuscular vaccine against E. gallinarum prevent translocation, Th17/Tfh cell induction, autoantibody production and autoimmune-related mortality.

In conclusion, it is demonstrated herein that a gram-positive gut pathobiont intrinsically translocates in autoimmune-prone hosts and was linked mechanistically to gut barrier breakdown and autoimmune pathogenesis (modelled in FIG. 23). Microbial and host pathways such as the shikimate and AHR-CYP1A1 pathways likely contribute to autoimmunity in this setting. In addition, *E. gallinarum* (and its phage) RNA, released during bacterial replication in tissues, might be both an innate trigger for TLR7/8 and type I interferon as well as a potential cross-reactive source for anti-human RNA autoantibodies that can lead to epitope spreading to other autoantigens (Ruff and Kriegel, 2015, Trends Mol Med, 21, 233-244).

Spontaneous translocation in monocolonized, non-autoimmune-prone mice and detection of *E. gallinarum* in cirrhotic livers of patients with an altered gut-liver homeostasis suggest that both microbial and host factors facilitate translocation. Once translocated to tissues, it is suspected that this and related species are capable of causing disease pathology depending on the genetic background of the host. MHC and other genetic risk loci may dictate if a patient develops systemic or organ-specific autoimmunity, or if tissue colonization contributes mainly to innate inflammation as in cirrhosis. The presence of certain pathobionts predominantly in deep tissues provides an opportunity for unique treatment approaches such as intramuscular vaccination or targeted antibiotics. Similar approaches would be plausible for other gut commensals that translocate in disease states and could thus represent a new paradigm of how to target pathobionts without interfering with the resident microbiota, the vast majority with beneficial functions.

In summary, the gut microbiota can have multiple effects on autoimmunity depending on its proximity to the host immune system. Loss of luminal commensals that secrete protective metabolites such as short-chain fatty acids leads to regulatory T cell deficiencies and thereby autoimmunity (Atarashi et al., 2011, Science, 331, 337-341; Smith et al., 2013, Science 341, 569-573; Arpaia et al., 2013, Nature, 504, 451-455); gut epithelial-adherent segmented filamentous bacteria drive Th17 and Tfh cells, which promotes joint autoimmunity (Wu et al., 2010, Immunity, 32, 815-827);

translocating bacteria as shown in the present study can not only skew T helper cell differentiation but also directly act on colonized tissues such as the liver by inducing autoantigens, ERV proteins, cytokines and other autoimmune-promoting factors. Taken together, the complexity of host tissue-microbiota interactions need to be taken into account in chronic autoimmunity but may eventually provide new therapeutic avenues for these debilitating and potentially lethal diseases.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating an autoimmune disease or disorder in a subject in need thereof, comprising administering to the subject an effective amount of a composition comprising an immunotherapeutic agent that induces an anti-*Enterococcus gallinarum* immune response and which reduces the amount or activity of *Enterococcus gallinarum* in the subject.

2. The method of claim 1, wherein the immunotherapeutic agent is selected from the group consisting of a vaccine, an *Enterococcus gallinarum* antigen, and a nucleic acid molecule encoding an *Enterococcus gallinarum* antigen.

3. The method of claim 2, wherein the vaccine comprises a heat-inactivated *Enterococcus gallinarum* bacterium.

4. The method of claim 1, wherein the autoimmune disease or disorder is selected from the group consisting of systemic lupus erythematosus (SLE), autoimmune hepatitis (AIH), primary sclerosing cholangitis, primary biliary cirrhosis, antiphospholipid syndrome, Sjogren's syndrome, scleroderma, dermatomyositis, polymyositis, vasculitis, interstitial lung disease, type 1 diabetes, multiple sclerosis, and rheumatoid arthritis.

* * * * *